US009283269B2

(12) United States Patent
Girsh

(10) Patent No.: US 9,283,269 B2
(45) Date of Patent: Mar. 15, 2016

(54) METHOD FOR REDUCING THE ALLERGENICITY OF ANIMAL DANDER

(71) Applicant: IMMUNOPATH PROFILE, INC., Naples, FL (US)

(72) Inventor: Leonard S. Girsh, Naples, FL (US)

(73) Assignee: IMMUNOPATH PROFILE, INC., Naples, FL (US)

( * ) Notice: Subject to any disclaimer, the term of this patent is extended or adjusted under 35 U.S.C. 154(b) by 0 days.

(21) Appl. No.: 14/483,399

(22) Filed: Sep. 11, 2014

(65) Prior Publication Data

US 2015/0072007 A1 Mar. 12, 2015

Related U.S. Application Data

(60) Continuation of application No. 11/592,530, filed on Nov. 2, 2006, now abandoned, which is a continuation of application No. 10/269,613, filed on Oct. 11, 2002, now abandoned, said application No. 11/592,530 is a continuation-in-part of application No. 09/611,857, filed on Jul. 7, 2000, now abandoned, which is a division of application No. 09/080,990, filed on May 19, 1998, now abandoned, which is a continuation-in-part of application No. 09/058,469, filed on Apr. 10, 1998, now abandoned, which is a continuation-in-part of application No. 09/058,430, filed on Apr. 10, 1998, now abandoned, said application No. 11/592,530 is a continuation-in-part of application No. 09/731,608, filed on Dec. 7, 2000, now abandoned, and a continuation-in-part of application No. 09/639,859, filed on Aug. 16, 2000, now Pat. No. 6,974,796.

(60) Provisional application No. 60/358,890, filed on Feb. 22, 2002, provisional application No. 60/350,119, filed on Nov. 9, 2001, provisional application No. 60/149,338, filed on Aug. 17, 1999.

(51) Int. Cl.
| A61K 31/045 | (2006.01) |
| A61K 31/21 | (2006.01) |
| A61K 39/35 | (2006.01) |
| A61K 35/20 | (2006.01) |
| A61K 31/198 | (2006.01) |
| A61K 31/20 | (2006.01) |
| A61K 31/737 | (2006.01) |
| A61K 38/39 | (2006.01) |
| A61K 39/39 | (2006.01) |
| A61K 39/00 | (2006.01) |

(52) U.S. Cl.
CPC .............. *A61K 39/35* (2013.01); *A61K 31/198* (2013.01); *A61K 31/20* (2013.01); *A61K 31/737* (2013.01); *A61K 35/20* (2013.01); *A61K 38/39* (2013.01); *A61K 39/39* (2013.01); *A61K 2039/55511* (2013.01); *A61K 2039/55566* (2013.01)

(58) Field of Classification Search
None
See application file for complete search history.

(56) References Cited

U.S. PATENT DOCUMENTS

| 3,400,199 A | 9/1968 | Balassa |
| 3,917,859 A | 11/1975 | Terada et al. |
| 3,920,819 A | 11/1975 | Stephens et al. |
| 4,045,589 A | 8/1977 | Petrowski et al. |
| 4,145,447 A | 3/1979 | Fisher et al. |
| 4,196,202 A | 4/1980 | Okada |
| 4,310,561 A | 1/1982 | Buddemeyer et al. |
| 4,562,080 A | 12/1985 | Tenn |
| 4,752,618 A | 6/1988 | Mascioli et al. |
| 4,803,070 A | 2/1989 | Cantrell et al. |
| 4,857,326 A | 8/1989 | Stitt |

(Continued)

FOREIGN PATENT DOCUMENTS

| WO | WO 92/21752 | 12/1992 |
| WO | WO 97/10723 | 3/1997 |
| WO | WO 0228187 A1 * | 4/2002 ............. A01N 59/16 |

OTHER PUBLICATIONS

U.S. Appl. No. 10/765,664, filed Jan. 26, 2004, Girsh.
U.S. Appl. No. 10/868,697, filed Jun. 14, 2004, Girsh.
U.S. Appl. No. 12/466,850, filed May 15, 2009, Girsh.
Henschen, A. et al. "Covalent Structure of Fibrinogen" *Annals of New York Academy of Sciences*, 1983, pp. 28-43, vol. 408.
Wayman, K.I. et al. "Neurodevelopmental outcome of young children with extrahepatic biliary atresia 1 year after liver transplantation" *The Journal of Pediatrics*, Dec. 1977, pp. 894-898, vol. 131, No. 6.

(Continued)

*Primary Examiner* — Robert A Wax
*Assistant Examiner* — Amanda Heyes
(74) *Attorney, Agent, or Firm* — Saliwanchik, Lloyd & Eisenschenk

(57) ABSTRACT

The present invention relates to a non-invasive medical therapy and a composition for avoiding organ transplantation, or controlling biological rejection of transplanted organs, or treating organs under consideration for replacement by transplant, and otherwise treating aged, diseased and/or abnormal tissues and/or organs. More specifically, the non-invasive medical therapy involves administering to a patient an elemental nutritional feeding comprising a free amino acid profile simulating and/or replicating a targeted diseased or transplanted tissue and/or organ. The subject invention provides methods of inactivating reactive component epitopes of moieties pathogenic substances or producing immunogenic compositions containing pathogenic substances comprising contacting pathogenic substances, or compositions containing pathogenic substances, with super critical carbon dioxide or liquid nitrogen. Similar benefits are produced using high HLB surfactants also reducing carcinogenic factors. In various embodiments, the pathogenic reactive components, epitopes, moieties or substances are inactivated and processed into immunogenic compositions. The subject invention also provides oral mucosal delivery systems for the subject therapeutic compositions and/or medications, and/or vaccines that avert the need for parenteral administration in the medical and veterinary fields.

7 Claims, 14 Drawing Sheets

(56) References Cited

U.S. PATENT DOCUMENTS

| | | | |
|---|---|---|---|
| 4,871,550 A | 10/1989 | Millman | |
| 5,004,593 A | 4/1991 | Ames et al. | |
| 5,200,195 A | 4/1993 | Dong et al. | |
| 5,236,899 A | 8/1993 | Durette | |
| 5,397,778 A | 3/1995 | Forse et al. | |
| 5,545,667 A | 8/1996 | Wiersema et al. | |
| 5,654,337 A | 8/1997 | Roentsch et al. | |
| 5,674,853 A | 10/1997 | Forse et al. | |
| 5,739,107 A | 4/1998 | Cohen et al. | |
| 5,753,211 A | 5/1998 | Garson et al. | |
| 5,753,296 A | 5/1998 | Girsh | |
| 5,855,619 A | 1/1999 | Caplan et al. | |
| 5,902,617 A | 5/1999 | Pabst | |
| 5,904,924 A | 5/1999 | Gaynor et al. | |
| 5,929,030 A | 7/1999 | Hamied et al. | |
| 5,958,684 A | 9/1999 | Van Leeuwen et al. | |
| 5,985,284 A | 11/1999 | Lowell | |
| 6,153,582 A | 11/2000 | Skelnik | |
| 6,176,842 B1 | 1/2001 | Tachibana et al. | |
| 6,197,356 B1 | 3/2001 | Girsh | |
| 6,228,400 B1 | 5/2001 | Lee et al. | |
| 6,479,059 B2 | 11/2002 | Montanari et al. | |
| 6,974,796 B1 | 12/2005 | Girsh | |
| 7,074,894 B2 | 7/2006 | Walker et al. | |
| 7,147,882 B2 | 12/2006 | Girsh | |
| 2001/0048097 A1* | 12/2001 | Inui .................. | A01N 59/06 252/365 |
| 2002/0037295 A1 | 3/2002 | Lowell | |
| 2002/0058065 A1 | 5/2002 | Guivarc'h et al. | |
| 2003/0118653 A1 | 6/2003 | Chen et al. | |
| 2004/0156886 A1 | 8/2004 | Kose | |
| 2005/0260181 A1 | 11/2005 | Girsh | |
| 2006/0074051 A1 | 4/2006 | Girsh | |
| 2007/0014904 A1 | 1/2007 | Girsh | |
| 2007/0037777 A1 | 2/2007 | Girsh | |

OTHER PUBLICATIONS

Neocate Product Information Sheet, downloaded from www-shsweb.co.uk on Jul. 20, 2000, pp. 1-2.
Office Action dated Aug. 22, 2006 in U.S. Appl. No. 11/212,530, filed Aug. 26, 2005.
Office Action dated Apr. 12, 2007 in U.S. Appl. No. 11/212,530, filed Aug. 26, 2005.
Office Action dated May 21, 2008 in U.S. Appl. No. 11/212,530, filed Aug. 26, 2005.
Office Action dated Feb. 6, 2006 in U.S. Appl. No. 10/269,613, filed Oct. 11, 2002.
Office Action dated Jan. 11, 2008 in U.S. Appl. No. 10/765,664, filed Jan. 26, 2004.
Office Action dated Aug. 26, 2008 in U.S. Appl. No. 10/765,664, filed Jan. 26, 2004.
Office Action dated Jul. 1, 2008 in U.S. Appl. No. 11/073,514, filed Mar. 7, 2005.
Enig, M.G. "Fat and cholesterol in human milk" Wise Traditions in Food, Farming and the Healing Arts, a quarterly magazine of the Weston A. Price Foundation, Fall 2001, Dec. 31, 2001, pp. 1-3.
Office Action dated Jun. 6, 2008 in U.S. Appl. No. 10/868,697, filed Jun. 14, 2004.
Patt, H.M.et al. (1953) "Comparative protective effect of cysteine against fat neutron and gamma irradiation in mice" *Proc. Soc. Exp. Biol. Med*. Oct.;84(1):189-193.
Patt, H.M et al. (1950) "The effect of cysteine on the peripheral blood of he irradiated rat" *Blood* Aug.;5(8):758-763.
Straube, R.I. et al. (1953) "Studies with cysteinamine and cysteine in x-irradiated animals" *Proc. Soc. Exp. Biol. Med*. Dec.;84(3):702-704.
Patt, H.M. (1954) "Radiation effects on mammalian systems" *Annu. Rev. Physiol*. 16:51-80.
Patt, H.M. et al. (1953) "Radiation dose reduction by cysteine" *J. Cell Physiol*. Dec.;42(3):327-341.
Patt, H.M. et al. (1952) "Effect of x-rays on thymocytes and its modification by cysteine" *Proc. Soc. Exp. Biol. Med*. May;80(1):92-97.
Patt, H.M. et al. (1950) "Further studies on modification of sensitivity to X-rays by cysteine" *Proc. Soc. Exp. Biol. Med*. Jan.;73(1):18-21.
Konstantinova, M.M. et al. (1983) "The role of endogenous glutathione in the action of sulfur-containing radio-protectors" *Radiobiologiia* Nov.-Dec.:23(6):749-753.
Patt, H.M. et al. (1949) "Cysteine protection against x-irradiation" *Science* 10:213-214.
Hall, E.J. (1994) "The discovery of radioprotectors mechanism of action" IN: *Chapter 11, Radiology for the Radiologist*, 4$^{th}$ Ed., J.B. Lippincott Co., Philadelphia, PA, pp. 183-189.
Product Insert. Intralipid 20%® a 20% I.V. Fat Emulsion (Rev Apr. 2000) Baxter Healthcare Corporation, Clintec Nutrition Division, Deerfield, IL 60015 USA.
Office Action dated Oct. 9, 2007 in U.S. Appl. No. 11/073,514, filed Mar. 7, 2005.
Melichar, V. et al. "Nitrogen and fat balance studies and aminograms in low birth weight infants fed modified human bank milk" *Padiatrie and Padologie*, 1986, pp. 241-248, vol. 21, entire document with English summary.
Wattiaux, M.A. "19) Milk composition and nutritional value" Dair Essentials, Badcock Institute for International Dairy Rsearch and Development, University of Wisconsin-Madison, Sep. 26, 1997, entire document at web: www. babcock.wisc.edu/downloads/de/19.ed.pdf.
Martin, R. et al. "Human milk is a source of lactic acid bacteria for the infant gut" *The Journal of Pediatrics*, Dec. 2003, vol. 143, pp. 754-758.
Brooker, B.E. "The epithelial cells and cell fragments in human milk" *Cell and Tissue Research*, 1980, pp. 321-332, vol. 210.
Guerin-Danan, C. et al. "Milk fermented with yogurt cultures and lactobacillus casei compared with yougurt and gelled milk: influence on intestinal microflora in healthy infants" *Am. J. Clin. Nutr.*, 1998, pp. 111-117, vol. 67.
Meigs, E.B. et al. "The comparative composition of human milk and of cow's milk" *The Journal of Biological Chemistry*, 1913, pp. 147-168, vol. XVI, No. 1.
Office Action dated Jun. 9, 2005 in U.S. Appl. No. 10/752,298, filed Jan. 5, 2004.
Office Action dated Jan. 19, 2006 in U.S. Appl. No. 10/752,298, filed Jan. 5, 2004.
Office Action dated Jun. 28, 2006 in U.S. Appl. No. 10/752,298, filed Jan. 5, 2004.
Office Action dated May 25, 2007 in U.S. Appl. No. 10/752,298, filed Jan. 5, 2004.
Office Action dated Feb. 13, 2008 in U.S. Appl. No. 10/752,298, filed Jan. 5, 2004.
Campbell, J.K. et al. "Tomato Phytochemicals and Prostate Cancer Risk" *The Journal of Nutrition*, 2004, pp. 3486S-3492S, vol. 134.
Vanderhoof, J.A. "Probiotics: future directions" *The American Journal of Clinical Medicine*, 2001, pp. 1152S-1155S, vol. 73 (suppl).
Office Action dated Feb. 21, 2008 in U.S. Appl. No. 11/501,380, filed Aug. 9, 2006.
Office Action dated Nov. 18, 2008 in U.S. Appl. No. 10/868,697, filed Jun. 14, 2004.
Office Action dated Nov. 17, 2008 in U.S. Appl. No. 10/752,298, filed Jan. 5, 2004.
Office Action dated Jul. 28, 2009 in U.S. Appl. No. 10/765,664, filed Jan. 26, 2004.
Office Action dated Mar. 9, 2009 in U.S. Appl. No. 10/765,664, filed Jan. 26, 2004.
Lehninger, A. "The Molecular Basis of Cell Structure and Function" *Biochemistry*, 1970, p. 210.

\* cited by examiner

Cerebrospinal fluid showing metastatic breast cancer cells
Abnormal mitosis (mitotic figures) of cancer

| Type of aggregation Liquid crystalline phase | Geometry | Macroscopic character | Approximate HLB value | Surfactant parameter (V/al) |
|---|---|---|---|---|
| Micelles small spherical aggregates | | Clear solution | >13 | |
| Bilayer/lamellar phase | | Milky dispersion | 8-10 | ½ - 1 |
| Reversed hexagonal phase Rods of water surrounded by emulsifier | | Lumps of emulsifier in equilibrium with surplus of water | < 6 | |

FIG. 3

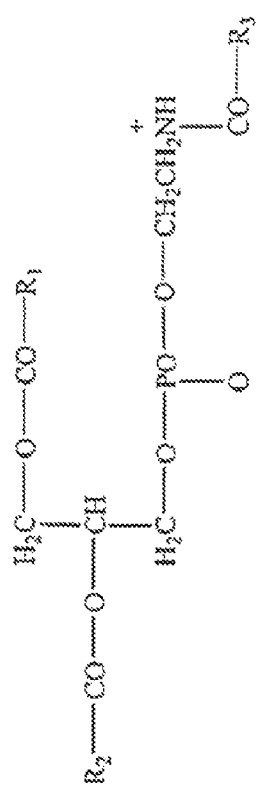
Phosphatidyl Ethanolamine (PE)
FIG. 5C
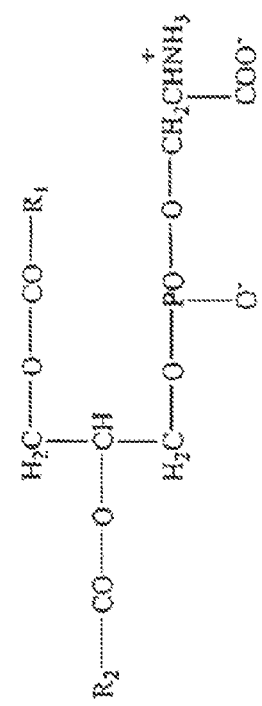
N-Acylphosphatidyl Ethanolamine (NAPE)
FIG. 5D
Subject composition components
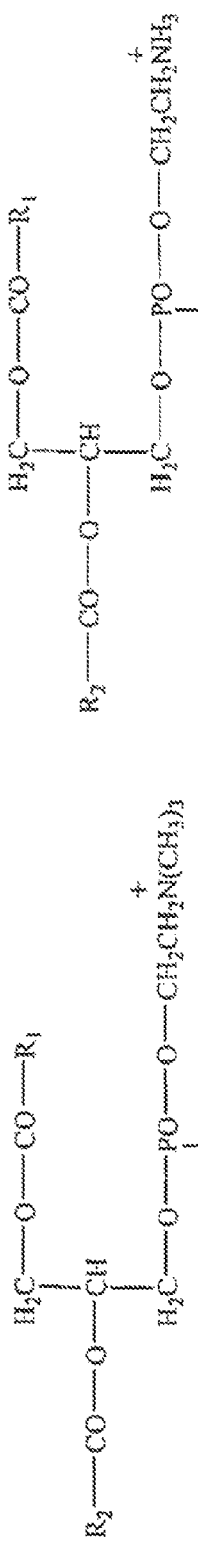
Phosphatidyl Choline (PC)
FIG. 5A
Phosphatidyl Sarine (PS)
FIG. 5B
Some phospholipids reported in plant seed lecithins

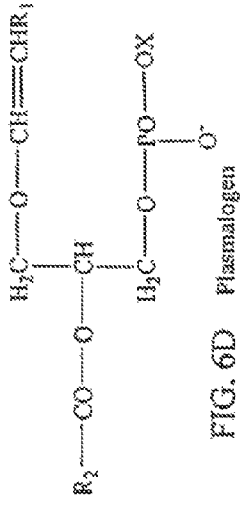
FIG. 6A  Phosphatidyl Inositol (PI)
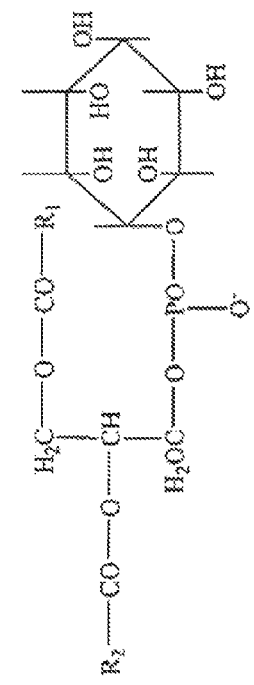
FIG. 6B  Phosphatidyl Glycerol (PG)
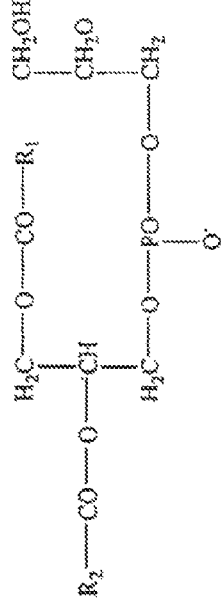
FIG. 6C  Phosphatidic Acid (PA)
FIG. 6D  Plasmalogen
X=Choline or Ethanolamine
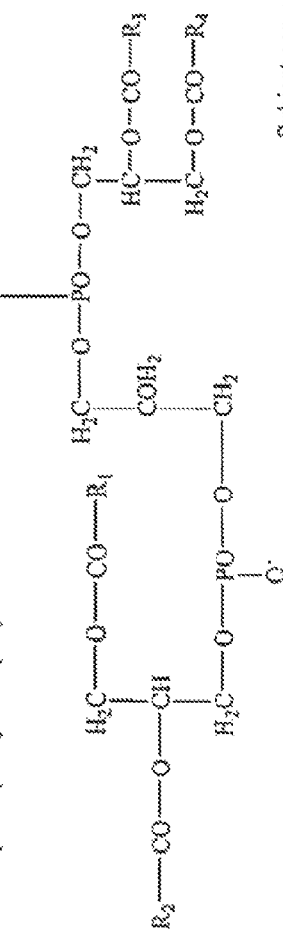
FIG. 6E  Diphosphatidyl Glycerol (DPG)
Subject composition components
Some phospholipids reported in plant seed lecithins Ibuprofen Fenoprofen Naproxen Ketoprofen Flurbiprofen

METHOD FOR REDUCING THE ALLERGENICITY OF ANIMAL DANDER

CROSS REFERENCE TO RELATED APPLICATIONS

This application is a continuation of U.S. patent application Ser. No. 11/592,530, filed Nov. 2, 2006, which is a continuation U.S. patent application Ser. No. 10/269,613, filed Oct. 11, 2002, now abandoned, which claims benefit of U.S. Provisional Applications 60/358,890, filed Feb. 22, 2002 and 60/350,119, filed Nov. 9, 2001.

This application is a continuation of U.S. patent application Ser. No. 11/592,530, filed Nov. 2, 2006, which is also a continuation-in-part of U.S. patent application Ser. No. 09/611,857, filed Jul. 7, 2000, now abandoned, which is a divisional of U.S. patent application Ser. No. 09/080,990, filed May 19, 1998, now abandoned, which is a continuation-in-part of U.S. patent application Ser. No. 09/058,469, filed Apr. 10, 1998, now abandoned, which is a continuation-in-part of U.S. patent application Ser. No. 09/058,430, filed Apr. 10, 1998, now abandoned.

This application is a continuation of U.S. patent application Ser. No. 11/592,530, filed Nov. 2, 2006, which is also a continuation-in-part of U.S. patent application Ser. No. 09/731,608, filed Dec. 7, 2000, now abandoned.

This application is a continuation of U.S. patent application Ser. No. 11/592,530, filed Nov. 2, 2006, which is also a continuation-in-part of U.S. patent application Ser. No. 09/639,859, filed Aug. 16, 2000, now U.S. Pat. No. 6,974,796, which claims the benefit of U.S. Provisional Patent Application No. 60/149,338, filed Aug. 17, 1999. Each of the above-referenced patents, patent applications, and provisional patent applications are hereby incorporated by reference in their entireties, including all figures, formulae, references, and tables.

DESCRIPTION OF THE INVENTION

The subject invention provides methods of inactivating pathogenic substances or producing immunogenic compositions containing pathogenic substances comprising contacting pathogenic substances, or compositions containing pathogenic substances, with super critical carbon dioxide or liquid nitrogen. In various embodiments, the pathogenic substances are inactivated and processed into immunogenic compositions.

Pathogenic substances for including in pathogenic compositions include microbial pathogens (e.g., pathogens of bacterial, prion, protozoan or viral origin). Alternatively, pathogenic compositions can contain pathogenic eukaryotic cells, such as cancerous, malignant, or tumorigenic cells. In another embodiment, pathogenic substances can be proteins, glycoproteins, lipoproteins, peptides, glycopeptides, lipopeptides, toxins, lipotoxins, lipopolysaccharides, carbohydrates, autoantigens, and/or tumor-specific antigens that cause pathogenic effects in individuals. Pathogenic substances may be attenuated microbial, fungal, yeast, protozoan, or viral (or viral-like prions) pathogens. Other embodiments provide for the inactivation of known live vaccine formulations typically used in current vaccination protocols. In yet other embodiments, virulent (non-attenuated) pathogenic organisms (e.g., microbial (fungal, yeast), viral, or protozoan pathogens) (or viral-like abnormal protein prion) are contacted with super critical carbon dioxide or liquid nitrogen and formulated into immunogenic compositions. In certain embodiments, the immunogenic compositions provide protective immunity upon administration to an individual. The subject methods are applicable to pathogenic substances of veterinary and human interest, including such problematic disease producing entities as the prion, e.g., a 30,000 molecular weight abnormal cell protein in neurons; abnormal beta pleated sheet isomer or isoform $P_R P^{Sc}$, which acquired relative resistance to digestion with proteases (a diseased conformation charge from normal alpha helix isoform or alpha helix isomer $P_R P^c$).

Liquid nitrogen cryogenic grinding (as with chocolate liquor or of beef, the potential bearer "vector" of prion induced mad cow disease) will produce a spatial isomer without reactive pathogenic components of prion. Liquid nitrogen cryogenic grinding of beef would be useful for the production of hamburger meat of the world-wide hamburger industry.

This non-reactive component, 30 kilo dalton structural re-isomerization, can be confirmed by comparison of normal, abnormal, and/or treated products in immunologic, biochemical, and/or other prion identification techniques, including, but not limited to, (1) RIA (Radioimmunoassay), ELISA, and IgE inhibition studies; (2) crystallographic studies of protein, as well as of amylose and amylopectin crystals (iodine stained, visualized with polarizing microscopy looking for change or absence of crystals after liquid $N_2$ or super critical $CO_2$ treatment. The allergic antibody can be looked upon as an IgE testing reagent against bovine protein, including beef. Allergic antibodies, in turn, can be used to distinguish between allergic reactions, prion-induced mad cow disease (bovine spongiform encephalitis (BSE)) and, from liquid nitrogen or supercritical fluid (such as $CO_2$) treated bovine protein (beef); (3) probe of protein structure using ultraviolet absorption and fluorescence property changes of protein using retinal binding as a test.

Contacting pathogenic substances, and compositions thereof, with liquid nitrogen or super critical carbon dioxide reduces or eliminates pathogenic effects of these substances and allows for their use in the formulation of immunogenic compositions. Compositions containing mixtures of two or more pathogenic substances can be treated with liquid nitrogen and/or super critical carbon dioxide and used in the formulation of immunogenic compositions.

The term "individual(s)" is defined as a single mammal or avian to which is administered a compound or composition according to the present invention. The mammal may be a rodent, for example a mouse or rat, pig, horse, ape, rabbit, goat, pig, cow, cat, dog, or human. Avian animals include, but are not limited to, chickens, pigeons, squab, turkeys. Alternatively, the compounds or compositions can be administered by way of animal or human food(s). In a preferred embodiment, the individual is a human.

The subject invention also provides methods of reducing the amount of low molecular weight pathogenic substances in a solution or composition comprising contacting the solution or composition with an ultrafiltration or filtration membrane that allows for low molecular weight substances to pass through the membrane filter while retaining other components above the filter. Low molecular weight pathogenic substances include toxins and other pathogenic substances such as prions. In some embodiments, the molecular weight cutoff for the filter is 1.0 kDa, 1.5 kDa, 2 kDa, 3.5 kDa, 10 kDa, or 20 kDa. Ultrafiltered compositions or solutions are substantially free of low molecular weight pathogenic substances. In some embodiments, the ultrafiltered compositions or solutions contain less than about 0.25 wt. % of low molecular weight pathogenic substances. Other embodiments provide for ultrafiltered solutions or compositions containing less than about 0.025 wt. % of low molecular weight pathogenic substances. Yet other embodiments provide ultrafiltered compositions or solutions containing no of low molecular weight pathogenic substances (i.e., 0.0 wt. %).

The subject invention also provides an immunopharmacologically engineered composition for reducing immunoinflammatory reactions commonly encountered with the use of cow's milk. The composition contains a tasteful milk (sheep's milk) that is produced utilizing specialized animal husbandry techniques applied to dairy sheep used throughout the world, such as Friesland sheep. The reactive antigenic factors responsible for the production of allergic diseases are reduced or excluded by excluding hypersensitizing cow's milk protein(s). This biologic process of elimination is functionally equivalent to inactivation of reactive pathogenic components by processing with liquid nitrogen or supercritical carbon dioxide or via processing by removing reactive pathogenic components such as, but not limited to, proteins by ultrafiltration with the option of replacement with nonreactive components. These non-reactive components include, but are not limited to, proteins designed to be free of reactive pathogenic components. Sheep are poor anti-human protein antibody producer compared to other animal, another protein ribosomal template reflection of non-reactive protein as found in sheep's milk.

These products are offered and assembled as molecular components of a cellular and tissue analog transduction and delivery system that signals cells and synergistically stimulates stem cell function. This pharmacodynamic function that the replication of normal tissue and in replacement of disease tissue (a function can provide for similar to normal tissue being replaced daily and/or turned over every two to three months). This is utilized in conjunction with the incorporation of anti-inflammatory activity and tissue healing factor(s) to be bonded, released, and function upon contact with the internal milieu of the patient. These biochemical components will signal the activity of replication and tissue repair healing in conjunction with anti-inflammatory activity. This signaling will induce automated robot-like therapeutic function and can be applied to problematic disease entities. It has been determined that sheep's milk and its products can serve as a concentrated source of L-amino acids and can be presented in a safe format, along with an equal percentage of sheep's milk protein, free of pathogenic reactive components of allergenicity to foreign protein.

Sheep's milk, human milk, goat's milk, and cow's milk, all contain lactose. Sheep's milk is 1% higher in lactose concentration than goat's milk or cow's milk; human milk is 1% higher in lactose than sheep's milk. As indicated below, about 99+% of tested subjects, intolerant of bovine milk, all tolerated lactose containing sheep's milk. Allergists expect milk substitutes not to be enjoyed and expect many complaints from patients. Unexpectedly, more than 80-83% of study participants experienced therapeutic benefit upon the substitution of sheep's milk for cow's milk. These individuals also expressed a preference for, and enjoyment of, sheep's milk.

It has been stressed in U.S. provisional patent application Ser. No. 60/149,338, hereby incorporated by reference in its entirety, that microorganisms, bacterial, and microorganisms (bacterial, viral, yeast, and fungi), microorganism derived metabolic products, as well as microorganism-like prions can act as bacterial hypersensitizers in producing allergic disease along with their infections potentiating disease factors. Milk has yet to be shown to transmit the causative agent of BSE to humans or another consumer of the milk.

Another potential cause of allergic response can be eliminated by using the by-product permeates of mammalian milk and such productions as for cheese manufacturing. Disease spread by older animals, and who also have the lowest phospholipid content, suggest the elimination of older dairy cattle, e.g., lactating even at 20 years of age. It is the older animal that is susceptible to BSE. This subject therapeutic composition includes phospholipids such as phosphatidylcholine in treating this deficiency of aging.

It is noteworthy observation that dairy sheep farms in the above study do not have silos. That is because ensilage eaten by sheep would bring about an infection such as, but not limited to, clostridial or listeria, apparently not a concern in dairy cattle. However, up to 40 percent of dairy cattle had been observed to have ileitis (Johne's Disease in ruminants) and have to be sacrificed yearly. Johne's Disease might possibly correspond to the ingestion of ensilage with fermenting aging corn husks and as in humans might also be characterized by high levels of serum antibodies to brewers and baker's yeast (*Saccharomyces cerevisiae*). Humans with ileitis (Crohn's Disease, the human equivalent to Johne's Disease, is characterized by high levels of serum antibodies to brewers and baker's yeast (*Saccharomyces cerevisiae*) and Disease) are also highly allergically intolerant to cow's milk. Sheep and goats only have a one percent incidence of ileitis (Johne's Disease). Sheep's milk offers the highest percentage of butyric acid fats, helpful in healing inflamed intestines as in ileitis.

Sheep's milk has high butyric acid content. Sheep's milk contains about 2% more butyric acid than cow's milk (about 5.5% vs. 3.5%) Butyric acid levels are believed to be helpful in healing Crohn's Disease. Ammoniated butyric acid is valine. I have also found that another short chain deaminated aliphatic L amino acid 2 carbon 50% acetic acid will dramatically reverse long-term dermatitis and, fungal infection of the toe nail, even with significant damage to the nail, following brief periods of application of the acetic acid. The acetic acid represents the deaminated glycine in this subject composition can be applied one to seven days per week and can be applied multiple times in one day. The duration of application can range from 2 to 60 minutes (or any other chosen interval) per application. This treatment protocol is particularly useful in patients allergic to standard anti-fungal agents used in the treatment of fungal infections.

Sheep's milk also contains significant amounts of amino acids useful in the manufacture of yogurt by bacteria, such as, but not limited to, *Lactobacillus* spp. Additional amino acids are also produced in yogurt production. As a result, most Crohn's Disease patients intolerant to cow's milk, tolerate and benefit from dairy products produced from sheep's milk, such as yogurts, sheep's milk, and yogurt ice creams and yogurt ice creams or yogurts produced from cow's milk. Thus, the subject invention provides compositions suitable for the treatment of gastrointestinal disorders, such as ileitis, milk allergy, Crohn's Disease, and IBD (inflammatory bowel disease), comprising the administration of sheep's milk or dairy products derived therefrom.

I have found that patients with milk allergies, milk intolerance and inflammatory bowel disease (IBD), such as ileitis (Crohn's Disease), tolerate yogurt much better. This conforms to the present invention in that yogurt has free amino acids of tyrosine, phenylalanine, and leucine, which constitutes more than half of the amino acids present; proline is also present. *S. thermophilus* peptidase initiates the proteolysis of casein. The greatest amount of free amino acid is produced with an equal bacterial amount (1:1 ratio) of *Lactobacillus bulgaricus*, concurrent with incubation and cooling. Therapeutic benefit is also derived from the anti-inflammatory healing effects of essential fatty acids (e.g., omega 3 and omega 6), via production of anti-inflammatory prostaglandins PG1 and PG3 (without stimulus for production of inflammatory protoglandins PG2); also, avoidance of trans fatty acids which block delta 6 desaturase enzymes and inflammatory prostaglandins provides therapeutic benefit. Thus, compositions for the treatment of milk allergies, milk intolerance, and IBD can also contain essential fatty acid fats. The monounsaturated fat in olive oil is very resistant to oxidation, and is useful in preventing free radical oxidation and initiating inflammatory prostaglandins.

The gastrointestinal healing effect of medium chain triglycerides (C6-C12) in coconut oil (also, natural butyric $C_4$ acid); a fraction of butter (advantageously, butter that is hypoallergenic) can also be added to further this healing effect. Additionally, medium and short chain fatty acids, independent of liver involvement in processing long chain fats and fat storage, can be added as a quick energy source, and are also somewhat water soluble increasing hydrophilic state and HLB.

The subject invention, in addition to the therapeutic component stressed here, also provides for the correction of abnormal blood levels of nutritional factors; (e.g., amino acids, essential fatty acids, mucopolysaccharides, vitamins, and minerals); these abnormalities may be due entirely to disease and complications (e.g., gastrointestinal loss of nutrients in illustration of ileitis), and risk factors of long term medications, such as corticosteroids, and prior poor nutritional habits including trans fatty acids (s in oleomargarine), which block enzymes, such as delta 6 desaturase, to produce anti-inflammatory prostoglandins (in contrast to most inflammatory PG2) and add to arteriosclerosis.

It would be advantageous to employ computer software, produced by the pharmaceutical companies developing these products, that can further individualize and maximize actions in production of elemental free L amino acid rich formulation analogs to normal tissue now diseased tissues. These formulations are specifically made for a multiplicity of severe illnesses, acute and chronic manifestations, and morbidity, mortality, and risks of medication that must be carefully considered along with severity of illness and achievable therapeutic benefits, in contrast to a therapeutic trial of free L amino acid low risk elemental formulations in the context of this invention.

In the aging process, where the production of digestive enzymes (to make free L amino acids) and growth hormone are diminished, the free amino acids of the inventive non-invasive therapeutic composition are anabolic and stimulate production of growth hormones, both of which are beneficial. Thus, the subject invention provides methods of treating conditions or symptoms associated with aging comprising the administration of compositions taught herein.

Sheep's milk contains (w/w) greater than about 5% amino acid. When all twenty amino acids are considered, the percentage is in excess of 6% (w/w). Sheep's milk, at 7% fat (and containing a significant percentage of short and medium chain fatty acids), has the highest levels of fat of domestic mammalian milks. This is important in healing diseases, such as the chronic granulomatous illeal lesions of Crohn's Disease, and possibly keeping the bowel surface normal with and minimizing or avoiding the uptake of allergenic food protein. This can also minimize food sensitization and food allergy.

The subject invention also provides an oral delivery system, chylomicron mediated, with special application to vaccine administration. This oral delivery system is also useful for the delivery of other orally administered drugs, such as insulin.

The oral delivery system of the invention comprises a chylomicron vehicle, typically of 0.5 to 1 micron in size. The chylomicrons can be made according to methods well known in the art. By way of example, one component comprises palm kernel oil and coconut oil. This component comprises ⅔ of the composition and contains 40% palm kernel oil and 60% coconut oil. The other ⅓ of the composition comprises corn oil. These materials are mixed together and warmed to approximately 110-120° F. 100 ml of the liquid fat is combined with one or more surfactants and the mixture is used to suspend an antigen or drug. Surfactants useful in this aspect of the invention include PGPR (polyglycerol polyricinolate; 0.3% of the final product), PC (phosphatidylcholine; 0.15 percent of final product), glycerine (U.S.P. 0.5 percent of final product), and Tween 80 (polysorbate 80; 0.3 to 0.5 percent of final product). The final liquefied suspension can be emulsified with the use of a homogenizer, e.g., Manton Gaulin 3 to 8000 psi instantaneous processing, and was emulsified by a colloid mill. The particles' size was in sample production and can be confirmed by microscopy and can be between about ½ and about 1 micron in size using size standards known in the art. For example, the oral delivery system described above has been used to deliver urease, an antigen not encountered by poultry to poultry (provided at 50 mg/pound). A soft fat can be used to permit prolonged residence, in the oral cavity, for oral mucosal absorption. Antigen delivered via this system induced an antibody response equivalent to that produce by standard injection of antigen. By feeding the antigen delivery system described herein after fasting chickens for 2 hours (chicken store ingestants in gullet for prolonged time as a fasting defense), antibody level was equal to injectable response. This also appears to be an additional breakthrough in acquisition of oral tolerance (not usually seen in avian species as chickens).

Sheep's milk can also be augmented and extended to cover other bacteria, sheep could serve as a convalescent serum or a low allergenicity therapeutic composition.

The oral delivery system can also be mixed with flavoraids, such as those described in U.S. Pat. Nos. 6,197,356; 5,912,040; and 5,753,296, and provisional application Ser. No. 60/149,338, each of which is hereby incorporated by reference in its entirety. Chocolate, white chocolate free of caffeine and theobromine, can be used to incorporate a synergistic flavoring and savoring mechanism delivery system to maximize mucous membrane absorption. An ideal delivery system for a medication such as a specifically prepared stem cell stimulant anti-inflammatory stem cell and tissue healing therapeutic agent is included in one of the embodiments. Here the sheep milk with six percent free L amino acids may optionally constitute the milk composition of milk chocolate. L amino acid concentrations can be further heightened by probiotic yogurt treatment which would enhance the level of amino acids even further. Also useful for the delivery of vitamins and minerals, it has been noted that the dairy animals with the highest concentration of L amino acids in their milk have the highest body temperature. This enhances probiotic temperature of the heat loving or thermophilic microorganisms such as, but not limited to *Streptococcus thermophilus*, which is used in one-to-one concentrations in conjunction with *Lactobacillus bulgaricus*. The highest L amino acid concentrations are found in sheep and goat's milk (the highest in sheep's milk) with highest temperatures of about 102 degrees Fahrenheit rectal temperature. Human rectal temperature is 99.6° F. in contrast to bovine rectal temperatures of 101.5° F. The chicken's temperature is even higher at 107° Fahrenheit (rectal temperature).

A stem cell formulation based upon an extrapolation from a life model about the origin of life was a formation of the first cell, in which polymer chains of at the least two of three types now represented/used here by free L amino acids (an analog of human cellular tissue proteins), nucleic acids (DNA), proteins, and a semi-permeable membrane comprising phospholipids, lipoproteins, and glycoproteins which orient vesicle formation of a surrounding cell membrane. These vesicles can be further surrounded by extracellular matrix mucopolysaccharide.

I have found that the biochemical pathogenic reactive components appear in disease in many formats but can be exemplified in microorganisms and microorganism-like substances including virus and prions. The primary disease factor here seems to be the foreign proteins which include the lipoprotein, and lipopolysaccharide (LPS), the essence of the tuberculin test, as well as toxic shock disease and bacterial cell membranes (for Gram negative bacteria).

The proteins may be modified by extremes of biophysical processing such as temperature cracking (similar to the fractional distillation of petroleum). In the case of the protein polymer, the most hydrophobic (lipophilic) amino acid components are located within the center of the molecule. Differences in freezing points and melting points in the case of submerging for treatment with liquid nitrogen at a temperature of −320 degrees Fahrenheit place great stress upon the molecule with resultant cold denaturation and a 3-D configurational change in the spatial appearance of the molecule. Similar effects may be noted with supercritical carbon dioxide processing.

Natural processing of sheep's milk proteins results in a protein that does not require the above specialized food processing therapy, since our current study in 199 patients, who were allergically intolerant to cow's milk, showed this milk to be about 99 plus percent efficacious as a hypoallergenic substitute for cow's milk. Our current study shows a very high acceptance rate of about 83 percent for sheep's milk. This is in contrast to acceptance rates of 35 percent for other milk substitutes such as soy, and goat milk. Similar acceptance rates were seen with rice almond and oat substitutes. There was about 90 percent tolerance for goat's milk, and about 95 percent tolerance for soy milk; however, in the U.S. I have found poor success with goat's milk (as a cow's milk substitute). This may be due to the heat treatment or pasteurization of canned goat's milk which may alter it from its natural state or condition.

This naturally hypoallergenic protein is present at about six percent, and the amino acid "pre-protein" which also may be referred to as bioaminenergic or bioamine are available in a similar about six percent level in this especially available and prepared foods as the sheep's milk and to attain this level of hypoallergenicity the above additional processing is not necessary.

It is noteworthy, with the stem cell growth factor observed with L amino acids, that the sheep is the only animal where a successful clone has been biologically accomplished.

The naturally occurring endorphins, dynorphans, enkephalins family of endogenus morphine-like opioid compounds have 31 amino acids. The use of L amino acid analogue composition, comprising similar molar ratios of free L-amino acids to these 31 amino acids of 91 amino acid precursor polypeptide compounds, would be expected to have a similar analogue activity. Patients with narcotic drug addiction have lower blood levels of amino acids. This composition and it use would also obviate morphine side effect of enhancing the dissemination of cancer, as well as increasing prolactin which also enhances the dissemination of breast and prostate cancer.

The use of hydrophilic surfactants with a high HLB approaching 20 such as Tween 80, phosphatidylcholine (PC) with an HLB of 13, as well as the L amino acids, and butyric acid compounds (the C6, 8, and C10 carbon fatty acid fats) would be expected to help kill bacteria, attack the protein lipopolysaccharide endotoxin of bacteria including the gram negative bacteria, to help enhance antibiotic sensitivity. Other compounds that have such activity also have a similarly lethal effect on cancers cells. The mode and rationale for discovery and use of heavy metal platinum (also bactericidal) in treatment in killing cancer cells. This has a high level of side effects. In addition, mitosis seems to also be incorporating and concentrating phospholipids such as PC of the cellular and nuclear membrane components in its genetic activity. Hydrophilic surfactants with high HLB of 18 Tween 80 polysorbate 80 (of 20=$H_2O$), and other hydrophilic surfactants which include sodium lauryl sulfate with a high HLB of 20, free of side effects, along with PC with HLB of 13; and seem to have effects of similar hydrophilic hydro-colloid activity that stimulates the reversal of mitosis. See Figures I, Ia, II, & III.

Figures I, Ia, II, and III are suggestive of similar biophysics: it was observed here, that the morphologies of mitosis were uniquely, highly similar to the biphasic diagram of hydrophobic reversed hexagonal biocolloid surfactant geometric patterns.

HLB effect is additive and use of PC, deficient in this aging population prone to cancer, would be important to include in HLB modulation. It seems likely that the overly reactive mitosis seen in cancer is the body's compensatory mechanism responsive to this PC and high HLB deficiency. Particularly in our current societal habit of excessive fat and sugar consumption without appropriate and proportionate hydrophilic HLB modulation. This PC deficiency may also better explain why cancer and atherosclerosis commonly occur, and occur together in this aging population and why atherosclerosis (including its effect in coronary disease) and other diseases of aging (e.g., arthritis, memory and mentation loss, onset of Type II diabetes mellitus, hypertension, and obesity associated with poor eating habits [excessive fat and sugar ingestion] and a sedentary lifestyle), would also be amenable to same hydrophilic HLB modulation.

It is likely that drugs such as, but not limited to, aspirin, particularly as used in this subject composition, are mediating their activity through some increase in HLB (through specially bonded formulations in these embodiments and subject composition or in internal milieu bonding in these embodiments and subject composition).

Yogurt like microorganism probiotic production probably accounts for this record amino acids level in that one of the highest levels was L amino acid, leucine 0.59 gram percent. The other L amino acids characteristic of (*Streptococcus thermophilus*) and *Lactobacillus bulgaricus* microorganisms of yogurt production phenylalanine, tyrosine and proline also were present in these milk products. Cyclosporin analog L amino acid in utility patent also are present: Glycine, valine, alanine, leucine and its isomer isoleucine as evidence of anti-rejection stem cell activity, without complication of rejection like allergic reactivity problematic in cow's milk, and goat's milk. Since the temperature of maximal function of *lactobacillus* is to 37 degrees to 45 degrees C., it is possible that the heat loss must be considerably less, and therefore possibly higher body temperature in the sheep (39 degrees+C.) with its uniquely characteristic insulated wool "coat" fostering greater *lactobacillus* L amino acid productive activity (rectal temperature 102° F.).

We are what we eat, and our food chain represents a similar reflection. This is best exemplified by the omega 3 EPA fatty acids of fish, whose production is dependent upon the ingestion of algae, which may not be present as a source of food for fish in a fish farm like program. Also, considerations applicable to natural biologic activity of subject composition sources of a stem cell stimulant therapeutic composition and medication.

It might be considered that the HLB number obviously has to be related to the surfactant parameter (V/al) which describes the actual geometry of the molecule. Consequently, the HLB-value may also be roughly estimated from studies of the solution properties of the emulsifier, which basically is a very simplified way to determine the phase diagram. In this way, qualitative information on how salt, sugar, pH, alcohol and temperature influence the effective HLB value of the surfactant can be obtained.

The relation between the aggregates formed, the geometrical shape of the spatial 3-D comparative proteins of milk production (performed by comparative protein crystallography), surfactant (and its manifestation), the macroscopic character, the HLB number, and the surfactant packing parameter. The macroscopic character refers to a 5% mixture of the surfactant in water (comparative Dü Nouy tensiometry and phospholipid lipoprotein glycoprotein concentrations are important).

A study of 206 individuals, 195 of whom were intolerant to cow's milk (11 were tolerant to cow's milk) demonstrated the advantageous nature of using sheep's milk for treatment of food allergies due to cow's milk, a common cause of food allergy, and symptoms associated therewith. These individuals listed other offensive dairy products (containing cow's milk) such as custard, chocolate, yogurt, milk puddings, butter, cheese, cream, and ice cream. Symptoms noted most frequently were diarrhea, nausea/vomiting, headache, irritability, stomach ache, bloating, skin rash, eczema, nasal congestion, migraine, hyperactivity (in childhood).

Of the 206 participants in the study, tolerance of sheep's milk was near unanimous; 99% tolerating sheep's milk with 83% preferring it. Other comparable milk substitutes, during the initial comparative trial period, gave responses preference to cow's milk of approximately 35%, leaving sheep's milk as the product most relied upon in this one year observation study. It is remarkable that the multiplicity and severity of allergic symptoms produced by cow's milk were relieved by the simplistic substitution of Sheep's milk. Other time honored comparative substitutes, (during the initial trial period for each participant), were much less satisfactory, averaging 35%. The presence (found in all mammalian milks) or absence (in non-animal milk substitutes) of lactose did not appear to be a factor. Additionally, it should be noted that commercially produced reduced lactose milks are treated with enzymes, such as lactase, and may have undergone modification of glycoproteins found in the milk when lactose is split off from the protein.

| COW'S MILK SUBSTITUTES | | | |
|---|---|---|---|
| SUBSTITUTE | TOTAL PATIENTS | # TOLERATED | PREFERRED |
| Sheep | 199 | 198 | 164 = 83% |
| Soya | 101 | 95 | 39 = 38.6% |
| Goat | 92 | 90 | 30 = 32.6% |
| Rice | 50 | 50 | 17 = 34% |
| MISCELLANEOUS SUBSTITUTES | | TOLERATED | PREFERRED |
| Oats | | 11 | 3 |
| Coconut | | 4 | 2 |
| Almond | | 1 | 1 |

Clinical symptoms typically seen with cow's milk allergy include:
1 Colic to 3 months,
Eczema (asthma of the skin),
3 months to 3 years
Bronchial asthma,
2-3 years onward
Patient is admitted to the emergency room, age 20 with asthma; roll up sleeves and observe eczema. Possible lifetime stigma of cow's milk allergy. Stop milk and asthma can be relieved.

Example II

Of a group of 73 participants (in total of 206), all now on sheep's milk, showing improvement of symptoms, 35 reported almost instant improvement of symptoms and 26 reported a gradual improvement of symptoms. Five reported a combination of instant and gradual improvement of symptoms. Incomplete answers were provided by 7 participants.

Most common other offending foods (other than dairy which was 100%) were chocolate 79 (of 133), wheat 37 (of 133), and beef 30 (of 133). Four breast feeding mothers noted the disappearance of their infant's colic, almost instantly, when the mothers discontinued ingestion of cow's milk and dairy products, and used sheep's milk as a substitute (emphasizing how milk can be a vector for foreign proteins ingested by a lactating mother, either human or animal [e.g., cows]). I have also been able to alleviate symptoms associated with arthritis and joint pain by eliminating milk (cow's milk) and beef from the diet of subject. This observation has been extended to other chronic arthritis patients (i.e., the elimination of cow's milk or beef from their diets. This observation can be used to salvage large numbers of patients that require joint replacement.

| MORE SPECIFIC DIAGNOSES (133 of the Participants) | |
|---|---|
| Eczema/Rash | 29 |
| Diarrhea | 29 |
| Irritable Bowel | 15 |
| (includes colitis and Crohn's Disease) | |
| Arthritis/Joint Pain | 21 |
| Asthma | 21 |
| (includes breathing problems) | |
| Migraine | 18 |
| Dyslexia | 9 |

Detecting causal factors of dyslexia can be illustrated as follows: Two brothers whose parent, a teacher, noticed changes in behavior after the ingestion of milk further noted changes in handwriting after the ingestion of milk or milk products. By daily charting of handwriting it was possible to note the deviation from diet correlating with behavioral changes and induced learning disabilities. One child became dyslexic and the other child developed phonetic spelling (manifested in the reversal of the letter L (to ]) and 9 (to P)) and could not follow the lines on the page.

The art and science of chocolate manufacture continued to be dependent on a very labor intensive and training and technological know how of the conching process, time and temperature of lipid, phospholipid, and emulsifier complex chemistry with this sophisticated technology and expensive equipment for conching that is available to primarily, the very few but very large, multinational chocolate companies. It is not known that PGPR can reduce conching time of non Newtonian chocolate by reducing or overcoming inertia biochemically and biophysically, whereas, it is primarily and essentially mechanically as in the case of the conching of chocolate.

This invention makes possible for other companies with very limited, if any, chocolate conching facilities to receive chocolate shipped in a 40,000 pound tanker or as 5 to 10 lb. blocks into a very large melter tank (e.g., 2,000 pounds) and by adding an agitator or recirculator along with 0.3% PGPR (similar concentration of lecithin added 0.3 percent) this combined effect of several hours or more and mixing would bring about the flavor development of the best grade chocolate, whereas the time-honored technique of adding emulsifier and/or surfactants has been confined to the highly expensive labor-intensive conch.

A great economic saving and improvement in quality would result with net decreasing: (1) conching time concomitant with (2) the dependency on expensive cocoa butter for functionality of hollow molding, molding and demolding, (3) varieties of sourced products to meet marketing needs versus one base product with the only adjusted variable being PGPR, (4) the need for increased particle size to 50 microns at a sacrifice of good mouth feel, good taste, and good eating qualities. Regardless of which of these goals is desired, all result when melting is performed on a conched shipment of chocolate to such intermediate size companies in preparation for final use.

I have unexpectedly, and repeatedly, observed a dramatic reduction in viscosity when the last ½ of lecithin is routinely added to this very viscous chocolate ½ hour prior to completion and prior to beginning to conch. This observation has been made in all types of conches, Frisse, McIntyre, Ball.

Within a short period of time, the chocolate suddenly becomes very liquid without this viscosity reduction and sloshes about the conch for a definitive and finite time of only a few minutes. Then, most of this dramatic viscosity reduction is lost forever in this product.

This same, but more lasting, observation has been made with a highly efficient emulsifier surfactant PGPR (polyglyceryl polyrininoleate) and an improved version of PGPR (0.3 percent), available commercially. It is not known to the art that this same entity can be observed with PGPR. This same liquefying viscosity reduction effect lasts several hours even days and can be used to minimize the need for conching and the need for adding additional costly cocoa butter to chocolate for 70 to 90 (85 MacMichael hollow molding chocolate). It has been observed that 6% more cocoa butter is required when PGPR has not been added to the material (28-29% with PGPR versus 34% or more cocoa butter added without PGPR). Plastic molds must be used, for molding and enrobing chocolate, chocolate viscosity adjustment to 120-140 MacMichael permits the company to derive from one order of good quality 190 MacMichael (20 micron 28-29% cocoa butter fat chocolate) and with the addition of 0.3% PGPR to several thousand-pound batches of chocolate pre-made by a supplier and produced very good quality Standard of identity chocolate with finess of 20 microns (vs. 50 micron . . . fair quality chocolate [produced with 35-35% cocoa butter fat] and both produce 70 to 90 MacMichael viscosity chocolate simplifying plant production. Only one type of base chocolate is required by adding less PGPR (e.g., only 0.15% enrobing or molding chocolate will result in adapting to many orders) and can be tested as Standard in a MacMichael viscometer.

Once a chocolate sets with this PGPR (0.3% or 0.15%) dosage, the lowered viscosity functionality workability of 70 to 90 MacMichael is partially lost. In that remelting after 3-4 months of storage provides a viscosity of 120 is still a significant improvement over the original viscosity of 190 to 200 MacMichael, and has retained most factory functionality of enrobing and molding.

The viscosity of PGPR is increased to 0.5 percent, or even to one percent, the viscosity is progressively decreased so that hollow molding chocolate will allow the presence of more medication as in the above embodiment without disturbing viscosity in regard to pipe flow in the factory. Also, an equal amount of dry blend of sugar and cocoa (may also be processed with ambient gas as in this embodiment). This one percent PGPR chocolate would be functioning tantamount to a chocolate super solvent and a standard identity chocolate or a technically simpler compound coating chocolate (not requiring tempering) simplifying the steps of providing the above embodiments without the tedious, technical skill, labor-intensive requirement of conching. Such one percent PGPR chocolate composition would result in a reduction of fat from 28-29 percent to 14 to 15 percent with the option of adding 1-2 percent Salatrim fat to nutritionally further reduce calories from fat by another percentage as well as protecting the chocolate when shipped in terms of resistance to melting that I have unexpectedly observed. Enrobed salatrim chocolate is several times more resistant to melting with all day exposure to an 100 to 120° Fahrenheit temperature. When returned to an air conditioned temperature of 76° F., the somewhat softened chocolate returned to its prior molded state. Non-salatrim chocolates did not return to their prior molded format and fat separation (bloom occurred).

Another vehicle to dispense the therapeutic stem cell composition is in the form of an instant soda fountain chocolate soda using supercritical fluids, such as $CO_2$, or liquid Nitrogen treated cocoa or chocolate. The treated chocolate/cocoa is cryogenically ground and can be flavored with a natural or artificial flavor, such as citric acid, cherry, orange, grape, banana, chocolate cream, or other flavors. Vanilla (0.1% to 0.15% total [volume to volume]) and/or granulated sugar can also be added. Other sweeteners such as saccharin, aspartame, or other known sugar substitute sweeteners can be used if lower sugar content is desired. The addition of 6-8 ounces of seltzer or soda water to these vehicles results in a flavorful product suitable for the administration of medication. These vehicles are used to pleasantly deliver medications to pediatric or geriatric patients.

The subject application also provides, as a functional biochemical composition, primordial biochemical components of progenitor cells and tissue comprising:

a) one or more cell membrane components, such as phosphatidylcholine (a biophysical membrane cell membrane formative factor with intrinsic predisposition to cell membrane vesiculative formation, and also a very efficient delivery system) or other known phospholipid/fatty acid/sterol components;

b) L-amino acids (free) that enable reversible healing of damaged tissue—and/or excellent graft and/or organ acceptance (if not otherwise preventable by the synergistic use of a and c); and c) one or more extracellular matrix mucopolysaccharide compositions (to further support progenitor stem cells which can, optionally, be additionally latticed/scaffolded with mucopolysaccharide for in vitro or in vivo use).

If required, the heart valve vascular lattice can be supplemented with the embryologic structure and biochemical components of umbilical cord(s), including, but not limited to, mucopolysaccharide and surfactant components including, but not limited to, phospholipids, sphingomyelin, sphingolipids, glycosphingolipids, gangliosides (such as those gangliosides which are primarily located on the outside surface of mammalian cell plasma membranes and responsible for cellular and intercellular adhesion, differentiation, and migration mechanisms). Their components include fatty acids mainly stearic, hexoses of glucose and/or galactose, L galactosamine, and sialic acid. Cell signaling may be utilized in valvular and vascular cell culture and grafting as exemplified by the anti-prostaglandin affect of aspirin in the correction of a patent ductus arteriosus. If other congenital heart defects are present, such as an obstructed pulmonary or aortic valvular system, patent ductus arteriosus may be maintained by the administration of prostaglandin E (the functional anti-thesis of aspirin). Similar cell signaling treatment, as incorporated in this subject composition, in conjunction with medication such as, but not limited to, aspirin or specially bonded medication in these embodiments, e.g., but not limited to, aspirin or internal milieu bonded compounds associated with the use of subject composition, may be utilized in the management of congenital heart disease in vitro, or in vivo.

Sialic acid residues and glycoprotein are the main cause of cell surface negative charge. Substances of elasmobranch origin derivatives (with high index of acceptance and readily established oral tolerance) can be added to heart valve and vascular structures and may also be included if required.

The earliest primordial origin of these components, even prior to stem cell differentiation, can be exemplified by plant thallophyte differentiation into stem, leaf, and root and might be referred to as a merocyte or stalk (in contrast to the differentiated stem) cell biochemical component.

These foregoing components, in the practice and medicine and pediatrics, can be looked upon as potentially rejection resistant and are not subject to hypersensitivity reactions. In fact, protection can be further reinforced by a unique oral tolerance mechanism.

The subject composition and its stimulant action in cell signaling can be used therapeutically in conjunction with other medication (and particularly synergistically with other medications to therapeutically add to maintenance, repair, and reversal to normal of cellular membrane leaks and damage to cell membrane involved in the pathogenesis of disease. This adds, to the patient's damaged cells and cellular debris, building blocks for reconstitution of the cell. The destruction of cell membrane and extracellular matrix is the modus operandi of a spectrum of various diseases (such as bacterial or viral infection and degenerative diseases (which include diseases of aging, arthritis (osteoarthritis), rheumatoid arthritis, lupus autoimmune damage, arteriosclerosis, coronary artery disease, diabetes, mellitus, hypertension, Alzheimer's disease, as well as all the compendium of diseases including, but not limited to, that found in the reading medical, pediatric, and immunologic texts)).

Additional available methyl groups can be derived from phosphatidylcholine to counter any homocystine or homocysteine predisposition that might aggravate the inflammation present in the pathophysiology of atherosclerosis and coronary artery disease.

The concurrent addition of this subject composition or any of its components to medications additionally furthers synergism by countering the long and the short-term toxicity, side effects and/or metabolic risks of such drugs and therapeutic agents such as, but not limited to, aspirin and nonsteroidal anti-inflammatory drugs in treatment protocols. Specifically, aspirin reduces phospholipids such as phosphatidylcholine along with reducing the cell life, e.g., of the erythrocyte.

The subject compositions are also useful in countering disease by providing barriers to the spread of infection, inflammation and metastasis of cancer (such as the mucopolysaccharide basement effect membrane so helpful in countering the metastasis of cancer). All tissues and organs requiring normal mucopolysaccharide basement membranes, as well as mucopolysaccharide integrin, and cadherin offering cell adherent function, as well as immunologic protective effect in antibody associated cellular immunity can benefit from the compositions of the subject invention.

This foregoing significant pharmaceutical synergism (with utilization and co-utilization of said therapeutic composition) is further synergized by its component lipid and phospholipid, such as phosphatidylcholine. Surfactant delivery systems, enhancing the dissemination of these therapeutic pharmaceutical components, as well as the subject composition also synergize the subject compositions.

This subject composition and/or its components can be further synergized by chemically bonding reactive chemical groups such as, for example, the acid carboxyl group in such treatment medications as aspirin, by esterification of lysolecithin (biochemically formed by the phospholipase A2 deacylation treatment of such surfactant lipid-phospholipids as phosphatidylcholine exposing the alcohol OH group or sulfasalazine (already bonded to aspirin) resulting in a pharmacodynamic small molecule that may be better utilized alone or in conjunction with the therapeutic composition of the subject invention. In the ester formation, water was split out, concurrent with the bonding of an alcohol with an acid group, in the present of a catalyst, such as nickel or zinc, which, of course, is usually removed at the completion of processing. The selection of aspirin, for example, as a bonding moiety synergistically adds its pharmacologic anti-inflammatory, analgesic, anti-atheromatous clot formation, anti-cancer activities to the chemical composition of the subject invention. Therapeutic compounds, such as aspirin, can also be bonded to mucopolysaccharides, collagen, cartilage, and/or chondroitin sulfate through available hydroxyl groups. This bonding can also be a peptide bonding, e.g., the acetyl group of aspirin to the $NH_2$ group of e.g. glucosamine. An added synergistic feature—In the case of arthritis, these chemical bondings to these mucopolysaccharides offer an added tropism and affinity to the inflamed arthritic joints.

The alcohol group in sphingosine of sphingomyelin or the glycosphingolipids (as well as the carbohydrate such as the OH on the glucose group) could also be available for these chemical bonding opportunities in the preparation of therapeutic agents.

An anti-inflammatory variant of the essential fatty acid linoleic acid can also be provided in the subject composition.

The extreme reactivity of double bonds, for example, the essential fatty acid fats, linoleic acid and linolenic acid, in this subject composition and particularly the isomer, conjugated linoleic acid can be further utilized here alone or in combination with the subject composition, by chemically bonding the acid acetyl or COOH group of aspirin to further augment this anti-inflammatory activity of aspirin and conjugated linoleic acid reactions.

This strategy can be expanded further by bonding pharmaceuticals (such as, but not limited to, aspirin to procaryote surfactant phospholipids unique to microorganisms). Procaryotic surfactant phospholipids include, but are not limited to, phosphatidylethanolamine, phosphatidylglycerol, and cardiolipin 1,3 diphosphatidyl glycerol with one free hydroxyl group available for further bonding in anti-inflammatory therapy formulation. Further variations that would intensify the pharmacodynamic therapeutic effects and actions of these chemically bonded biochemicals would include further etherification of the chemically bonded compounds, or, in turn, esterification of the chemically bonded ether compounds. In addition, the esters of these pharmaceutical compounds can be further esterified; and the ethers of these pharmaceutical compounds could be further etherified.

Chemical bonding to a carbohydrate, instead of, a glycerol compound can enhance the pharmaceutical compound's hydrophilic polar head, lubricity, and an affinity for the outer plasma membrane surface. Exemplary carbohydrates include, but are not limited to, galactose, glucose, sorbitol, or polysaccharide, such as glucuronic sulfated polysaccharide or glucosamine and mucopolysaccharides such as, but not limited to, glycosaminoglycanc polymers of glucosamine compounds. In these foregoing synthetic reactions, sulfuric acid, may be required for the ether compound formation or other well-known methods. The condensation of two alcohol groups in ether formation, may be performed by the use of ethylene oxide in that the ethyl group may ultimately become part of the ROR either linkage or other well-known methods. This pharmacodynamic activity may be applicable to the Type II diabetic where the insulin appears to be adequate, but not released from the beta islet cells. Additional adjustment of HLB (Hydrophilic Lipophilic Balance) may be all that is required therapeutically. These synthetic compounds add to the lubricant affect of glycolipids present in other embodiments.

The HLB of these formulations can be advantageously adjusted as described herein or according to the delivery system, described in 60/350,119, filed Nov. 9, 2001, herein incorporated by reference in its entirety. HLB surfactant adjustment components have, as embodiment, any surfactant, such as, but not limited to, hydrophilic surfactants, and have an additive effect and may be blended to more precisely adjust HLB.

The bonding system is similarly applicable to surfactant lipids and phospholipids found in micro-organisms, including, but not limited to, the viruses (such as HIV). The synergistic activity of the subject composition can also help to avert the negative nitrogen balance and weakness, so commonly seen in AIDS, and other diseases caused by microorganisms including, but not limited to microorganisms, such as fungi, yeast, spirochetes, and microorganisms like prions.

As described in above, inclusion of surfactants and the glycosphingolipids, cerebrosides, and the gangliosides can further synergize and the subject compositions as a dissemination delivery system, drug bonding system, prevention of untoward drug side effects and drug metabolic side effects, and also serve in an attempt to reverse such intractable neurologic diseases as spinal cord injury.

Case example: averting a major drug (corticosteroids) side effect.

This subject therapeutic composition was administered locally and systemically to an adult patient, on long term steroids for an unrelated condition, who sustained an extensive dermal and deep subcutaneous tissue trauma. Periodic examinations were made to check the progressive healing, during a six-month observation period. With this therapeutic regime, the wound has completely healed to the satisfaction of the plastic surgeon. The therapeutic regime included all the components and patent claims outlined in Ser. No. 09/639,859, filed Aug. 16, 2001, herein incorporated by reference in its entirety. In addition, the local therapeutic cited components (page 9) derived from the therapeutic regime to counteract the increased presence of collagenase enzyme were administered locally and directly to the wound in the form of retinoic acid Vitamin A applied concurrently with antibiotic bacitracin-zinc oxide ointment. Local treatment applied to adjacent tissue surrounding this deep wound included zinc oxide ointment and retinoic acid. In so augmenting this treatment, the plastic surgeon was pleased to find the planned skin graft could be cancelled. Vitamin A zinc, such as in the form of an acetate, may be used alone or preferably synergistically in combination or conjunction with at least 2 components (e.g., PC and L amino acid(s)) of subject composition (e.g., for respiratory infection or pharyngitis or impending upper respiratory infection) as an orally administered medication, or locally as a lozenge or administered as oral mucosal delivery system as presented here in an embodiment. The local lozenge application is similar to the local use application in an embodiment in wound care. Has been found to greatly diminish the need for antibiotics when used in several patients and in several occasions.

Case example: Greatly accelerating the healing process and averting major drug side effects.

Again utilizing the subject therapeutic regime and compositions, and adding to the local dermatologic therapy and a mucopolysaccharide cartilage skin cream (cartilage derived from bovine tracheal rings), the complete formulation (including amino acid human tissue analog formulation) was now in an adult patient, age 69, with recent traumatic contusion and edema involving the entire forearm. Recovery was observed to occur in five (5) days versus the expected recovery period of one to two (1-2) months. (In this case, with the long term use of steroids complicating the healing process, one would have anticipated a much slower recovery process, making this even more unexpectedly dramatic, hastening the recovery period, and thereby greatly reducing morbidity). The last observation made by the attending physician on Jul. 13, 2001 revealed complete healing of this contusion.

Functional advantages of beta endorphine over morphine include the following: does not cause addition nor an increase in prolactin; not associated with dissemination and metastasis of cancer, and effective in control of pain and shock.

The free L amino acid analog of the active grouping of beta endorphine (available as free L amino acids may be represented by 3 amino acids: one mole of tyrosine, one mole of phenylalanine, and two moles of glycine, also represent analog grouping in common with the enkephalins (met and leu). The free L amino acid analog of beta endorphine may be functionally represented by two moles of L tyrosine, three moles of glycine, three moles of L phenylalanine, one mole of methionine, three moles of L threonine, two moles of L serine, five moles of L lysine, one mole of L glutamine, one mole of L proline, two moles of L leucine, one mole of L valine, two moles of L asparagine, two moles of L alanine, two moles of isoleucine, one mole of glutamic acid (all the foregoing free L amino acids are in these subject compositions being made available as free L amino acid, per se, as a functional therapeutic agent or as a self-bonded for formulation).

Utilizing the above application technology of bonding medication such as, but not limited to, aspirin, e.g., and the reactive groupings of the L amino acids such as, but not limited to, the hydroxyl groups of tyrosine, serine, and threonine; the amine groups with particular reference to the di amine groups of L amino acids arginine and lysine, the carboxylic acid groupings with particular reference to the di carboxylic acid, aspartic acid, glutamic acid and the reactive sulfhydryl groupings of cysteine and cystine.

Similar healing and protein repair applicable in the therapeutic complex bonding of proteins in vivo and in vitro would include sodium stearyl lactolate and also include diacetyl tartaric acid esters of mono and di glycerides, compounds of well-established safety.

The biologic strategy of diseases can be illustrated by snake and bee venom and action of their destructive enzyme phospholipase A2. Other inflammatory products that also are released include, but are not limited to, phospholipid enzymatic breakdown product of phospholipid PAF (platelet activating factor). The therapeutic strategy includes not only supplying the replacement of the biochemical essence of cell membranes, such as, but not limited to, phosphatidylcholine (this replacement effect may occur within seconds or minutes), but also to make available (and to further synergistically incorporate) safe anti-phospholipase A2 medications into the subject compositions. Phospholipase A2 inhibitors such as milrinone (trade name Primacor), generic Enoximone (useful in countering the vascular collapse and impending death associated with meningococcal septicemia, meningitis, and adrenocortical hemorrhage).

Stem cell compositions, along with stem cell stimulant of U.S. Ser. No. 09/639,859, hereby incorporated by reference in its entirety, may be used in cell culture along with progenitor cells from the umbilical cord or other sources in combination with mucopolysaccharide extracellular matrix and cellular membranes to produce blood vessels (such as the aorta), heart valves, or other body components or organs.

The scaffold upon which the stem cell culture can be carried out includes the extracellular matrix mucopolysaccharides taught herein. Alternatively, mucopolysaccharide (such as cartilage, collagen, or chondroitin sulfate powder) can be impregnated onto synthetic scaffolding, such as, but not limited to, polytetrafluoroethylene, dacron, orlon, or nylon or biodegradable polymer fiber of, e.g., polyglycolic and polylactic acid grafting material (such as natural stem cell origin or synthetic cylindrical blood vessels). The above mucopolysaccharide used to impregnate the scaffold may have heparin (also an extracellular matrix component) chemically bonded or adherently attached to the mucopolysaccharide and, optionally, an antibiotic may also be physically adherently attached or chemically bonded. (When this mucopolysaccharide is given orally, 70% of the cartilage, collagen, chondroitin sulfate powder is absorbed undigested. This feature also should be applicable to specially bonded and adherent medications such as, but not limited to, heparin and/or an antibiotic.) Shark aorta and valves of the elasmobranch may also be utilized in view of the low rejection potential associated therewith. Such grafts may be treated with gluteraldehyde, an antiseptic that also complexes protein polymer.

Platelet Activating Factor (PAF), a naturally acetylated lysolecithin and other enzymatic (cyclooxygenase and leucooxygenase) products, can also be counteracted by plant and fish oil omega-3 fatty acid fats. These beneficial effects may be augmented by plankton and algae of the sea so that the patient may produce these omega-3 fats. Aspirin and other nonsteroidal inflammatory drugs can also be provided to counter prostaglandin mediated inflammation by counteracting the enzymatic biosynthesis of prostaglandins. Aspirin also blocks and reverses intestinal cancer production from bowel polyps.

Modulation of uncontrolled cell growth (e.g., cancer) may also be effected by HLB modulation and may also be synergistically incorporated with said therapeutic composition and stem cell compositions described herein. HLB containing compositions can also be formulated with other medications such as, but not limited to, aspirin.

The therapeutic modulation of mitosis (as applied to cancer, for example) may be performed in conjunction with the utility patent stem cell therapeutic composition to permit co-healing and cellular regrowth to restore the tissue and organ status to normal as in many embodiments. Alternatively, adjustment of HLB to hydrophilic range of about 13 to 20 may optionally be performed alone. The surface tension measured in dynes of energy per square centimeter may be calibrated with a tensiometer, such as the duNuoy tensiometer.

Each surfactant, hydrophilic in this case, with usual concentration 0.5 to 1.0 percent concentration, may be so measured and monitored in vitro in physiologic saline or tissue culture, or in vivo, in mammalian tissue undergoing treatment (control vs. therapeutic application).

Benchmark tests of the efficacy of 3-D protein processing technology include:

1. Polarizing microscopic examination for absence of Maltese Cross crystal characteristic of the processed 3D structure of starch granule, in sharp contrast to non-processed sample with intact starch granule;
2. Immunologic studies for protein identity, e.g., ELISA inhibition studies using the allergic patient's reactive to the native unprocessed protein, in contrast to the 3D processed protein;
3. Histamine release studies using allergic patient's white blood cells and serum with histamine release reactive to the native unprocessed protein (in contrast to the 3D processed protein);

4. Bradford test for 3-D transformation after 3-D protein processing reactive for newly-exposed aromatic amino acids (particularly tryptophan, tyrosine, and phenylalanine, less so for histidine); and 5. Tests and new specific tests for 3-D pathogenic protein processing of protein polypeptide with liquid nitrogen and/or supercritical $CO_2$. This processing may be reinforced with surfactant processing with hydrophilic surfactant and/or their additional blends such as, but not limited to, Tween 80.

Objective Goal:

Processing of animal dander (such as cat dander) illustrates the feasibility of treating a cat with Tween 80 solubilized in a 1 to 2 percent aqueous glycerine alcohol with a smooth petting cloth, sponge or chamoix to reduce the allergenicity of the family cat. The efficacy of this processing technology was exemplified by processing commercial testing solutions of cat dander with ten percent Tween 80 added to this testing extract by gently warming and mixing to enhance solubility.

The results of the protein and IgE, ELISA inhibition assays are presented in the table below and companion graph of in vitro basophile histamine release.

As described below, allergenic extracts derived from cat hair and cat pelt source materials were modified. The modified extracts yielded significantly higher values based on the Bradford dye binding in contrast to the control untreated cat hair and pelt. Similarly, significantly less histamine was released, using in vitro white blood cell basophiles from a cat allergic patient exposed to treated cat hair extract, as compared to histamine released when the allergic patient was exposed to the untreated control cat hair extract.

Standardized cat hair extract (laboratory code GTE 3) at 10,000 BAU/ml and non-standardized glycerinated cat pelt extract (laboratories) at 1:20 weight/volume were treated with Tween 80 hydrophilic surfactant for modification of cat protein 3D molecular spatial arrangement by processing modification resulting in reduction of allergenicity for processing modification. The unmodified extracts were maintained at 2-8 degrees F.

Analytic Assays:

The protein comparisons of unmodified and modified extracts were determined using the Bradford protein assay using bovine serum albumin as the standard. Similar comparisons were made using the basophile histamine release in vitro assay from the white blood cells of a cat allergic patient.

Results:

The results of the proteins and IgE ELISA inhibition assays expressed as relative potency are presented in the table below, and demonstrates the 3-D processing effects of "straightening" of Protein (cat) polymer. This 3-D structural change of the allergenic cat hair protein molecule prevents or reduces the severity of the allergic disease.

| Extract | Bradford Protein Consent (mg/mL) | IgE ELISA |
| --- | --- | --- |
| Cat Hair - Modified | 11.70 | 0.906 |
| Cat Hair - Control | 0.16 | 1.000 |
| Cat Pelt - Modified | 34.60 | 0.375 |
| Cat Pelt - Control | 0.72 | 1.000 |

Documented are similar (100-250 x) decreases in allergenicity using supercritical $CO_2$ processing of allergen of foods. Similar comparisons were made using hereof reduction of allergenicity of reactive components of cat dander in the basophile histamine release assays from the white blood cells of a cat allergic patient. See FIG. 4.

On further review, using the above technique dispensed in a plastic spray pump bottle containing 98 to 99 percent polysorbate 80 such as Tween 80 and conforming to the composition of Tween 80®, starting with a concentration of 0.25% to 2% with diluent $H_2O$, 0.5 to 1 percent glycerine, a good emollient without HLB effect and 0.5 to 1 percent of any non-toxic alcohol, should bring about the above effects. HLB effect is additive, 0.5 to 1% P.C. (HLB of 13), 0.5 to 1% sodium lauryl sulfate HLB of 20, may be respectively added to further adjust ideal HLB to optimize hypoallergenic effect for various animals or pets, e.g., dog, cat, animal hair (dander), etc.

Thus, the subject invention provides methods of reducing the allergenicity of pet allergens (e.g., cat dander) comprising the application of a solution comprising (v/v) primarily polysorbate 80 such as Tween 80®, and conforming to the composition of Tween 80® and starting with a minimum concentration or strength of 0.25 to 2%; 0.1 to 50% (v/v) of an acceptable carrier, such as glycerine, and 0.1 to 50% of any non-toxic alcohol such as, but not limited to, ethel alcohol or isopropyl alcohol (v/v). In certain embodiments, the carrier and alcohol will be present in amounts of 0.1 to 5% (v/v), 0.3 to 3% (v/v), or 0.5 to 1% (v/v). Optionally, an aerosol can, with the addition of Freon (amount required to develop pressure) or other suitable propellant, tolerable and efficacious to animal application, should be used. May also be used to lessen allergenicity and threatened reaction in same fashion if exposed by contact or inhalation to an allergen, e.g., but not limited to, poison ivy plant or similarly lipophilic allergenic weed as ragweed pollen, mold spores, or allergenic animal dander. After washing exposed area with water as diluent until one can use a more specific wash of 0.25% to 2% hydrophilic surfactant (HLB 18) as Tween 80® or sodium lauryl sulfate (HLB 20).

In the case of inhalant exposure, after blowing the nose to blow out allergen, then wash nostrils with saline and same subject hydrophilic surfactant (hydrophilic surfactant may be combined in saline), as inhalant pump spray or aerosol. Respiratory allergy or respiratory infection may be complicated by sinusitis and loculated purulent debris including hydrophobic cell membrane surfactant, microorganism lipids, phospholipid, and lipoprotein polysaccharides may be relieved by lavage and drainage with same subject hydrophilic surfactant composition (also applicable for any focal area of pus).

Similar application of subject composition in systemic use of subject composition, with particular reference to specific component PC (HLB of 13) may be used to reduce adherent hydrophobic surfactant effect of blocked coronary artery.

To reduce the allergenicity of foods anywhere in the food chain, it is the same high HLB hydrophilic surfactant technology such as, but not limited to, Tween 80 and PC processing agents acceptable for food use, as used in other embodiments in processing foods to reduce allergenicity. May also be administered orally as an antidote to diminish allergenicity of an already ingested food as soon after ingestion as possible, starting with 0.25% to 2% solution of hydrophilic surfactant such as, but not limited to, Tween 80. Caution: a very concentrated solution of hydrophilic surfactant (HLB 13-20), such as, but not limited to, Tween 80 (HLB 18) might dehydrate the suspected allergen with reversal of HLB to a former more hydrophobic effect status, thereby reversing and cancelling this processing and therapeutic action.

The probiotic and prebiotic effect of the subject compositions can also be enhanced by, as well as being produced by, amino acids such as those found in red wine of the French, as well as yogurt of the Afghan and Kurdish people. Such amino acids are not found in the unfermented substrates of these foods (thereby accounting for dramatic disease protective factors that may be synergistically incorporated in all of the above products, while at the same time maintaining the low-risk enhanced benefit medication profile presented in these patent applications). The yogurt bacteria (the *lactobacillus bulgaricus* producing, the greater bulk of the amino acids than *streptococcus thermophilus* and complete their fermentation process in four hours) work synergistically with slower growing-probiotic bacteria with good intestinal adherence properties *lactobacillus acidophilus* and *casei* (producing lactic acid) bifidobacteria (producing acetic and lactic acid) produce butyric acid with its antimutagenic, anticarcinogenic, and anti-bacterial activity. Butyric acid can also reduce cholesterol.

When L amino acids of this composition, concurrent with parenteral feedings, are given intravenously along with nothing by mouth within 24 to 48 hours, the gastrointestinal mucous membranes atrophy. The trans-location of commensal microorganisms or creation of a food portal (by this commensal microorganism) by a creating permeability defects having been deprived of food, particularly nitrogenous food, seems to be the factor in changing this mutual commensal bacterial flora relationship to that of invading microorganisms. This mutual commensalism seems to explain the intact functional gastrointestinal mucosa and the importance in this subject composition in inflammatory bowel disease; changing bacterial flora due to antibiotics, gastrointestinal surgery, as well as the pharmacodynamic rationale for adding prebiotic and probiotic bacteria, along with enzymes, such as, but not limited to, the digestive enzymes, including amylase, pancreatin, pepsin, lipase, papain, bromelain to subject composition, in particular, as applied to inflammatory bowel disease. These synergistic additions to the subject composition have furthered the management of a Crohn's inflammatory bowel disease patient further minimizing flare-ups and the need for corticosteroid medication, also applicable to peptic ulcer now known to be mediated by *Helicobacter pylori*.

The microorganism, plant, and/or animal components of therapeutic stem cell composition of the subject invention have minimal, if any, toxic potential (in contrast to synthetically derived pharmaceutical compounds (even those as relatively safe and time-honored as aspirin and its other non-steroidal anti-inflammatory group members)). In diseases associated with aging, aspirin is quite effective as an antiplatelet or anti-clotting agent for treating coronary artery, atherosclerotic, or heart disease. However, even the smallest pediatric, slow release, long acting Ecotrin aspirin (in the form of 81 milligram tablets administered every other day) can cause gastrointestinal symptoms, such as the activation of a peptic ulcer or bleeding.

Additionally, bleeding complications must be constantly surveilled and considered with drugs such as aspirin or NSAID. Aging is associated with catabolism and negative nitrogen balance. Aspirin may also be associated with negative nitrogen balance, thus raising another unwanted complication for disease management in the aging population. Aspirin may also increase the production of corticosteroids, which may also account for these potential side effect risks, as well as interference in healing.

Another use for the stem cell compositions of the subject invention is in the prevention of tissue and/or organ graft rejection or the treatment thereof. Sheep's milk, with its high amino acid content, as well as its equivalent protein concentration, has been shown, in over 99 percent of the cases, to be free of major rejection-like reactions (e.g., such as those associated with allergic hypersensitivity), and may be used synergistically with the foregoing stem cell therapeutic composition. The sheep, its tissue, and its milk, as used and reported here, do not have to be specially cloned to avoid rejection mechanisms. The Suffolk wool producing sheep primarily share the genetic predisposition to harbor the Scrapie prion in sharp contrast to the Friesland dairy sheep. A similar disease, Alzheimer's exhibit similar genetic predisposition (as a Scrapie prion disease) with a similar prion-like beta pleated sheet protein (versus normal alpha helix random coil 3-D protein and proteomics). I have noted that the absence of this rejection-like hypersensitivity reaction as shown with sheep's milk correlates with the sheep (in contrast to goat, horse, and cow, e.g.) lack of immunologic antibody response to human protein (exhibiting poor template reflective transcriptive antibody response to human protein).

It is an object of the invention to provide novel uses for whey permeate, which has heretofore been regarded as an unusable waste by-product of cheeses manufacturing. It is also an object of the invention to provide an electrolyte beverage based upon whey permeate, useful as a sports drink or as a therapeutic aid in the replacement of electrolytes lost through vomiting or diarrhea. Another object of the invention to provide a process for the preparation of whey-based electrolyte beverages. Yet another an object of the invention to provide substantially hypoallergenic milk products from dairy permeates, which have enhanced flavor and palatability. These and other objects of the invention will be apparent from the following description.

An electrolyte beverage is provided comprising a pasteurized whey permeate and one or more flavoring agents. The whey permeate component preferably has a milk protein content of not more than about 0.25 wt. %, more preferably not more than about 0.1 wt. %, most preferably not more than about 0.025 wt. %.

A process for preparing an electrolyte beverage is also provided. Whey is filtered to form a whey permeate. The whey permeate is collected and treated to arrest microbial activity in the permeate. The treatment occurs promptly before significant microbe-induced degradation has occurred in the permeate. The permeate is then flavored with one or more flavoring agents. Preferably, the step of filtration is through a filter having a molecular size exclusion of at least as low as about 20 kDa, more preferably at least as low as about 10 kDa. The protein content of the permeate is preferably no more than about 0.25 wt. %, more preferably no more than about 0.1 wt. %, most preferably no more than about 0.025 wt. %.

A process for preparing a substantially hypoallergenic milk product is provided. Milk or whey is filtered to form a dairy permeate containing no more than about 0.5 wt % milk protein. The permeate is collected and treated to arrest microbial activity in the permeate. The treatment occurs promptly before significant microbe-induced degradation has occurred in the permeate. A hypoallergenic component is then added, and optional hypoallergenic fat.

By "dairy permeate" is meant a liquid portion of milk or whey which is collected upon passage of milk or whey, or liquid fraction of milk or whey, through a filter having a molecular size exclusion sufficient to filter out at least about 99.5 wt % of milk proteins, such that the permeate is rendered substantially hypoallergenic. Preferably, the dairy permeate results milk or whey using a filter having a molecular size exclusion of at least as small as about 20 kDa.

"Milk permeate" means a dairy permeate from filtration of milk. "Whey permeate" means a dairy product from filtration of whey. By "milk" is meant not only whole milk, but also skim milk or any liquid component thereof. By "whey" is meant the milk component remaining after all or a substantial portion of the fat and casein contained are removed. All percentages expressed herein are weight percentages (wt. %), unless indicated otherwise.

Cheeses are made by adding the enzyme rennin (rennet extract), or a combination of rennin and acid (usually lactic acid produced by starter cultures), to coagulate milk. The curds are separated from the whey and processed into cheese. All cheeses require a period of time for ripening. Ripening is brought about by microbial agents including bacteria, molds and/or yeasts. The same microbes are present in the whey. Their action can continue the cheese making process in whey, even though the curd has been removed.

Following removal of curd, whey is filtered to remove protein. The permeate, while being substantially free of protein, is an inexpensive source of minerals and vitamins, particularly those minerals which are found in modern electrolyte beverages used for the replacement of electrolytes. The present invention provides for the effective commercial utilization of whey permeate, which would otherwise be discarded by cheese manufacturers, or sold for a few cents per pound.

Dairy permeate is obtained upon crude filtration of milk or whey, that is, filtration using a dairy filter or membrane having a molecular weight size exclusion of approximately 20 kDa or lower. Whey may be diluted at least about 20% with water during the cheese making process, prior to filtration. If the filtration process is running properly, the permeate will have a protein content of as low as about 0.025%, based upon the weight of the permeate. Inefficient filtration, such as through a worn filter membrane, may increase the protein concentration by an order of magnitude, i.e., to about 0.25 wt. %. The protein concentration may be maintained at 0.025 wt. % by frequent servicing or replacement of the filter membrane/filter. Moreover, the protein content of the permeate can be minimized by selecting a filter/membrane with a smaller size exclusion, e.g. a 10 kDA filter.

A typical filter element useful in generating permeate from whey or milk comprises a polyethersulfone spiral membrane (Deaal Ultrafilter ER 3840C) having an average selectivity of 0.01.mu. (nominal), a typical operating range of 20-145 psi, and a maximum pressure drop per membrane element of 60-65 psi. The usual ideal daily range of pressure is 20 psi back pressure and 80-85 psi feed pressure.

The filter should be suitably "primed" prior to use. This is accomplished by allowing whey (or milk) to pass through the filter for at least about 15 minutes before collecting any of the permeate. The pre-15-minute permeate should be discarded as it may contain proteins large enough to be considered allergenic. For a whey permeate, the completion of the priming period is signalled by establishment of a permeate flow equal to about 84% by volume of the whey volume before filtration. Successful priming is also indicated by establishment of a permeate flow which has only minimal cloudiness, compared to the unfiltered whey.

Regardless of the efficiency of the filtration, the permeate should not have a milk protein content of more than about 0.25 wt. %, preferably no more than about 0.1 wt. %. A properly functioning dairy filter of the type described above will produce a permeate having only 0.025% protein. Milk contains about 3.25% protein. Thus, the permeate contains only about 0.71% of the protein of milk.

Maintaining a very low protein concentration in the dairy permeate, and therefore in the beverage based thereon, is important to minimizing the allergenicity or the product. Electrolyte beverages are typically entirely protein-free, since they generally comprise nothing more than synthetic mixtures of mineral salts to which flavoring has been added. Thus, the consuming public has come to expect that electrolyte beverages are hypoallergenic. Where, as in the present invention, a good-tasting electrolyte beverage is derived from milk protein-containing raw materials, care must be taken to reduce the allergenicity of the product to an acceptable level, consistent with the expectation that an electrolyte beverage will not contain allergens. Whey permeate, while not being perfectly hypoallergenic, contains such little protein that its consumption by the majority of milk protein-allergic individuals will be tolerated. Veterinary chemicals and medications used in dairy husbandry generally bind protein. Thus, the elimination of protein from the whey permeate will also remove such chemicals and medications.

It has been found that to maintain palatability, the dairy permeate should be treated quickly after it is generated. Whey permeate, in particular, is much more susceptible to bacterial contamination than milk. The same bacteria responsible for fermenting milk curd into cheese is also present in whey, and hence the whey permeate. Should those bacteria be permitted to act on the whey permeate to a substantial degree, the permeate, and hence the beverages formed therefrom, will possess a "cheesy" off-taste. Thus, the permeate should be treated as soon as possible after its generation to arrest the activity of the cheese-making microbes therein. Treatment should occur before significant microbe-induced degradation of the permeate has taken place. The common cheesy odor of whey products is thereby eliminated.

The most common change in milk products resulting from the growth of microorganisms is the development of acid. The action of cheese-making bacteria on the dairy permeate, and whey permeate in particular, may be monitored as a drop in the pH of the permeate. The pH of the dairy permeate, which is typically about 6.2-6.4 (6.3 being the most usual value) immediately after the permeate is collected, will decline to about 6.2, and possibly lower, such as to 5.9, if the cheese-making bacteria remain unchecked. Thus, the dairy permeate should be treated before the pH of the permeate falls off significantly from 6.3. It has been observed that prompt treatment delays the onset of deterioration of the pH, titratable acidity, taste and smell by 3 or more hours at room temperature. Preferably, the permeate is treated to arrest the cheese-making microbes much before the pH of the permeate falls more than about 0.3 pH unit from the initial pH value at the time of collection. A fall in pH of this magnitude is associated with departure from a fresh milk-like taste. It has been found that a significant increase in microbial growth (about two-fold) will occur about 2 hours following permeate collection, at about room temperature. At about one hour there is no significant change in microbial growth. The least growth is seen at about 15 minutes post collection. Thus, it is preferred that the permeate is treated to arrest microbial growth within about 2 hours of the permeate's collection, more preferably within about 1 hour, most preferably within about 15 minutes. The permeate should be treated even sooner if the dairy plant is not located in a cool climate, or is not air conditioned. Thus, where possible, the permeate is treated immediately upon collection. Where the permeate is refrigerated after collection, the interval may be longer, as refrigeration will retard the action of the cheese-making microbes and preserve the flavor of the whey permeate for some time. If a dry powder is the goal, then immediate drying enhances the efficiency of energy utilized.

The treatment to arrest microbial activity is preferably coupled with permeate production in a continuous process. Accordingly, the permeate is continuously collected. The continuously collected permeate is continuously treated to arrest microbial activity. In this manner, the permeate is treated without the delay which would be attendant in batch production and processing.

The most effective treatment for arresting the action of microbes in the permeate comprises pasteurization. Pasteurization generally comprises partial sterilization at a temperature and for a period of time that destroys objectionable organisms, without major chemical alteration of the product. To arrest the activity of the cheese-making bacteria in the permeate, particularly whey permeate, pasteurization may comprise heating the permeate to a temperature of at least about 110° F., more preferably at least about 120° F., most preferably about 145° F., and maintaining that temperature for at least about 30 minutes with constant stirring, for example, stirring with an agitator at 60 rpm. According to the so-called "holding method", the permeate may be heated to 145° F. and held at this temperature for 30 minutes with constant stirring with an agitator at 60 rpm. Alternatively, a high-temperature, short-time process ("batch pasteurization") may be employed. The latter requires a temperature of 162° F. for 16 seconds. Even shorter duration processes (278° F. for 4-6 seconds, or 285° F. for 2 seconds) may be employed, but are not preferred because of the added expense. Any combination of time and temperature may be utilized so long as it achieves adequate pasteurization of the whey permeate to result in the arrest of microbial growth. The result is an excellent dairy taste which is maintained under refrigeration for three weeks. A taste panel of five individuals found the taste of refrigerated whey permeate to be bland but pleasant, and not salty.

The dairy permeate is essentially free of casein and lactalglobulin, which are removed in the filtration process. Lactalbumin, which is not removed in the filtration process, is the most heat labile of all proteins. It is readily denatured even by pasteurization conditions. Hence, the permeate is substantially hypoallergenic, even if some lactalbumin remains therein.

The dairy permeate, from which greater than 99% of the milk protein has been removed, is also essentially free of any veterinary or agricultural chemicals since protein comprises the principal binding sites for these chemicals.

The permeate may be rendered even more hypoallergenic by heat treatment at 145-155° F. with constant stirring for 24-48 hours, preferably 36 hours. Thus further heat treatment may have the advantage of further denaturing or destroying secondary structures of food antigens. In particular, the heat treatment will denature any lactalbumin which may remain in the permeate, although trace portions of this heat labile protein which has been treated for 30 minutes at 145° F., for the minimum essentials of batch pasteurization, will not have an effect on most allergic individuals.

Although the permeate, appropriately treated to arrest microbial growth, may be utilized in liquid form to prepare the beverages described herein, it may also be dried to a powder and later reconstituted. If a dried permeate powder is desired, the drying should take place promptly after the treatment to arrest microbial growth. This obviates the need for refrigeration of the powder.

The liquid permeate may be dried to a moisture content of about 4 wt. % by spray drying employing, for example, a dryer inlet temperature of 400° F. and a dryer outlet temperature of 200° F., a drying time of four to five hours, a pressure of 2000-2500 psi, and a 68-70 gauge spray nozzle bore. Suitable spray dryers are available from, for example, Delfab (Delaware, Ohio). Suitable spray nozzles are available, for example, from Spray Drying Systems (Wheaton, Ill.).

Alternatively, the liquid permeate may be concentrated to about 45 wt. % moisture in a suitable evaporator device, such as the devices available from Weegan (Logan, Utah). In subsequent spray drying to 4% moisture, the spray nozzle gauge should be increased to 60-62 gauge, in order to handle the thicker consistency of the evaporated permeate. Preferably, about 0.25% soy-oat powder is added to the permeate to promote drying. Drying by a belt-dryer may be substituted for spray drying. The dried powder may be optionally further heat treated at from about 145 to about 155° F., for from about 24 to about 48 hours, preferably about 36 hours.

The dried permeate powder may be reconstituted with water. Spring water or distilled water should be used to avoid the chlorine taste of tap water. The powder may be reconstituted by adding 95 wt. parts water to 5 wt. parts powder, for example.

To prepare a hypoallergenic milk product, the permeate (liquid or dried milk permeate or whey permeate) is supplemented with hypoallergenic protein and, optionally, fat, as set forth in U.S. Pat. No. 5,064,674 or U.S. Pat. No. 5,204,134, incorporated herein by reference. The hypoallergenic protein component may comprise hypoallergenic protein per se, such as protein from cereal or vegetable sources. Alternatively, or additionally, it may comprise free amino acids, or "short chain polypeptides" of animal source. By "short chain polypeptide" is meant a polypeptide having a molecular weight of not more than about 5 kDa, preferably not more than about 1.5 kDa, more preferable not more than about 1 kDa.

Sources of hypoallergenic protein include, but are not limited to: oat cereal (which has a high protein level of about 18%); rice cereal; barley cereal; or any other food source having a low allergenicity and ample protein content. Vegetable sources of protein may also be used, so long as they have a low allergenic potential. Vegetable sources of low allergenic protein include, for example, potato and soy isolate. Combinations of the foregoing proteins may also be used. Oat cereal, for example oatmeal, is preferred because it not only enhances the protein content, but also adds to the taste of the resulting product. The oat cereal is used as a very finely ground flour, to facilitate dissolution into the permeate. About 5 to 10 grams of the very finely ground and sieved cereal flour is added to about 100 cc of product. The resulting mixture has a protein content of about 0.9 to 1.8% by weight, which is similar to human breast milk.

When cereals are used, protein soy isolate may also be added to enrich the lysine amino acid value of the cereal. Additionally, the protein may be supplemented with, among other things, methionine, cystine, and iodine to meet the minimum daily requirements.

Protein soy isolate is preferred for use in hypoallergenic milk which is intended for infants who require a single source of protein, or children and adolescents with important growth factor requirements. Cereal hypoallergenic protein sources can be used in the hypoallergenic milk for adults. For example, if a multiple source of protein is desired, any combination of hypoallergenic protein sources may be used.

In lieu of, or in addition to, supplementation with hypoallergenic protein, the product may be supplemented with amino acids, short chain polypeptides, or a combination thereof. Free amino acids and short chain polypeptides are hypoallergenic regardless of source, and therefore will not contribute to the allergenicity of the milk product. Preferably, the amino acids comprise a mixture of amino acids, most preferably a mixture containing at least the nine amino acids which are essential to the human diet:

| | | |
|---|---|---|
| Threonine | Valine | Phenylalanine |
| Methionine | Isoleucine | Histidine |
| Lysine | Leucine | Tryptopan |

The short chain polypeptides may comprise individual polypeptides or a mixture of polypeptides. The short chain polypeptides and amino acids may be obtained by appropriate hydrolysis of any suitable polypeptides or proteins. Preferably, they are obtained from milk proteins, so that the reconstituted hypoallergenic milk product of the invention maintains a portion of the protein nutritional content of whole milk. Hydrolysates of milk proteins are commercially available, a highly hydrolyzed pancreatic digestive of casein. A hydrolyzed pancreatic digest of another milk protein, lactalbumin, may be utilized. High-performance liquid chromatography indicates that these products are free of polypeptides having a molecular weight of greater than about 1.5 kDa. Hydrolysates of non-milk proteins may also be employed, e.g., a papaic digest of soy flour.

The sources of the optional fat component may include deproteinized clear butter and butter oil or butter fat, polyunsaturated and mono- and/or polyunsaturated vegetable oil or fat from milk free margarine sources, sesame, safflower, and the like, or mixtures thereof. The foregoing fats are hypoallergenic.

Deproteinized hypoallergenic butter for supplementing the permeate may be made from commercially available salt-free, sweet 99.99% anhydrous milk fat. The milk fat is melted in boiling water. The resulting butter oil is then removed from the boiling water, such as by pipetting it off the surface of the water. The boiling water results in extreme heat denaturation of protein and also renders the resulting heat-denatured protein insoluble. The process removes, by dilution and washing of the milk fat with water, any protein which may be contained in the fat as a contaminant. The process may be repeated any number of times to ensure the purity of the resulting butter product. Vitamin E may be added to prevent oxidation.

The deproteinized hypoallergenic butter advantageously includes vitamin E as an antioxidant. Vitamins, and further minerals in addition to whose present in the permeate, are also optionally added to the protein and fat-supplemented permeate. Such vitamins and minerals are added, so that the resulting milk products meet the minimum daily requirement.

Whey permeate appropriately flavored with one or more flavoring agents, may be used as an electrolyte beverage. Pasteurized whey permeate will generally have a potassium concentration of about 37 mEq/L. While a such a high potassium level is tolerated by most individuals, it may be desirable to reduce the potassium level by diluting the permeate before use in formulating beverages, particularly electrolyte beverages. High potassium concentrations might be harmful to individuals suffering from kidney or cardiac disfunction, and may be undesirable even for normal individuals after extreme exercise. Thus, it may be advisable, particularly in the preparation of electrolyte beverages for consumption by patients with kidney function impairment, to reduce the potassium level of the permeate to about 30 mEq/L or lower, more preferably to about 25 mEq/L, or even lower. The diluent most advantageously comprises water. For use in compositions designed to be taken following extreme exercise, the permeate should be diluted about 1:10 or more, to provide a potassium concentration of no more than about 5 mEq/L, preferably no more than about 4 mEq/L, ideally no more than about 3 mEq/L.

Whey permeate which has been diluted with water, e.g., 2:1, to adjust the potassium concentration to a level appropriate for electrolyte therapy for fluid loss, is somewhat low in sodium. Whey permeate contains about 15 mEq/L sodium. Thus, it is appropriate to boost the sodium concentration of the whey permeate by adding sodium, such as in the form of sodium chloride and/or sodium citrate, particularly when the permeate is used as an electrolyte beverage. Other sodium salts may be substituted. The sodium concentration of the beverage is preferably boosted in this manner to at least about 45 mEq/L.

The approximate concentrations of other minerals in the whey permeate are as follows: calcium, 10 mEq/L; magnesium, 5 mEq/L; and phosphorus, 7 mEq/L.

The dairy permeate contains substantial amounts of carbohydrate, in the form of the disaccharide lactose. The enzyme lactase (beta.-galactosidase) may be added to the beverage to break down lactose, in order to avert problems with consumption by lactose-intolerant individuals, and to promptly provide monosaccharides not dependent on disaccharide digestion. Approximately 15% of the population over the age of six years has been estimated to suffer from lactase deficiency. The amount of lactase added should be sufficient to substantially hydrolyze the lactose contained in the permeate into its component monosaccharides, galactose and glucose. The glucose contributes to the sweetening of the permeate.

Further dilutions and mineral adjustments may be incorporated as necessary to obtain a permeate product which is isotonic or isomolar with respect to the osmolarity of blood (300 milliosmoles/L).

Whey permeate is flavored with one or more flavoring agents for use as an electrolyte beverage. The flavoring agent may comprise virtually any agent suitable for flavoring beverages, compatible with the use of the beverage as an electrolyte replacement drink. The flavoring agent may advantageously comprise, for example, any of the following fruit flavors, derived from fruit concentrates of low allergic potential: lemon, lime, grapefruit, banana, pear, hypoallergenic chocolate, low-acid orange and blends thereof. Low-acid orange has been observed to be hypoallergenic. Pear is preferably heat-treated to further enhance hypoallergenicity. Vanilla, oat, and rice are other suitable flavors. Such flavoring agents are commercially available. The amount of flavoring agent added to the pasteurized permeate depends upon the strength of the particular agent and the desired taste. Typically, the beverage may comprise about 5 wt. % flavoring agent.

The resulting electrolyte beverage may be taken as a sports drink after vigorous exercise, to replace sweat. The beverage may also be used as a therapeutic drink, to replace gastrointestinal fluid and electrolytes lost from vomiting or diarrhea caused by gastroenteritis.

The electrolyte beverage may also be used as an "elemental" feeding, with the inclusion of appropriate additional ingredients, such as amino acids. Elemental feeding compositions will generally contain simple sugars such as glucose, amino acids and electrolytes. Such a feeding composition may be used for providing nourishment to post-operative patients, particularly post-operative bowel surgery patients. It also finds use in administering nourishment to patients suffering from bowel disorders or diseases, such as chronic ileitis or colitis. Amino acids may also be added in the case of a sports exercise drink, to stimulate the restoration of muscle tissue which may be lost through vigorous exercise.

When added to the electrolyte beverage, amino acids are present in the range of, for example, from about 0.5 to about 2.0 wt. %. Preferably, a mixture of amino acids is employed which contains no more than about 0.25% protein, preferably no more than about 0.1%, most preferably no more than about 0.025%.

Although derived from a milk product, i.e., milk or whey, the dairy permeate is substantially milk protein-free. The dairy permeate contains no more than about 0.25 wt %, more preferably no more than about 0.1 wt %, most preferably no more than about 0.025 wt %, milk protein. Thus, beverages utilizing the permeate may be enjoyed by mildly or moderately milk-allergic individuals.

To form a chocolate-flavored drink, the dairy permeate, and the whey permeate in particular, may be flavored with a cocoa powder. To maintain the reduced allergenicity of the product, only hypoallergenic chocolate flavorings are recommended, such as the heat-treated cocoa powder described in U.S. Pat. No. 4,078,093. As described therein, a hypoallergenic cocoa powder is prepared by heating ground nibs of cocoa beans at high temperature and pressure. Alternatively, the whey permeate may be flavored with the complete hypoallergenic chocolate described in U.S. Pat. No. 4,078, 093, which is prepared by mixing the cocoa powder with sugar, cocoa butter and flavoring additives, followed by further heat treatment to produce a hypoallergenic chocolate.

Alternatively, the chocolate flavoring agent may comprise defatted cocoa. It has been unexpectedly found that in defatting cocoa to obtain a substantially completely fat-free cocoa powder (>99% fat-free), such as by defatting with a supercritical fluid, e.g., $CO_2$, the resulting powder is rendered hypoallergenic, without the need for heat denaturation of protein allergens as described in U.S. Pat. No. 4,078,093.

At supercritical conditions, $CO_2$ exhibits the properties of both a gas and a liquid, and is thus used as a solvent, without leaving a toxic residue. $CO_2$ is preferred as the supercritical fluid since other defatting solvents, most notably hexane, may leave a residue which can cause an adverse reaction in allergic and asthmatic patients.

Without wishing to be bound by any theory, it is believed that removal of the fat from cocoa powder may impact on the three-dimensional structure of the protein component of cocoa, such that the human immune system will no longer recognize the proteins contained therein as allergens. Defatting also results in removal of mold, which may contribute to allergenicity.

The fat-free cocoa powder described herein may be distinguished from the heat-treated cocoa powder of U.S. Pat. No. 4,078,093. The latter contains substantial amounts of fat, at least 8%. The defatted hypoallergenic cocoa powder is used as a flavoring for the whey permeate.

The defatting process results in the elimination of mold, since the coating of microscopic mold spores comprises fat. Removal of yeast mold allows the cocoa powder to be utilized in soft drink plants, where the presence of mold is highly undesirable. Moreover, many patients allergic to chocolate are also allergic to other mold-containing foods, such as wine and cheese. It is believed that removal of the mold may contribute to the reduced allergenicity of the fat-free cocoa powder.

Essentially fat-free (>99% fat-free, more preferably at least 99.95% fat-free) cocoa powder may be prepared by defatting treatment of cocoa powder with supercritical $CO_2$. It may be prepared according to the process of U.S. Pat. No. 3,923,847. Cocoa powder is contacted with carbon dioxide which has been brought to supercritical conditions in respect to temperature and pressure. Pressures above 75.3 atmospheres, which is approximately equal to the $CO_2$ critical pressure, and temperatures above the $CO_2$ critical temperature (31.6° C.), are necessary for fat extraction. In practice, a pressure above 100 atmospheres gauge, and preferably between 200 and 400 atmospheres gauge, may be used. It is only necessary to work slightly above the critical temperature of $CO_2$. Preferably, the temperature is in the range of from about 40° C. to about 60° C. The contact time may generally comprise from about 2 to about 10 hours, with 4-5 hours being preferred.

The dairy permeate product may be stored in dry powder form and reconstituted with filtered water or soda as a sports exercise or electrolyte replacement beverage. Per unit of dry weight the product contains no fat, compared to 5.4% fat in skim milk and up to 38.3% fat in whole milk, based upon dry weight. In medical or veterinarian therapy one would strive for therapy greatly minimizing the risk or in most cases completely avoiding the risk of major or minor adverse side effects along with a high degree of therapeutic efficacy including anti-inflammatory, anti-rejection, synergistic activity, tissue healing capacity along with disease repair tissue proteins synthesis and re-synthesis, along with cumulative beneficial healed tissue effects highly competitive to corticosteroids in that relapse in major disease with stopping the medication does not occur for as long as six to twelve months or even longer as is the case with subject composition and its component optically active L amino acids and amino acid glycine (optically inactive neither L nor D).

This favorable efficacy coupled with dramatic tissue healing effect of therapeutic subject composition components L amino acids and amino acid glycine (optically inactive neither L nor D) analogue not only in structure and function to NSAID, 5ASA but also analogue and mimicking in structure and function to human tissue, specifically also analogue and mimicking the newest forefront of pharmacologic therapy, the human stem cell, (while not requiring human tissue). All of these beneficial functions and structures are dependent upon not only upon the 3D levorotary optical activity but also the left handed spin of electrons emitted from L amino acids and its 3-D tetrahedral spatial configuration and upon the alpha amino alpha carboxylic high-energy carbon and its contribution to the 3D tetrahedral spatial configuration, but also highly dependent upon L for amino acid. In this case also stimulating, activating and facilitating tissue healing and tissue protein synthesis and re-synthesis, and of molar ratios analogue to and mimicking human tissue. The subject therapeutic composition is thereby also an analogue to biochemical and immunologic sell and thereby minimizes potential adverse side effects.

In further contrast the aromatic benzene ring amines and its anti-inflammatory compounds derived from aniline, exhibit (#10) such as acetaminophen and its progenitors including aniline stack in a planar fashion of planar layers of benzene ring electron cloud compounds and further are not separated by a two carbon bridge containing the alpha carbon and its alpha amino alpha carboxylic acid key pivotal carbon to tissue healing protein synthesis grouping (exhibit #5 vs 5 ASA).

All of these beneficial functions and structures are dependent not only upon the 3-D levorotary optical activity but also upon the left handed spin of electrons emitted from amino acids and pivotally dependent upon the alpha amino alpha carboxylic high-energy ionizing side chain grouping carbon and its contribution to the 3-D tetrahedral spatial configuration which endow these L amino acids with their tissue healing protein synthesis capacity synergistically along with non-covalent bonding forces.

This can best be visualized and exemplified by exhibit (#10 a.) in contrast to exhibit (#10) comparing structurally for example the three carbon organic acid propionic acid anti-inflammatory derivatives such as but not limited to naproxen and ibuprofen wherein the potential alpha carbon next to carboxylic add group, exhibit (#3) and (U 3a.) fails to contain the amino group characteristic of the tissue healing features of the L amino acids in addition to its anti-inflammatory side chains positioned on its second carbon as is the case for example of L alanine or the aromatic amino acids such as but not limited to tyrosine, tryptophan or phenylalanine Bonding and special bonding techniques to incorporate L Amino Acids (1) utilizing the analogues including reactive side chain groups with corresponding to medicaments as analogue corresponding therapeutic agents of L amino acids.

Such as, but not limited to the acetylation of the phenolic hydroxyol groups of tyrosine or serine, as an ester, by esterification or utilization ethyl alcohol as a reactant molecule with these hydroxyl groups forming ethers by etherification including chemical bonding with such component amino acids as serine, tyrosine, hydroxy glutamic acids. The resultant anti-inflammatory activity is analog to aspirin, acetyl salicylic acid, in structure and function of the acetyl group in that this grouping can inactivate the end serine grouping of the inflammatory prostaglandins synthesizing enzyme, prostaglandins synthetase. This action is lost in the non-acetylated salicylic acid.

(2) These reactive moieties side chain groupings and ionizable and very high-energy groupings may be utilized in an analogue therapeutic format and such as but not limited to groupings include guanidinium group of arginine, the beta carboxyl group aspartic acid, the thiol group of cysteine and the gamma carboxyl group of glutamic acid and the imidazole of histidine, the episolon amino group of lysine, the reactive phenyl group of phenylalanine and the reactive pyrrolidine of proline.

The high-energy alpha carboxyl groups and alpha amino groups of all the amino acids may all be used as reactive chemical; linkages to the other two components of this stem cell composition.

Phospholipids as P.C. or lyso lecithin with its available hydroxyl group and/or extracellular matrix components, such as, but not limited to, collagen or procollagen tropocollagen and its available hydroxyl groups as in hydroxyproline and hydroxylysine. These include all available chemical bonding techniques including condensation.

The hydroxylated fatty acids of ricinoleic and hydroxy stearate including but not limited to cyclic amino acids and cyclic fatty acids are also available such as but not limited to chalmougric and hydnocarpic fatty acids hybridizing by bonding to phospholipid lysolecithin such as ester or ether bonds. Also doable with the cyclic and/or hydroxylated amino acids.

The concept of treating plaque in a prevention at or active stage involves addressing the plaque as not being part and parcel of the metabolic metabolizable internal milieu or soluble internal milieu or a variant, of hydrophilic/lipophilic or more broadly expressed as hydrophilic/hydrophobic balance to permit rheologic flow and homeostatic internal milieu balance, immunologic-self internal milieu as is exemplified by subject composition and its components and reversing same by foregoing bonding technology as applied to subject composition and its components. These plaques may be best exemplified by atherosclerosis, Alzheimer's disease, inflammatory diseases, resistant chemoattractants in inflammatory disease, aging associated with progressive deficiency in phospholipid surfactant for example but not limited to phosphatidyl choline.

The universal donor essence of stem cell subject composition, when given orally may also be therapeutically and simultaneously stimulating oral tolerance to prevent and reverse progressive immuno-inflammatory organ damage reactions. These reactions further aggravate organ damage to such degree that the organ beings to deviate from self as in congenital biliary atresia. That in turn may already be mounting a rejection reaction. These are the steps that subject composition are preventing in averting the need for organ transplant. Should a transplant still be required, with oral tolerance so established and with the continuation of subject composition and its beneficial therapeutic effects will decrease the rejection mechanism, thereby decreasing the need for very high risk, life-time requirement of the anti-rejection armamentarium of medications.

In the prevention of rejection which occurs even in the most carefully HLA matched donor transplant, we find that even though the patient is normally replacing and re-replacing tissue and organ systems in an orderly progressive fashion every 2 to 3 months, the spark of rejection has been ignited and initiated and continues indefinitely even with this repeated spontaneous replacement with patient's own tissue and organ system. This knowledge emphasizes the importance of constantly preventing the rejection immune inflammatory conflagration from being initiated, as is being done with subject composition, as in congenital biliary atresia, working in concert with the gastrointestinal tract's oral tolerance, digestive enzymatic metabolic processing and solubilization, and HLB PC modulation by liver, gall bladder, biliary system.

Emphasizing the advantage in subject composition that are component analogue match of the diseased tissue and organ (such as but not limited to heart, lung and bronchopulmonary tract, and kidney urinary tract, liver, spleen, bone marrow, undergoing treatment). The criteria of components of subject composition also include being amenable to the body's metabolic processes, being readily solubilized in the internal milieu along with HLB modulation to practicalize solubility and extracellular matrix, cell membrane and/or intracellular delivery as required.

The neurologic degenerative diseases associated with aggregate proteins include, but are not limited to prion diseases—transmissible spongiform encephalitis derived from mad cow and allied diseases (aggregate/inclusions, of abnormal protein prion beta pleated sheet (PrPsc) non-metabolizable, resistant to the enzymatic activity of proteinase K. Abnormal protein deposits are seen histopathologically, instead of the normal alpha helix isoform (Pr Pc) normal brain proteins structure extracellular and not aggregate/non-inclusion and random coil normal structure extracellular brain protein. Alzheimer's has similar inclusion/aggregate beta pleated sheet, amyloid instead of the normal alpha helix and random coil normal structure and non-inclusion/non-aggregate extracellular brain protein. Insoluble nuclear brain protein aggregates are found in Huntington disease (the abnormal protein being Huntingtin protein) and spinocerebellar ataxia and (Ataxin) instead of the normal structure of trinucleotide repeats.

Parkinson's disease also has an abnormal protein alpha synuculein intracytoplasmic aggregate/inclusion. Lewy bodies instead of normal random coil repeat proteins structures, cancer with deficiency in HLB modulation and adequate surfactant required by DNA progress through normal rheologic flow required in mitosis with normal cellular and nuclear division and sharing of DNA genetic traits and the resultant formation of normal daughter cells. The darkly stained nuclear mitotic figures makes its appearance as an aggregate plaque or precipitate removed from the normal flow of nuclear function and the microcirculation of nuclear DNA genetic nuclear focus and originating cell division. Response to hydrophilic surfactant in vitro is supportive of this thesis (83 percent of the breast cancer cells were killed in 24 to 48 hours with exposure to 0.25 percent polysorbate 80, Tween 80). Again countering the poor solubility of the plaque-like mechanism disease which contributes to metabolization and the normal metabolic turnover of all cell tissue and organs brings about a disease-free therapeutic response. About one-third of these cancers are associated with inflammatory immunologic response T lymphocytic-plasma cell changes and are of poor prognosis. Response to HLB modulation towards a hydrophilic HLB has provided an 83 percent in-vitro encouraging response reported in other embodiment.

Another poorly metabolizable plaque producing substances of atherosclerosis are the trans fatty acids fats. These fats whose melting points are now significantly above body temperature and may be as high as 150 degrees Fahrenheit functioning as solid insoluble fats even though they may be as much as 20 percent unsaturated. For these two reasons they are not available to the internal milieu to be processed as self are a soluble metabolic team player, and therefore processed as foreign or foreign body likened with resultant plaque formation and atheromatous change and associated inflammatory changes.

With similar plaque disease mechanisms of insolubility, or insolubility aggregates, non-metabolizable, and immunologically foreign or nonself therefore maybe additionally be inclusive of pneumoconiosis such as but not limited to asbestosis (asbestos being a product of volcanic ash and igneous rock with a 5 fold increase in lung cancer with exposure to another product of combustion), tobacco smoke (an adverse synergistic catalyst, in a sense synergistically and pathologically additive as two products of combustion), exposure and now there is a 55 fold increase in lung cancer, silicosis and coal workers disease. This may be exemplified than not limited to asbestos, a volcanic ash fiber of silica calcium and magnesium therefore a product of a thoroughly burned rock derived product and not available for metabolic combustion, its insolubility has been estimated and extrapolated to be cells insoluble that is finally solubilized in more than 400 years of contact with water therefore foreign to tissue and immunologically non-self. Another insoluble crystal disease includes the insoluble uric acid crystals of gout (even though theoretically metabolizable).

Again, HLB modulation by enhancing hydrophilic solubility and more favorable hydrophilic/hydrophobic ratios should prove therapeutically useful. The use of PG PR to emulsify and disburse the fat and provide a lubricant for these physically abrasive sandpaper like crystals prior to hydrophilic solubilization.

These foregoing methodologies may be looked upon as basic principles of application technology and considerations in developing present and future pharmaceutical products. The fact that uric acid crystals are very soluble in glycerine, in contrast to marked insolubility in water and therefore in the fluids of tissue, may be used in therapy of gout starting with ½ to 1 teaspoon glycerine 3 to 4 times daily followed by a glass of water.

This anti-inflammatory activity in association with tissue healing activity of the L amino acids in subject composition Q101KC was successfully utilized in congenital biliary atresia (CBA) preoperatively in averting and saving the reported infant from a liver transplantation was reported along with the successful management of Crohn's disease in Girsh's patent applications and scientific exhibits presentations (exhibit 19). This antirejection pharmacodynamic activity is companion to and synergistic to the anti-inflammatory activity of the L amino acids analog and molar ratios to the cyclic oligopeptides amino acids of yclosporine and include the following L lysine, L alanine, L valine and glycine.

Also successful in anti-inflammatory tissue healing as well as anti-rejection activities reported in postoperative use in 11 patients by the Johns Hopkins pediatric surgery group as Q1 01 KC and as a similar source for subject composition L amino acids, alimentum. In CBA the patient's liver is so damaged by inflammatory disease and the integrity of immunologic self must be significantly modified and so may be looked upon by the body immunologically as foreign and significant rejection reaction must be a factor that was also reversed in the severe inflammatory response, yet associated with remarkable anti-inflammatory tissue healing activity of L amino acids of Q101KC. This associated antirejection activity must also have been present to reverse immunologic hypersensitivity states suspected not responsive to the very potent antirejection therapy being used in the 11 postoperative post transplantation Johns Hopkins pediatric surgical group CBA patients.

This union of biochemical essence in synergy and cosynergy into and/of biologic structures companion to their function and multiplicity of functions applied to anti-inflammatory activity and healing is as unique and analog and structured function as the government United States of America and progressive union of structure from borough to township to city to state to federal government as well as synergistic function and multiplicity of functions and is highly unique in contrast to what is available with those skilled in the art(s). These biochemical essence of subject composition are not only analog to these organizational systems as well as analog to therapeutic medications reactive high-energy side groupings as well as ionic groupings of stem cell result in and continue in perpetuation to the production of cell and the embryonic stem forming extracellular matrix tissue, organ systems, and vital organs are all under cooperative control of the central and peripheral nervous system autonomic nervous system, immunologic systems, nervous system like memory, and neural hormonal systems.

While not wishing to be bound to any theory, this tetrahedral 3-D spatial conformation is also evident not only in the L amino confirmation and glycine but also in these two carbon molecular two carbon bridges which also separate and keep the aromatic amino acids in this 3D tetrahedral formations. A distinctive from the planar benzene ring 3-D conformation that stack and slide one upon the other subject composition and its components are also analogue to and mimic the non-covalent bonding technology resulting in the elaborate cellular architecture visible in the electron micrographs of mammalian and human tissue and human stem cell tissue mimicking in being analogue to the most important non-covalent chemical bonding of human tissue and human stem cell tissue.

It is interesting and highly applicable to note that the phosphate molecule so pervasive in all metabolic activities is also tetrahedral in 3-D shape and could very well represent the reason for glucose and fructose phosphorylation as glucose six phosphate, fructose six phosphate, fructose 1 6 phosphate as a structural bioengineering fit and therefore functional fit in the utilization of glucose in energy production and release to the body suggesting advantages to these analogue 3-D tetrahedral spatial fit in the therapy of diseases such as but not limited to diabetes mellitus.

Subject composition and its component L. amino acids and glycine is analogue and mimics not only in structure and function anti-inflammatory drugs such as but not limited to NSAID, 5ASA, (Exhibit #5, 5a, 10, 3), as well as being analogue and mimicking anti-rejection medication such a cyclosporin, but also is analogue and mimics in structure and function human tissue, specifically also analogue and mimics the newest forefront of pharmacologic therapy, the human stem cell, (while not requiring human tissue, requiring only its biochemical equivalent essence as illustrated in prior embodiments). In this case also stimulating, activating and facilitating tissue healing and tissue protein synthesis and re-synthesis, and of molar ratios analogue to and mimicking human tissue. The subject therapeutic composition is thereby also analogue to biochemical and immunologic self and thereby minimizes potential adverse side effects.

The bioengineering therapy at a molecular level therefore requires providing this stereochemical 3D fit of L amino acids and glycine therapeutic subject composition. This stereo biochemical fit into the DNA, ribosome, transcription of tissue healing also maximizes the therapeutic fit and therefore therapeutic activity of the L amino acids and glycine reactive high energy ionizing side chain that stimulates the simultaneous overlap and continuum as conjoint therapeutic activity, exemplified but not limited to, anti-inflammatory tissue repair protein synthesis activity. These 3D conjoint therapeutic activities are further synergistically enhanced by HLB modulation to insure the best biomolecular therapeutic targeted fit required for cell membrane and for cell delivery system and/or extracellular matrix delivery synergistically adaptable to disease in question as the newest stem cell therapy.

To best synergize these therapeutic healing activities with current and future medications while simultaneously fulfilling these bio-molecular tissue 3D fit needs, the following requirements must be fulfilled: (a) by using the foregoing stereo biochemical L or Levo optical rotation of light and energy and alpha amino, alpha carboxylic side chain ionizing groups, as free L amino acids and glycine's structural back bone with their therapeutic ionizing high energy side chains with additional synergy by adding further therapeutic side chains and therapeutic moieties such as, but not limited to, the acetyl radical or the indole radical, (b) by adding current or future medications to bond biochemically by hydrogen bonding, van der Waals forces electrostatic and zwitterion forces. (c) by covalent or valent chemical bonding or bridging of current or future medications to items as described in subject composition in (b), and (d) by biochemical and bioengineering bonding the biochemical therapeutic moieties to (a and/or b and/or c).

In the bioengineering design of a medication to be analogue to human tissue and to human stem cell, (the most advanced forefront of pharmaceutical therapy), the most common and most abundant bonding forces of human tissue is the non-covalent bonding force of human tissue and therefore of subject composition analogue to and mimicking human tissue and stem cell and biochemical essence of stem cell. It is not taught in the prior art that subject composition biochemical components, extracts and essence of non-human tissue and non-human tissue stem cells can non-covalently bond and result in human tissue signaling systems analogue to human stem cells resulting in a combination of several therapeutic effects including but not limited to anti-inflammatory effects, overlay and continuum of disease tissue healing effects, and tissue protein synthesis in re-synthesis in healing diseased tissue.

It is this flexible access to healing that makes non-covalent bonding so important in tissue healing and tissue protein synthesis and re-synthesis, it is this very weakness (10 to 100 times weaker in kilojoules per mole) of these non-covalent bonds that allows them to be repeatedly and continually broken and repeatedly and continually reformed in the dynamic interplay that is life, health, and tissue healing.

This continual and repeated interplay depends on rapid interchange of molecular partners which could not occur if intermolecular bond forces as in the case of valent and covalent bonding are so fixed and rigid as to lock the molecules up in a rigid inflexible intermolecular conformation to obstruct a very flexible availability as in subject composition so important in a therapeutic medication as in these subject composition embodiments in tissue healing, protein synthesis and resynthesis healing offered so unique to this subject composition, the use of non-covalent bonding (Covalent bonds of 300 to 400 kilojoules per mole are exemplified by but not limited to carbon-carbon bonding and carbon-hydrogen bonding and present in the aromatic and aliphatic carbon chains of L amino acids and glycine of subject composition).

Covalent bonding is similar to bonding currently available in synthesized medications. Further examples of non-covalent bonding application technology of subject composition in molecular bio engineering in tissue healing and cell, tissue and organ reconstruction and reconstructive repair of cellular, tissue and organ disease. The efforts dedicated to the healthcare and pharmaceutical industry mission to utilize, such subject composition in healing of disease and reversal to normal of cellular, tissue and organ disease along with protein synthesis and resynthesis in diseased tissue repair utilizing subject composition in non-covalent bonding associated with (1.) DNA (2.) the protein molecule (3.) the macro molecular protein superstructure of the cell, tissue and organ in heeling. The therapeutic application such as but not limited to the non-covalent bonds as presented therapeutically in subject composition available in subject compos Won to stabilize:

(1.) DNA's interaction between different parts of the strands of the structural and functional DNA macromolecule composed of linear sequenced (and covalently bonded) nucleotide residues.

(2.) Proteins all made up of covalently bonded amino acids (similar in many respects, and being in actuality a transcriptive reflection of the DNA and RNA template of the macro molecule DNA) are folded into specific 3 D molecular informational as well as conformational arrangements by non-covalent bonding energy forces as available in subject composition and utilized in many embodiments presented for tissue healing and tissue proteins synthesis and resynthesis.

The many non-covalent interactions provided by subject composition which stimulated, facilitated, accelerated, activated and synergized by subject compositions non-covalent bonding activity in an analogue and mimicking fashion to human tissue and human stem cell tissue and the biochemical essence of stem cell as utilized in subject composition.

(3.) Subject composition stimulates facilitates accelerated activates proteins interaction with other protein molecules or with other macromolecules such as DNA to form even higher levels of organization leading to the healing of cell, tissue, and organ of diseased cells, tissue and organs there such as but not limited to the application of subject compositions biotechnology to inflammation provides healing formation tissue healing protein synthesis and resynthesis in healing and reformation of a disease.

While not wishing to be bound to any theory this non-covalent bonding support by subject therapeutic composition of macromolecules such as but not limited to foregoing embodiments (1.), (2.), and (3.) DNA, RNA and resulting transcription protein appears to be a form of noninvasive DNA bio-engineering with minimum if any risk factor in patients such as but not limited to Crohn's disease and pediatric Crohn's disease where hereditary factors are suspected in playing a significant role.

(e.) However, microorganism, (such as but not limited to fungal) derived medications may contain the D amino acid components such as but not limited to cyclosporin, designed for humans and animals, however may not be metabolizable with the presence of L amino acid enzymes and the absence of D amino acid enzymes in humans and animals. These D amino acid components are not readily metabolizable therefore a factor in recognition of biochemical and immunologic self and therefore predisposing to adverse side effects.

This risk factor may be exemplified by the anti-rejection therapeutic agent oligopeptide cyclosporin with the multiplicity of major side effects including the 20 percent risk of loss of renal function contain the D alanine amino acid, which is also found in microorganism (bacterial) cell wall along with D glutamate components of microorganism polypeptides Therefore, resynthesis of such valuable drugs as cyclosporin would be value with subject composition components as illustrated but not limited to subject composition generic code Q101KC, by substituting L alanine for microorganism derived D alanine would make this drug more compatible in bioengineering to biomolecular self and to immunologic self identity thereby greatly reducing the risk, major adverse reactions such as 20 percent loss in renal function. This advantage is also offered by subject composition with its L amino acids and glycine in molar ratio with cyclosporin such as glycine, L alanine, L valine, L leucine and gamma amino butyric acid along with methyl donors such as, but not limited to, methionine and betaine, with its ability to function as an anti-rejection pharmaceutical activity in vivo. This subject composition analogue mimicking of such structure and function as cyclosporin may come about by the in vivo resynthesis of cyclosporin with L alanine instead of D alanine or by synthesis stimulation facilitation or acceleration of the pharmacologic effects of and metabolite effects of cyclosporin and or by using methodology of and including non-covalent bonding of subject composition such as but not limited to embodiments of application technology.

These methodologies will provide therapeutically efficacious, minimum risk drugs for diseases such as but not limited to pediatric Crohn's disease or congenital biliary atresia and their major complicating subsets, that is the same drug as patent pending subject composition.

Subject composition generic code Q101KC contains components, optionally in molar ratios similar to, that provide for specific application as anti-inflammatory therapeutic agents comprising free L amino acids and the optically inactive (non D non L) amino acid glycine, and specified molar ratios analogue and mimicking human tissue, that is both analogue to and mimicking NSAID (including Vioxx and Celebrex, the newest NSAID) and synthetic amino acid 5ASA and NSAID anti-inflammatory drug, anti-rejection medication (more specific to 5ASA in being analogue and mimicking anti-rejection drug cyclosporin), while at the same time as well as being analogue and mimicking human tissue and human stem cell tissue and stimulating, activating and facilitating tissue healing, disease repair, and tissue protein synthesis and resynthesis, L amino acids and amino acid glycine (optically inactive neither L nor D) analogue not only in structure and function to NSAID, 5ASA but also analogue and mimicking in structure and function human tissue. Specifically the subject composition is also analogue to, and mimicks, the newest agent at the forefront of pharmacologic therapy, the human stem cell, (while not requiring human tissue), in this case also stimulating, activating and facilitating tissue healing and tissue protein synthesis and resynthesis, and of molar ratios analogue to and mimicking human tissue. Q101KC therapeutic composition is thereby also analogue to biochemical and immunologic self and thereby minimizes potential adverse side effects. The L amino acids and glycine amino acid, including both aromatic and aliphatic amino acids of Q101KC, clearly delineated and well documented by controlled studies regarding efficacy and scientific rationale as presented. The aromatic amino acids of Q101KC are analogue and mimic medication in function and structure of the aromatic amine synergism of triple sulfonamides as well as the other L amino acids and glycine.

In this specific application for drug designation the amino acids should be available entirely as therapeutically active free L amino acids and non L or D glycine amino acid and, therefore, should be free of such residual polymers as hydrolyzed protein source peptides.

To recapitulate such therapeutic activities such as but not limited to: not only anti-inflammatory (such as but not limited to NSAID, 5ASA) anti-rejection (such as but not limited to cyclosporin), synergistic activity but uniquely also, analogue to and mimicking tissue healing, tissue proteins synthesis, tissue protein resynthesis. Added advantages and highly competitive to the corticosteroids include cumulative beneficial healed tissue effect, the lack of relapse with stopping this medication for as long as six months, one year, even longer, exhibits #1 through #20. As set forth in Exhibits 1-21, PCD denotes Crohn's disease; CBA denotes congenital biliary atresia; and Q101KC is a designation for the compositions of the subject application (e.g., NEOCATE or VIVONEX).

Such a therapeutic result is possible in view of the biochemical and pharmacologic structure and function of a component for example but not limited to the L amino acids and optically inactive (non D and non L) amino acid glycine offering medical and veterinary practice a competitive edge over microorganisms of very primitive background and origin. However, microorganism, (fungal) derived medications may contain the D amino acid components designed for humans and animals with the presence of L amino acid enzymes and the absence of D amino acid enzymes in humans and animals, these components are not readily metabolizable therefore a factor in recognition of biochemical and immunologic self and therefore predisposing to adverse side effects.

This risk factor may be exemplified by the anti-rejection therapeutic agent oligopeptide cyclosporin with the multiplicity of major side effects including the 20 Percent risk of loss of renal function contain the D alanine amino acid, which is also found in microorganism (bacterial) cell wail along with D glutamate components of microorganism polypeptides.

Further incorporated in this structure exemplified by, but not limited to, the aromatic amine t. amino acids and non D non L glycine: is that the high energy benzene ring is always separated from the amine or amino high energy group by a 2 carbon ethyl grouping (bridge like biochemical separator) whereas the aniline dye, coal tar potentially toxic and benzene ring derived biochemical compounds exhibit 10 are directly attached to the benzene ring with other groupings attached in the ortho, meta, or para positions are dissimilar to biochemical and/or immunologic identity as self and as expected have a high incidence of adverse side effects. These adverse side effects can be minimized or avoided by using the aromatic amines or other benzene ring derivative medications with subject composition as a protective shield, or by deriving such medicines such as but not limited to anti-inflammatory 5ASA a synthetic amino acid NSAID, and the newest anti-inflammatory medications such as but not limited to Vioxx and Celebrex from the synthetic L amino acids and non L non D glycine amino acid. This may be accomplished by biochemical bonding reactions such as, but not limited to acetylation or hydroxylation first followed by acetylation. in addition to etherification, condensation, condensation and amination chemical reactions may be applied to obtain these safer derivatives.

To recapitulate: in medical or veterinarian therapy one would strive for therapy greatly minimizing the risk or in most cases completely avoiding the risk of major or minor adverse side effects. was such therapeutic activities such as but not limited to: not only anti-inflammatory (such as but not limited to NSAID, 5 ASA) anti-rejection (such as but not limited to cyclosporin), synergistic activity but uniquely also, analogue to and mimicking tissue healing, tissue, proteins synthesis, tissue proteins on resynthesis.

Added advantages and highly competitive to the corticosteroids include cumulative beneficial healed tissue effect, the lack of relapse with stopping this medication for as long as six months, one year, even longer (exhibits #1 through #20). Such a therapeutic result is possible in view of the biochemical and pharmacologic structure and function of a component for example but not limited to, the L amino acids and non D and non L amino acid glycine over microorganisms of very primitive background and origin. For example microorganism, (fungal) derived oligopeptide cyclosporin with the multiplicity of major side effects including the 20 percent risk of loss of renal function, D glutamic acid, D alanine both microorganism and (bacterial) cell wall components of polypeptide.

Further incorporated in this structure exemplified by, but not limited to, the aromatic amine L amino acids and non D non L glycine: is that the high energy benzene ring which is always separated from the amine or amino high energy group by a 2 carbon ethyl grouping (bridge like biochemical separator); whereas the aniline dye, coal tar potentially toxic and benzene ring derived biochemical compounds are directly attached to the benzene ring with other groupings attached in the ortho, meta, or para positions are dissimilar to biochemical and/or immunologic identity as self and as expected have a high incidence of adverse side effects.

These adverse side effects can be minimized or avoided along with adding tissue healing effects not already present by using the aromatic amines or other benzene ring derivative medications along with subject composition as a protective shield, or by deriving such medicines such as but not limited to anti-inflammatory 5 ASA a synthetic amino acid NSAID, and the newest anti-inflammatory medications such as but not limited to Vioxx and Celebrex from the synthetic L amino acids and non L non D glycine amino acid (above methodology of a to e).

This may also be accomplished by bonding L amino acids to these existing NSAID or 5ASA Vioxx Celebrex by acetylation or hydroxylation first followed by acetylation. in addition to esterification, etherification, condensation amination and/or transamination chemical reactions may be applied to obtain these safer derivatives. Additionally further pharmaceutical advantageous therapeutic functional properties may be added to L amino acids and glycine may be added by bonding pharmaceutical active moieties by such chemical bonding methods including but not limited to the foregoing. On further analysis these biochemical structures and associated functions serve as a basis for this unique pharmacologic function of healing and the stimulation, facilitation, acceleration of healing.

These structures are based on the biomolecular analogue mimicking and therefore biochemical and immunologic identifying features of self as a basis for minimizing adverse reactions are also present This has not been taught in the prior art By aminating the alpha carbon (that is the second carbon next to the carboxylic acid) the organic acid derivatives that also has the anti-inflammatory (for example but not limited to naproxen or ibuprofen or other anti-inflammatory propionic acid derivatives, anti-inflammatory butyric acid derivatives, anti-inflammatory caproic acid or other 2, 3, 4, 5 organic acid anti-inflammatory derivatives) biomolecular properties (or other outstanding pharmacologic properties) the biomolecular tissue heating tissue protein synthesis and resynthesis therapeutic properties are now hereby added to the therapeutic activity of the medicament This is particularly reinforced as the molecule is in the 3D L chiral (optical levorotary form) and already existent if the base starting molecule is already an existing L amino acid. Whereas, if the base starting molecule is a 2, 3, 4, 5 or 6 carbon organic acid it is preferable that the chemical process of alpha carbon amination is so provided to include only the L chiral (optically levorotary form). Thereby using these principles of biomolecular engineering the opportunity is being offered here to add tissue healing qualities to any medication or potential medication in addition to reducing the risk of adverse side effects including maintaining a biochemical self as well as an immunologic self identity as well as a very valuable cumulative effect even after the medication is stopped, therefore highly advantageous and competitive over corticosteroids.

While not wishing to be bound to any theory the tendency of the benzene ring and its therapeutic derivatives to stack and not be involved in the tissue healing thread associated with tissue proteins synthesis and resynthesis may help to explain the fundamental differences in the lack of tissue healing efficacy and adverse side effects versus 3-D L amino acids and glycine. This chiral asymmetry of the L. amino acids in the subnuclear electron behavioral activity, gives electrons emitted (in beta decay) a left-handed spin in free L amino acids and glycine therapeutically. Therapeutically also gives higher form of life such as but not limited to humans a strategic advantage and often critical competitive advantage over primitive microorganisms for example in the biomolecular homeostatic internal milieu of health vs. disease.

Therefore, resynthesis of such valuable drugs as cyclosporin with L alanine substituting for D alanine would make this drug more compatible in bioengineering to biomolecular self and to immunologic self identity thereby greatly reducing the risk, major adverse reactions such as 20 percent loss in renal function. This advantage is also offered by subject composition with its L amino acids and glycine in molar ratio with cyclosporin such as glycine, L alanine, L valine, L leucine and to L gamma amino butyric acid with its ability to function as an anti-rejection pharmaceutical activity in vivo. This subject composition analogue mimicking of such structure and function as cyclosporin may come about by the in vivo resynthesis of cyclosporin with L alanine instead of D alanine or by synthesis stimulation facilitation or acceleration of the pharmacologic effects of and metabolite effects of cyclosporin.

Again, while not wishing to be bound to any theory, the tendency of the benzene ring and its therapeutic derivatives to stack and not be involved in the tissue healing thread associated with tissue proteins, synthesis and resynthesis, necessary for recovery, may help to explain the fundamental differences in the lack of tissue healing efficacy and adverse side effects in contrast to the above-mentioned 3D effects of the L amino acids. (in contrast these stacked planar benzene ring molecules function as electron clouds whose fluctuating force cause the planar molecules to slide, without touching, one upon the other)

This 3-D effects can be even further synergized by advantageous HLB modulation for example HLB of 18 to 20 respectively, 0.25 percent to 0.5 percent such as Tween 80 or sodium lauryl sulfate in the face of severe infection, locally or systemically and poorly responsive or completely unresponsive to antibiotic (which can be documented further, in each case, by comparative bacteriologic studies) including antibiotic sensitivity and staining characteristics before and after HLB modulation can be used to inactivate lipids, lipoproteins, such as, but not limited to, lipid A (glycolipid endotoxic activity) and weaken the microorganisms (such as but not limited to bacteria, viruses, and/or fungal pathogens and their products) cell wail offensive microorganisms such as but not limited to therapeutically challenging microorganisms such as but not limited to *E. coli, Pseudomonas aeruginosa,* anthrax and its spores—or protein lipopolysaccharide tuberculin cell wall tuberculin of *mycobacterium tuberculosis,* (or resistant *mycobacterium tuberculosis* and its lipopolysaccharide cell wall, as occurs for example in HIV infections). Viral infections including HIV efficacy results from the respective enhancement of so-treated (IHLB modulation) antibiotics which can by HLB modulation, be made more been penetrable and efficacious.

This treatment can be preceded by the HLB of 2, 0.25 percent to 1 percent, PGPR (polyglyceryl polyricinolate) as an aid in disbursing the microorganism's cell wall fat and make it more available to foregoing high HLB therapy. In other embodiments this has also been shown to reduce the pathogenicity and specificity of the allergenic pathogens.

Successful anticancer therapeutic activity cancer tissue cell in vitro' breast cancer cell suspension comparative trials with treatment with 0.25 percent to 0.5 percent polysorbate 80 (Mean 80) with 83 percent reduction in 24 to 48 hours of cancer cell mitochondrial activity after HLB modulation with tween 80, and 50 percent reduction in cancer cells' abnormal morphology and abnormal mitosis on cytopathologic review. This high HLB therapy of 18 with, Tween 80 could have been mediated and had an antiviral effect on potential oncogenes, or countered a lipophilic carcinogen by reducing its lipophilic pathogenicity or could have permitted a more normal flow of nuclear chromosomal fluidity (prior embodiments have shown mitotic figures in the nucleus to appear as plaque like precipitates, with interference with normal rheologic nuclear cell division flow) much higher hydrophilicity is required in more normalized cell division in mitosis by adding deficient hydrophilic surfactant required for normal mitosis.

Not taught in the prior art:

Current therapeutic agents such as but not limited to the anti-inflammatory agents lack a tissue healing component. This is in sharp contrast to the anti-inflammatory therapeutic L amino acid glycine components of subject composition which have a dual action ant-inflammatory and tissue healing bonded bridge. The primary pharmaceutical molecular differences are illustrated here in exhibits 3 and 10.

1. There is a two carbon ethyl bridge separating the aromatic amino acid high-energy benzene ring from its amino side chain group (Exhibit 3) whereas in exhibit 10 the anti-inflammatory acetaminophen compound derived from aniline (and historically the aniline dye industry and coal tar industry), and other pharmaceutical derivatives such as but not limited to those shown here are lacking in this ethyl two carbon breech separating the amino group from the high-energy benzene ring anti-inflammatory aromatic amine compounds so bonded with a 2 carbon ethyl bridge should enhance the tissue healing efficacy of these compounds (not only not present but actually without this two carbon ethyl there is not only an absence of tissue healing effect but actually an inhibition of tissue healing effect.

2. In exhibit 3 in the case of the propionic acid anti-inflammatory derivatives there is no amino group on the second (or Alpha) carbon for example ibuprofen or naproxen, and as there is in the eight propionic acid derivatives anti-inflammatory function L amino acids of subject composition have coexistent amino groups on the second or Alpha carbon imparting to these compounds the tissue healing pharmaceutical function.

In bioengineering future pharmaceutical compounds such as, but not limited to, anti-inflammatory propionic acid derivatives and amino group could be bonded to this site endowing these compounds with the additional tissue healing pharmaceutical function of subject composition (not only not present in current anti-inflammatory propionic acid derivatives but these current pharmaceutical compounds have an inhibitory effect on tissue healing).

This continuum of the inflammatory disruptive and destructive conflagration of disease proceeding to healing resolution (also an overlay of healing resolution) may be mediated by free L amino acids of the subject composition (herein referred to as Q1 01 KC). This destructive inflammatory process is expressed by the protease enzymes secreted by the neutrophil. This conflagrative inflammation of PCD (pediatric Crohn's disease) was originally triggered by a chemoattractant response to injury and disease, foreign and non-self immunologically, and has demonstrated by in vitro preclinical and in vivo controlled clinical studies in a total of more than 250 patients has demonstrated the efficacy of free L amino acid subject composition turnoff signaling switch of free L amino acids in subject composition Q101KC. And in the present application 5 to 15 grams dry weight (15.5 percent free L amino acids and glycine, or 775 mg, and analogue in 800 mg dosage of synthetic amino acid 5 amino salicylic acid, to 2, 325 mg free L amino acids) in addition to free L amino acid produced by neutrophil enzymatic action in to the therapeutic subject composition resulting stockpile of free L amino acids which in turn provides a simultaneous positive protein synthesis stimulus of replacement of damaged tissue under DNA guidance by the endoplasmic reticulum resynthesis of tissue protein associated with healing resolution. The PCD and CBA patients may now be grateful for the effective non-steroidal therapy now available with documented steroid-sparing actions.

With stimulus switch-off signaling mechanism the newly released neutrophils are stimulated to leave the bone marrow to enter the inflammatory inflammatory PCD site tracked by permeability test (exhibits 2, 1, and 12), simultaneously with the need for response to tissue injury stimulus turned off, the existing neutrophils will migrate back to the reticulo endothelial system sites as seen in the permeability studies (liver and spleen).

Simultaneously again, with the autolytic enzymatic digestive response of the neutrophil silenced, the tissue healing resolution to former integrity is initiated, again with the stimulus of the added dosages of L amino acid, Q10 01 KC by way of the law of mass action promoting stimulus for resynthesis of tissue protein.

In addition to including free L amino acids analogue to and in molar concentrations of tissue as the biochemical essence of protoplasm in the embryonic stem cell subject composition, two other analogue categories of components, are included, which are also recognized as self and include the biochemical essence of cell membrane phospholipid such as but not limited to phosphatidyl choline, and extracellular matrix including, but not limited to, the first biochemical substance embryonic stem cells produce the extracellular matrix including but not limited to collagen (these components of subject composition are available as currently marketed products available for healing resolution of disease). The phospholipids such as phosphatidyl choline self vesiculates and provides cell membrane restoration as the biochemical essence of cell membrane in PCD and CBA.

This self vesiculating membrane restoration is synergistically aided in cell membrane repair, furthered by the free L amino acids of Q1 01 KC subject composition particularly glycine. Collagen, the extracellular matrix and the first biochemical substance embryonic stem cells produce, contains and is enmeshed and entwined in growth factors, and also offers, intrinsic to its structure, analogue computer software all tissue such as human tissue structure and function. Compositely as embryonic stem cell therapeutic composition and as individual components, these components are well-tolerated components and are looked upon by the body immunologically as self. (Whereas other therapeutic agents in their pharmacodynamics and pharmacokinetics are not bioengineered as analogue to human tissue and are therefore not recognized as self and may in the future be significantly enhanced with the use of this paradigm of pharmacodynamic and pharmacokinetic analogue of bioengineering design and therapeutic cell functioning design.) In fact if they have not been specially bioengineered for the inflammatory immune response overlay and continuum of healing resolution cycle, they may be looked upon or interpreted as foreign by the body's response to injury system. For example but not limited to NSAID such as indomethacin or aspirin wherein protein synthesis is inhibited and in the case of indomethacin neutrophil motility is also inhibited, this, of course includes protein required for healing preventing the normal retreat of neutrophil anti-inflammatory turn off signal. The anti-inflammatory corticosteroids are well recognized for their interference with the healing cycle. Therapeutic agents which are not bioengineered to complete the therapeutics of the healing resolution process of inflammation, and are viewed by the body's immune inflammatory response system as foreign and their pharmacodynamic substance and metabolites represent the body's response to an injury and therefore, as we might expect, adverse reactions are also listed as possible occurrences.

The Q101KC subject composition stem cell as a delivery system analogue to immunologic concept-self.

In contrast, this newly created subject therapeutic composition biochemical stem cell is representative of self and may serve as a delivery system for other therapeutic agents to be fit in and be looked upon by the body's response system advantageously as self. This will offer other therapeutic agents the opportunity to be looked upon as self in this delivery system and minimize adverse reactions and may herein and hereby be looked upon as self by the body's response system. Thus, in recapitulation and review the first component that is representative of subject composition L amino acid as well as being the product of the neutrophil enzymatic protective activity system now with these administered added dosages permits the neutrophil's inflammatory "friendly fire" to stop and the abnormal PCD inflammatory in vivo permeability test response, tracked by the radioactively tagged neutrophils (as well as in vitro studies documenting anti-inflammatory response of subject composition) now return to non-inflammatory normal tissue status and proceed to completion of the healing resolution cycle.

With stimulus switch-off signaling mechanism no new neutrophils are stimulated to leave the bone marrow to enter the inflammatory PCD site tracked by permeability test (18 references) simultaneously with the need for response to tissue injury stimulus turned off the existing neutrophils will migrate to the reticulo endothelial system sites as seen in the permeability studies (liver and spleen). Simultaneously again, with the autolytic enzymatic digestive response of the neutrophil silenced the tissue healing resolution to former integrity is initiated, again with the stimulus of the added dosages of L amino acid, Q101KC by way of the law of mass action promoting stimulus for resynthesis of tissue protein.

Accordingly, 85% of the patients are symptom free within 4 weeks associated with normal radiographs of radio-actively tagged neutrophil permeability test (in contrast to abnormal radiographs prior to initiating free L amino acid Q1 01 KC subject composition therapy. This product is available on the market as infant formulation with 15.5% amino acids which composition is analogue and molar ratio analogue to human tissue and plasma and was specifically designed to mimic human holocrine tissue (in the form of breast milk whereby the entire cell contents of the mammary tissue is secreted). Available here with analogue to the immunologic concept of self, in the form of free L amino acid associated with high energy ionizable side chain groups available for tissue resynthesis to former integrity healing resolution of tissue.

Neutrophils—Permeability

Lipopolysaccharides, a common neutrophil attractant, derived from and bacterial products such as bacterial endotoxins or exotoxins and may be deactivated by modification of HLB hydrophilic lipophilic balance by hydrophilic surfactant activity such as but not limited to the 8 propionic acid L amino acids (all but phenylalanine) of subject composition (other hydrophilic surfactants may be alternatively used such as but not limited to polysorbate 80, or sodium lauryl sulfate).

This application technology is made possible by the dramatic difference of L amino acids with a molecular weight of 100 or 200 vs. its parent molecule which can be exemplified by a molecular weight of 100,000. In which case 500 to 1000 alpha amino groups and in 500 to 1,000 carboxyl groups are now available in contrast to one alpha group and one carboxyl group in a parent printing molecule of 100,000 molecular weight. Dramatically illustrating the different reaction potentials now available with a therapeutic L amino acid subject composition. This same illustration is applicable for hydrophilic moieties and reactive side chain groupings as in the case said the seven propionic acids.

A biochemical therapeutic subject composition of essence of functional stem cell mimics embryonic stem cell with its pluripotent activity accelerates, facilitates, activates, stimulates, and evokes stem cell activity, and this therapeutic stem cell composition in tissue injury and disease mimics normal tissue, is present analog to human tissue and in analog molar ratios of human tissue and stimulates the suppression of inflammation, stimulates and promotes healing, and avoids per se their requirements are necessity of the introduction of foreign are nonself rejection and rejection like and linked components and adverse reactions thereof, is sourced from biochemical and immunological essence in common across species. While at the same time permits newly required medications to be utilized and protected in an envelope delivery system like mantle or cover including L amino acids and amino acid glycine as non-covalent bonding mechanism giving macromolecules such as DNA and protein shielding these medications from foreign and nonself haptene like recognition thereby greatly minimizing adverse reactions.

In animal husbandry we see an analog system or marker of immunologic self applied to springtime lambing. If an ewe or female sheep dies at birthing its offspring lamb, the chosen surrogate mother's placental blood is used as a marker for this orphaned newborn lamb for her to adopt, so that she will accept this newborn lamb as immunologic self and breast-feed it along with her own newborn lambs.

Analogue to this, in preparing donor organ for acceptance in transplantation, subject composition patient's blood may be used, as an organ bath and organ infusion to minimize rejection thereby as for example in CBA.

Therapeutic anti-inflammatory activity is no longer present when presented as intact food such as the proteins of milk such as casein or whey. When free L and amino acids in this therapeutic composition are synthetically prepared analog to human tissue and analog to molar ratios of human tissue their function as significant anti-inflammatory agents suppressing cytokine stimulation of the inflammatory reaction and antagonist to the receptors of the inflammatory reaction results.

The biochemical essence and essence of function of stem cell such as but not limited to the exemplification and mimicking human tissue and protoplasm such as holocrine tissue such as but not limited to mammary tissue that pioneered cloning. L amino acids analog to human tissue and analog molar ratio synergistically combining further with the first extracellular matrix biochemical muco-polysaccharide produced by cleavage of the fertilized ovum as embryonic stem cell and further synergistically combined with phospholipid (self vesiculating essence of cell membrane).

These free L amino acids and their reactive side chain groupings and ionizing groupings are also analog to the synthetic therapeutic (therapeutically active mainstay of PCD) amino acid five ASA and active anti-inflammatory component of sulfasalazine exemplified by tyrosine and its phenolic hydroxyl groupings along with synergistic effect of acetyl grouping of glycine completing the functional and structural grouping anti-inflammatory tissue healing analog. Simultaneously the same L amino acids tyrosine and its phenolic hydroxyl grouping co-analogs to the propionic acid derivative anti-inflammatory drugs such as ibuprofen and naproxen and their distinguishing acyl side grouping and is in these L amino acids are also on its alpha (second) carbon acyl grouping representing the high-energy alpha amino grouping in the case of the L amino acids.

It will be recalled that all amino acids are ordinary organic acids which have an amino grouping in the molecule. It will also be recalled that the second carbon atom, which is also next to the carboxylic acid group is called the alpha carbon atom. This is also exemplified by tyrosine, cited here, as one of the 8 propionic acid derivative L amino acids.

Further exemplified such as but not limited to analog to acetyl salicylic acid with the analog acetyl reactive side chain grouping of the acetyl grouping of alpha amino acetic acid of glycine alone with the hydroxyl phenolic grouping of tyrosine. This is further exemplified metabolically and pharmacodynamically and pharmacokinetically such as but not limited to glycine conjugate intermediary metabolites of acetyl salicylic acid.

To make this subject composition more palatable, in fact even pleasant tasting per taste panel review—and therefore overcoming the very unpalatable taste that has led to 15 to 20% non-compliance and the requirement of a nasogastric tube to administer this very beneficial anti-inflammatory, anti-rejection stimulating, facilitation, accelerating, synergizing, healing tissue protein synthesis therapy. In the management of one of the most resistant, fraught with complications such as, but not limited to, Crohn's disease. Use of subject composition in congenital biliary atresia enables bringing about the reversal of these diseases with subject composition. In these cases as far as the non-compliance patients are concerned, the advances in flavor are as important as the advances in the product.

This savoring flavor may also include and may be obtained by flavors such as, but not limited to, savoring soup flavors such as but not limited to, vegetable soup, asparagus soup, broccoli soup, cucumber, and celery and/or pea soup, beef, fish and seafood. The concentrated flavor as found in a bouillon cube, as found in Wyler's granules chicken flavor, Borden's Foods Corp. Columbus, Ohio for this application technology.

The required dosage (5 gm. To 15 gm) was mixed in a in water that had been pre-warmed (lukewarm, with a drop test on the forearm) spring or distilled water, in the microwave oven for approximately 35 seconds together with ⅓ or ½ of a 4 gram bouillon cube (chicken in this example) resulted in a creamy chicken soup flavor. This flavor system addresses the compliance issue and therapeutically successful use of subject composition in Crohn's disease as cited in previous embodiments. Such Crohn's disease patient has continued to do well with this pleasantly flavored subject a composition.) Bouillon cube utilized, Hormel brand, Austin, Minn.

Subject composition and all its components and therapeutic stem cell components including but not limited to components that stimulate, facilitate, accelerate and synergize in vivo including but not limited to human and also applicable to all mammalian stem cell. Subject composition included here by reference of patent application Ser. No. 09/629,859 including L amino acids and glycine, phospholipids such as but not limited to phosphatidylcholine, extracellular matrix such as but not limited to collagen, including the collagen subtypes of vertebrates but not limited to collagen I to X, fibronectin and its collagen specific protective effects (from collagenase) binding sites, including but not limited to other collagenase inhibitors such as alpha 2 macroglobulin and beta I macroglobulin, chondroitin sulfate, glucosamine, mucopolysaccharides, mucoproteins, elastin, the components of basement membrane including but not limited to collagen type IV, laminin, entactin, heparin sulfate with its characteristic high anionic charge surfactant activity playing a major role in glomerular filtration.

A remarkable amount of tissue organization of subject composition and its components that has been downloaded into, for example but not limited to, the extracellular matrix components of subject composition (growth factors are commonly enmeshed and interwoven in extracellular matrix or maybe optionally added in specialized therapeutic use of subject composition, and (exemplified in Tables 4A and 4B), making it invaluable in subject composition use and unique therapeutic use for disease and wound tissue healing and tissue reformation, tissue protein synthesis in conjunction with other viable therapeutic usages such as but not limited to anti-inflammatory effects, a rejection activity, reversal of disease systemic effects and illustrated and exemplified in such as but not limited to growth and puberty impairment in pediatric Crohn's disease reversal of sedimentation rate C-reactive protein, averting the need for liver transplant in congenital biliary atresia and many other embodiments. All illustrating the stem cell activity and stimulation of subject composition in the therapy of disease.

The effects of biochemical essence of human stem cell and the effect of mimicking and analog to human tissue can be seen in cells of the epidermis retaining their stem cell character as long as they are attached to basement membrane components. Chondrocytes in cartilage production remain active as long as they are in contact with the stimulus of collagen and cartilage specific proteoglycans. The prior art has not taught the use of subject composition and its components as a stem cell therapeutic agent analog and mimicking embryonic stem cell tissue as presented in these embodiments to become available as a therapeutic pharmaceutical agent. Nor has it been taught that the additional value of non-covalent bonding into further mimicking and analogue to the most important bonding technique used in human tissue by the body because of no restricted limitation of prompt exchange promulgated by non-covalent bonding therefore the valued multiplicity of efficacious therapeutic uses with minimal if any side effects. At the same time as synergizing these many effects and the effects of co-use with covalent and valently bonded medications from examples such as but not limited to antibiotics in major infections with associated severe inflammatory changes, to insulin in the management of diabetes with associated severe inflammatory changes and great need for tissue healing such as but not limited to progressively severe atherosclerosis and debilitating complicating changes, additionally synergized by the following further HLB modulation that may be optionally included in subject composition (s):

1. The non-covalent further bonding with phospholipids and required HLB modulation can be further illustrated by the advantageous use of hydrophilic surfactants reaching an HLB of 18 to 20 such as but not limited to Tween 60, and sodium lauryl sulfate respectively as therapeutically applied to antibiotics or used in conjunction with antibiotics (these surfactants may be applied locally and/or systemically for a systemic infection and/or systemically for, but not limited to a systemic infection) in the treatment of resistant infections such as but not limited to gram negative *E. coli* with its own outer bacterial protective fatty cell membrane component covering that makes it gram negative and antibiotic resistant and/or similar use with insulin in associated lipid diseased metabolism. Phospholipids such as phosphatidyl choline and HLB of two, PGPR can be added to synergize prior dispersion of the fat and make it more available for further synergistic foregoing action of highly hydrophilic surfactants.

2. These foregoing therapeutic components and progressive steps of subject composition may be similarly applied to other diseases with disturbance in fat metabolism such as, but not limited to, cystic fibrosis synergizing its inadequate lipase activity, and in the rare Gaucher's disease a lipid storage disease of glycolipid cerebroside with its characteristic foam cells may be helped in a similar sequential HLB treatment fashion or perhaps, with hydrophilic surfactant alone. Thereby so emulsifying the fat into very small particles of fat, which more readily fit into the 3D lipase enzymatic molecular clefts in metabolizing the fatty plaques even with excess of fat or deficiency of enzyme or excessive enzyme inhibitor (appropriate enzyme inhibitor modulation and/or additions of appropriate enzymes may be optionally added to subject composition).

3. The same principle as applicable to any enzyme deficiency quantitatively or qualitatively as in the uncommon lysosomal storage diseases in this case lipid storage disease such as, but not limited to, Nieman Pick deficiency of sphingomyelinase and therefore an abnormal accumulation of sphingomyelin in vital organs resulting in disease occurs.

4. Other similar deficiencies in enzymes result in, storage disease is included glycogen storage disease such as Pompe disease, other rarer lipid storage disease sphingolipidoses such as but not limited to Tay Sachs disease, as sulfatidosis such as but not limited to Fabry disease and includes Gaucher disease and Nieman-Pick disease mucopolysaccharidosis such as Hurlers disease, mucolipidosis such as but not limited to pseudo-Hurler disease. All of these storage disease represent and result from an impairment in metabolism a commonality of all plaque like diseases another commonality is poor solubility and poor solubilization but also represented by the prion diseases in animals and humans, Alzheimer's disease, with plaque-like microscopic cerebral tangles, and even more commonly represented by atherosclerosis and its associated poorly metabolizable lipid plaque. Another diverse example of this principle is asbestosis where the asbestos is not only poorly combustible and there for used as fireproofing but also poorly combustible from the metabolic standpoint. Plaque-like diseases may be grouped and looked upon as a poorly soluble bone stuck in the throat of diseased metabolism.

5. All these diseases may be given as a therapeutic opportunity for reversibility to more normal state by the above suggested modulation of HLB with highly hydrophilic surfactants of HLB of 18 to 20 such as but not limited to Tween 80 and sodium lauryl sulfate preceded by lipophilic surfactant for lipid dispersion such as extreme lipophilic HLB surfactant of 2 as in the case of PGPR which may be accompanied by the surfactants found in lecithin such as, but not limited to, phosphatidyl choline. With neurologic involvement phosphatidyl inositol also should be included which has an application affinity and efficacy for the nervous system which should also be utilized as a representative of a lecithin derived polar active surfactant in addition to the foregoing therapeutic efforts, which may be optionally included in the subject composition, to reverse these plaque-like disease states.

The major lipid components of biological cell membranes include but are not limited to glycerophospholipids, sphingolipids, glycosphingolipids, and glycoglycerolipids as the components of the subject composition.

The most common phospholipid applied to vesiculation of cell membrane of subject composition, analogue and mimicking human tissue is phosphatidyl choline but specific therapeutic variations may be necessary as required by disease and disease site such as dipalmatylphosphatidyl choline, a natural surfactant of the lung such as, but not limited to, its application in atelectasis in the infant or adult, and may in this instance occupy as much as 50% or more of the total phosphatidyl choline. In the case of biliary tract disease and gallstones diacyl-phosphatidyl choline. In the case of the erythrocyte disease, the use of dipalmatylphosphatidyl choline, again mimicking and analogue to the phosphatidyl choline of normal erythrocytes. The kidney and heart are made up of both diacyl and alkenylacyl phosphatidyl choline.

Other examples such as, but not limited to the liver, show that more than 20 molecular species of phosphatidyl choline have been identified and, therefore, applicable to subject composition. Adipose tissue, palmitoyl stearoyl oleates and linoleates show variations in subject composition and may be necessary in this therapeutic disease application for subject composition.

Table 5 enclosed to illustrate variations in phospholipid and other polar lipids applicable in subject composition, e.g. the second carbon of phosphatidyl choline is usually unsaturated and the first carbon is saturated fatty acid component, but this may be reversed. The phospholipids are usually of seed oil origin but may also be derived from animal tissue origin e.g. but not limited to fish oil. After the omega-3 anti-inflammatory fish oil source, (anti-prostaglandin one and three) fish oils are extracted, the 60 percent residual lipid now available can be degummed as a source of phospholipid membrane surfactant with yet another pharmaceutical activity omega-3 anti-inflammatory activity can be covalently present at (or may be used non-covalently as in embodiments of subject composition in patent application Ser. No. 09/639,859, hereby incorporated by reference in its entirety). This combined pharmaceutical efficacy may also be accomplished by covalently bonding for example but not limited to esterification of phospholipid cell membrane lysolecithin (produced from fish or seed oil sources) pharmaceutical activity with fish oil or seed oil source anti-inflammatory omega-3 fatty acid activity again analogue to and mimicking human tissue.

Other extracellular matrix components or components that interact with extracellular matrix may be included in the subject composition (again analogue to and mimicking human tissue):

1. Intact basement membrane and its components are considered important in the prevention of the invasion and metastatic invasive spread of diseases such as but not limited to cancer in preventing the spread of cancer to the extracellular matrix and into the bloodstream. Transmembrane cadherins, a calcium dependent family of adhesion molecular glycoproteins whose loss of function has been associated with cancer metastasis and to be considered for inclusion in subject composition in helping with this disease of very poor prognosis.

2. Classic cadherins (E epithelial, N neural, P placental respective cell sites of origin) complex with cytoplasmic proteins known as catenins anchoring them to the attn based cytoskeleton required for adhesive function. Desmocollins and desmogleins differ from the classic family cadherins by the structure of the cytoplasmic domain.

3. The structural glycoproteins such as fibronectin one of the first macro molecules deposited in embryonic stem cell activity in embryonic development and similarly active in the wound healing of many embodiments and looked upon as a recapitulation of embryonic stem cell activity. Because of the fibronectin bonding capacity and specialized binding sites it connects cellular and other components of the extracellular matrix into functional units along with collagen type III is therefore important in tissue healing in wounds and disease. Collagen, fibronectin. along with laminin, are the first to be deposited as extracellular matrix by embryonic stem cell in the fertilized ovum stage and parallel their importance in healing wounds and disease tissue used here in subject composition analogue to and mimicking human tissue (as well as all extracellular matrix components to follow).

4. These adhesive glycoproteins (analogue to and mimicking human tissue) making one extracellular matrix component combined to another and to cells, in this function also include the integrins. Fibronectin molecules binds avidly to collagen, proteoglycans, glycosaminoglycans, fibrinogen, fibrin, cell surface, bacteria and DNA. Fibronectin is ubiquitous in the extracellular matrix found in the delicate filaments, as small aggregates, attached to collagen fibers on cells surfaces, a him and may be trapped in basement membranes such as the glomerular filter. Another extracellular matrix glycoprotein is osteonectin and another homologous glycoprotein SPARC (protein rich L cysteine amino acid) also found in some basement membrane. Osteopontin and osteocalcin are other glycoproteins found in osseous tissue.

5. Analogue to and mimicking human tissue for subject composition and for optional subject composition inclusion: Proteoglycans are found widely distributed on cells surfaces, biologic fluids and in all extracellular matrices. As organizers of the extracellular matrix they are deposited early in wound healing even before collagen so important in the disease and tissue heating function and structure of many embodiments presented here. Some of the most common proteoglycans, such as but not limited to heparin sulfate, chondroitin sulfate and dermatan sulfate, their polysaccharide polymer component glycosaminoglycans (contain an amino sugar) were formerly called mucopolysaccharides and their high-grade gels maintain tissue turgor. They participate in the organization of extracellular matrix by binding to $collagen_s$ elastic fibers and fibronectin. In wounds and disease healing the collagen fibers provided tensile strength, interwoven with elastin limit the elasticity of elastin, which has the ability to recoil after stretching as provided by the elastin glycoproteins rich in lysine and proline like collagen but unlike collagen elastins contains no hydroxylated amino acids.

6. Elastlin's molecular cross-links form an extensive network and random coils (rather than definitive proteins folds oscillating between different states and form the random folds) determine their capacity to stretch and recoil. It is evident that many components of extracellular matrix such as but not limited to, elastin are enmeshed and entwined in extracellular matrix products analogue to and mimicking human tissue included in subject composition such as generic capsules or liquid of shark or beef (such as but not limited to tracheal cartilage) collagen, chondroitin sulfate to be included in subject composition. The elastin (available such as, but not limited to, generic porcine aortic powder) to be included in subject composition in the therapeutic management of cardiovascular disease and vascular disease, including the in vitro growth of heart valves for potential replacement in contrast to porcine valves in vascular diseases such as but not limited to congenital heart disease, atherosclerotic aortic stenosis and aortic lesions such as but not limited to the management of Marfans syndrome, elastin deficiency, subject compositions so enriched with elastin also subject composition may be similarly adapted as in foregoing examples, and made applicable to skeletal diseases such as but not limited to those caused by Marfan syndrome.

7. Other components interacting with extracellular matrix including, but not limited to, actin, talin, vinculin, is paxillin, alpha actin, tensin, kinase.

8. Included in the molecular components of subject composition are the polypeptide growth factors listed in Table 4A and may be enmeshed in the extracellular matrix with its significant downloaded software computer-like information for example but not limited to EGF/TGF alpha with its embryonic stem cell like function (has been added in experimental animal stem cell studies to cause precocious tooth eruption and eyelid opening in animals).

9. Fibroblast growth factor, FGP plays a significant role in wound repair and can associate with heparin sulfate in the extracellular matrix serving as a reservoir for growth factor controlling cell proliferation. Tables 4A and 4B illustrate factors in wounds and disease healing.

In the processing presented in several embodiments of pathogens and minimizing reactive pathogenic effects as in the case of, such as, but not limited to: proteins as allergens in allergic diseases, potential side effects of were foreign proteins in vaccine production, abnormal prion proteins as in Mad Cow or the human equivalent disease modification whether by removal of potentially contaminated bovine liquid products such as milk with ultrafiltration, or 3D spatial protein modification by processing as applied to such potential products, but not limited to, meat that might possibly derive from cow in areas where mad cow disease is epidemically suspected, with supercritical carbon dioxide, liquid nitrogen, urea or guanidine treatment of 3D spatial modification of proteins analogue and mimicking heat denaturation of a protein with the quantitative change and qualitative change in structural and functional capacity in contrast to former pathogenic states are measurable and of utmost importance in the comparative reporting as applied to safer consumer use and consumer exposure. This can be exemplified but not limited to any of the above treatments resulting in a product tolerated by the moderately allergic patient with a 90 to 99 percent reduction of the pathogenicity and pathogenic reactive potential, such as but not limited to, the reduction of allergenicity as required for the prevention of severe allergic reactions in the exquisitely hypersensitive allergic patient where one nanogram or even one picogram or even tenfold 100 fold or one thousand fold less than that, might be approaching very practical limit of tolerance for this extremely allergic patient.

In the United States about 2000 such severe reactions are reported yearly, e.g., anaphylaxis to milk, and are included in the medical categorical description as but not limited to anaphylaxis.

Example 1

Whey diluted 20% with spring water was filtered through a tubular spiral wound membrane ultrafilter (0.01 μm pore size). The permeate (pH 6.6) was immediately batch pasteurized at 145° F. for 30 minutes, followed by refrigeration. Reexamination of the pH and titratable acid revealed no decrease in pH or increase in acid after 7 days of refrigeration.

Example 2

Several six-ounce glasses of the refrigerated permeate of Example 1 were flavored with 12 ml (corresponding to 5%) of one of the following flavor concentrates: banana, hypoallergenic low acid orange, hypoallergenic chocolate flavor, or tropical fruit. In another experiment, 30 ml of non-concentrated pear nectar was added to 70 ml of refrigerated permeate. A taste panel found all these products to be pleasant tasting, very palatable, bland and not salty.

Example 3

The liquid permeate of Example 1 was dried to a moisture content of about 4 wt % by spray-drying, employing a dryer inlet temperature of 400° F. and a dryer outlet temperature of 200° F., with a drying time of 4 hours, at a pressure of 2500 psi, and a 68 gauge spray nozzle bore. Two 50 lb samples of dried permeate were produced in this manner. The dried permeate was then reconstituted to its native liquid form by combining 6.2 weight parts of powder with 93.8 weight parts of water.

Example 4

The powdered permeate of Example 3 was reconstituted in flavored soda by adding 3 weight parts of flavored soda to 7 weight parts of powdered permeate.

Examples 5 to 6

To 100 ml of the reconstituted liquid permeate and permeate-soda of Examples 3 and 4 was added one drop of lactase. The samples were stored for 24 hours in a refrigerator to permit the lactase to act on lactose in the samples, resulting in the production of the monosaccharides glucose and galactose which sweetened the product.

Example 7

Seventy ml of the reconstituted liquid permeate prepared according to Example 3 is diluted with 30 ml water to achieve a potassium level of about 25 mEq/L. To the 100 ml sample is then added the following: 2 mEq NaCl and 1 mEq sodium citrate. This increases the sodium level of the sample to 45 mEq/L from the estimated natural level of 15 mEq/L, and increases the citrate level to 29 mEq/L from the estimated natural level of 19 mEq/L. The addition of the NaCl also increases the chloride level from 18 to 38 mEq/L. Upon addition of flavoring, the product may be used as an electrolyte beverage to replace fluid or electrolytes lost from diarrhea.

Example 7a

To the electrolyte beverage of Example 7 was added 3.5% finely milled and sifted rice flour to augment the taste of the electrolyte solution.

Example 7b 1 gram of essentially fat-free (less than 1 wt % fat) cocoa powder (prepared by supercritical $CO_2$ treatment of cocoa powder) was added to 100 ml of the beverage prepared according to Example 7 to form an electrolyte fluid replacement liquid drink. One drop of lactase enzyme was then added to convert the lactose to component monosaccharides.

Example 8

1 gram of essentially fat-free (less than 1 wt % fat) cocoa powder (prepared by supercritical $CO_2$ treatment of cocoa powder) was added to 100 ml of liquid permeate prepared in accordance with Example 1, diluted 90% with water to achieve a potassium level of 3 mEq/L. One hundred mg of NaCl was then added to achieve a sodium level of 19 mEq/L and a chloride level of 20 mEq/L. Fructose was added in the amount of 4.5 g to bring the carbohydrate level to 5%. The result was a chocolate-flavored electrolyte fluid replacement drink also useful as a sports drink.

Example 8a

One gram of essentially fat-free (less than 1 wt % fat) cocoa powder prepared by supercritical $CO_2$ treatment of cocoa powder was added to the beverage of Example 8, along with 2% finely milled and sifted rice flour to augment the taste of the sports exercise drink.

Example 8b

To 100 ml of the exercise drink of Example 8a was added 1 drop of lactase enzyme preparation, followed by refrigeration for 24 hours to convert the lactose to its component monosaccharides, namely, glucose and galactose. The conversion of lactose augmented the taste of the beverage.

Example 9

A hypoallergenic milk product was prepared as follows. To 250 ml of the liquid permeate prepared according to Example 1 was added 3.5% oat soy powder, 0.5% deproteinized anhydrous oil rendered hypoallergenic in accordance with U.S. Pat. No. 5,112,636, 0.05% vitamin E as an antioxidant and 1.8% finely milled and sifted rice flour.

Example 9a

The procedure of Example 9 was repeated except that the amounts of finely milled and sifted rice flour was increased to 3.5%, and 1% supercritical $CO_2$-defatted chocolate flavor was added.

Example 10

0.62 grams of dried whey permeate was added to 50 ml of diet non-phosphate cream soda and 50 ml of non-phosphate cream soda to achieve a fructose concentration (fructose is the carbohydrate in the soda) to 6.0%. To this was added 100 mg of NaCl to achieve a sodium ion concentration of 19 mEq/L (45 mg %) and a chloride level of 20 mEq/L. The beverage is useful as a sports exercise drink.

Example 10a

One gram of essentially fat-free (less than 1 wt % fat) cocoa powder prepared by supercritical $CO_2$ treatment of cocoa powder was added to the beverage of Example 10, along with 2% finely milled and sifted rice flour to augment the taste of the exercise drink. The beverage is also an instant soda fountain drink.

Example 10b

To 100 ml of the exercise drink of Example 10a was added 1 drop of lactase enzyme preparation, followed by refrigeration for 24 hours to convert the lactose to its component monosaccharides, namely, glucose and galactose. The conversion of lactose augmented the taste of the beverage.

Example 11

Example 10 was repeated, deleting the 50 ml of diet soda and increasing the amount of non-diet soda to 100 ml, to achieve a pleasantly flavored hypoallergenic sports exercise drink beverage having a carbohydrate content of 11%.

Example 11a

To 100 ml of the beverage of Example 11 was added 1 gram of essentially fat-free (less than 1 wt % fat) cocoa powder prepared by supercritical $CO_2$ treatment of cocoa powder.

Also added was 2% of finely milled and sifted rice flour to augment the taste of the beverage.

Example 12

An elemental sports exercise drink is prepared as follows. To the composition of Example 10b is added 0.5% of an amino acid mixture containing less than 0.25% protein, preferably less than 0.025% protein.

Example 13

An electrolyte replacement beverage is prepared by adding to the composition of Example 7 0.5% of an amino acid mixture containing less than 0.25% protein, preferably less than 0.025% protein.

APPENDIX 1

NEOCATE Ingredients

|  | Per 100 kcal | Per 100 G | Per Quart (32 fl oz) |
|---|---|---|---|
| Calories | 100 | 420 | 640 |
| Amino Acids, g | 3.7 | 15.5 | 23.6 |
| (Protein Equivalent, g) | 3.1 | 13 | 19.8 |
| Fat, g | 4.5 | 19.1 | 29 |
| Carbohydrate, g | 11.7 | 49.3 | 74.9 |
| Water, g | 131 | 550 | 840 |
| Linoleic Acid, mg | 677 | 2850 | 4332 |
| VITAMINS | | | |
| Vitamin A, IU | 409 | 1721 | 2616 |
| Vitamin $D_3$, IU | 87 | 366 | 556 |
| Vitamin E, IU | 1.14 | 4.8 | 7.3 |
| Vitamin K, mcg | 8.79 | 37 | 56 |
| Thiamin, mcg | 92.6 | 390 | 593 |
| Riboflavin, mcg | 137.8 | 580 | 882 |
| Vitamin $B_6$, mcg | 123.5 | 520 | 790 |
| Vitamin $B_{12}$, mcg | 0.17 | 0.7 | 1.1 |
| Niacin, mg | 1.54 | 6.5 | 9.88 |
| Folic Acid, mcg | 10.2 | 43 | 65 |
| Pantothenic Acid, mg | 0.62 | 2.61 | 3.97 |
| Biotin, mcg | 3.1 | 13 | 20 |
| Vitamin C, mg | 9.26 | 39 | 59 |
| Choline, mg | 13.1 | 55 | 84 |
| Inositol, mg | 23.3 | 98 | 149 |
| MINERALS | | | |
| Calcium, mg | 124 | 522 | 793 |
| Phosphorous, mg | 93.1 | 392 | 596 |
| Magnesium, mg | 12.4 | 52 | 79 |
| Iron, mg | 1.85 | 7.8 | 11.9 |
| Zinc, mg | 1.66 | 7 | 10.6 |
| Manganese, mcg | 90 | 380 | 578 |
| Copper, mcg | 124 | 520 | 790 |
| Iodine, mcg | 15.4 | 65 | 99 |
| Molybdenum, mcg | 4.75 | 20 | 30 |
| Chromium, mcg | 3.56 | 15 | 23 |
| Selenium, mcg | 3.73 | 15.7 | 23.9 |
| Sodium, mg | 37.3 | 157 | 239 |
| Potassium, mg | 155.1 | 653 | 993 |
| Chloride, mg | 77.2 | 325 | 494 |

Ingredients:
Corn Syrup Solids (55.9%), Hybrid Safflower Oil (11.2%), Refined Vegetable Oil (Coconut 6.1%, Soy 3.1%), L-Lysine L-Glutamate (2.8%), Calcium Phosphate Dibasic (2.4%), and less than 2% of each of the following: L-Leucine, Tripotassium Citrate, L-Proline, L-Arginine, L-Valine, L-Aspartic Acid, L-Isoleucine, Glycine, L-Threonine, L-Tyrosine, L-Phenylalanine, L-Serine, L-Histidine, L-Alanine, Mono and Diglycerides, Sodium Chloride, L-Cystine, L-Tryptophan, Magnesium Acetate, L-Methionine, Potassium Chloride, Diacetyl Tartaric Acid Esters of Monoglycerides, L-Glutamine, Choline Hydroxide, L-Glutamic Acid, M-Inositol, Soy Lecithin, Tricalcium Phosphate, Ascorbic Acid, Ferrous Sulfate, Zinc Sulfate, Taurine, L-Carnitine, Niacinamide, DL-alpha Tocopheryl Acetate, Calcium Pantothenate, Cupric Sulfate, Manganese Sulfate, Pyridoxine Hydrochloride, Vitamin A Acetate, Riboflavin, Thiamine Chloride Hydrochloride, Potassium Iodide, Chromium Sulfate, Phylloquinone, Sodium Molybdate, Folic Acid, Sodium Hydrogen Selenite, Biotin, Vitamin D3 and Cyanocobalamin.

APPENDIX 2

Vivonex Ingredients

Maltodextrin, Modified Starch, Medium Chain Triglycerides, Soybean Oil, Calcium Glycerophosphate, Magnesium Gluconate, L-Glutamine, L-Lysine Acetate, L-leucine, L-Arginine Acetate, Potassium Chloride, L-valine, Citric Acid, L-isoleucine, L-Aspartic Acid, L-Alanine, L-Phenylalanine, L-Serine, L-Proline, L-Threonine, L-tyrosine, L-Glutamic Acid, Glycine, L-Histidine Monohydrochloride Monohydrate, L-methionine, Potassium Citrate, L-cystine, Choline Bitartrate, Sodium Citrate, Ascorbic Acid, Polyglycerol Esters of Fatty Acids, L-Tryptophan, Sodium Phosphate Dibasic, Potassium Sorbate, Taurine, M-Inositol, Alpha Tocopheryl Acetate, Zinc Sulfate, Ferrous Sulfate, Niacinamide, L-carnitine, Alpha Tocopherol, Copper Gluconate, Pantothenate, Manganese Sulfate, Pyridoxine Hydrochloride, Riboflavin, Thiamine Hydrochloride, Bha/bht to Preserve Freshness, Vitamin A Palmitate, Beta Carotene, Folic Acid, Chromic Acetate, Sodium Molybdate, Potassium Iodide, Biotin, Sodium Selenite, Phytonadione Vitamin K1, Cholecalciferol Vitamin D3, Cyanocobalamin Vitamin B12.

TABLE 4A

GROWTH FACTORS WORKING IN CONCERT WITH SUBJECT COMPOSITION

Growth Factors in Wound and Disease Healing

| | |
|---|---|
| Monocyta chemoraxis | PDGF, FGF TGF-B |
| Fibroblast migration | PDGF, EGF, FGF, TGF-B, TNF |
| Fibroblast proliferation | PDGF, EGF, FGF, TNF |
| Angiogenesis | VEGF, Ang, FGF |
| Collagen synthesis | TGF-B, PDGF, TNF |
| Collagenase secretion | PDGF, FGF, EGF, TNF, TGF-B inhibits Growth Factors |

Epidermal growth factor (EGF) family EGF
Transforming growth factor-a (TGFa)
Platelet-derived growth factor (PDGF)
Fibroblast grown factor (FGF)
    Basic
    Acidic
Transforming grown factor B-(TGF) family
TGF-B
Bone morphogenic proteins
Activins, others
Vascular endothelial growth factors (VEGF)
Angiopoietins (Ang)
Insulin-like growth factors (IGF)
Hepatocyte growth factor (HGF)
Connective tissue growth factor (CTGF)
Myloid colony-stimulating factors (MCSF)
Granulocyte-macrophage CSF (GM-CSF)
Granulocyte CSF (G-CSF)
Macrophage CSF (M-CSF)
Erythropoietin
Cytokines
Interleukins
Tumor necrosis factor (TNF)
Interferons a. b

TABLE 4A-continued

GROWTH FACTORS WORKING IN CONCERT WITH SUBJECT COMPOSITION

Nerve growth factor (NGF)

Optional Therapeutic Subject Composition Components

TABLE 4B

| | Vascular Endothelial Growth Factor |
|---|---|
| Proteins | Family members: VEGF, VEGF-B, VEGF-C, PIGF Dimeric glycoprotein with multiple isoforms Targeted mutations in VEGF resulted in defective Vasculogenesis and ingiogenesis |
| Production | Expressed at low levels in a variety of adult tissue And at higher levels in a few sites, such as Podocytes in the glomerulus and cardiac myocytes |
| Inducing agents | Hypoxia TGF-3 PDGF TGF-a |
| Receptors | VEGF-R1 VEGF-R2 Restricted to endothelial cells Targeted mutations in the receptors resulted in lack of vasculogenesis |
| Functions | Promotes angiogenesis Increases vascular permeability Stimulates endothelial cell migration Stimulated endothelial cell proliferation VEGF-C selectivity induces hyperplasia of lymphatic vasculature Up-regulates endothelial expression of plasminogen activator, plasminogen activator inhibitor-1, tissue factor, and interstitial collagenase |

Optional Therapeutic Subject Composition Components

Scientific rationale: Completing the continued agenda of the efficacy of Q101KC therapeutic composition and providing evidence in the form of pre-clinical studies and clinical studies based on accepted scientific principles that Q101KC, therapeutic subject composition, when given in vivo can mimic the therapeutic effect of a certain medicament, which is analogue to and mimics this medicament, analogue to human tissue and newest form of therapeutic medication, therapeutic stem cell.

Also, further exemplifying that the use Q101KC to synthesize a medicament in vivo would constitute a drug which is eligible for Orphan Drug designation.

L amino acid and amino acid analogue and mimicking of medicaments-Highlights of rationale regarding the use of Q101KC in subject composition with free L amino acids and amino acids analogue and mimicking a medicament or medicaments in structure and function and in reactive high energy ionizing side chain groupings. Subject composition Q101 KC also provides analogue mimicking of medicament included in in-vivo synthesis of a medicament and its function and structure in the metabolite internal milieu.

Permeability Test Tagged Neutrophil for Crohn's Disease

Propionic Acid Derivatives—Structural Formulas of Anti-inflammatory Propionic Acid Derivatives Glycine pharmacologic component of Q101KC action working synergistically with optically active free L amino acid counts for the clinical efficacy of Q101KC in vitro study and reversing inflammatory variability defect of the pediatric Crohn's disease.

A Synthetic Amino Acid, Part of the mainstay Therapeutics of PCD.

Analogues Highlights

Q101KC contains 4 carbon L amino acids analogue to anti-inflammatory butyric acid Pharmacodynamics and pharmacokinetics of Q101KC free L amino acid and amino acid subject composition analogue to and mimicking NSAID but free of NSAID side effects, and simultaneously analogue to and mimicking human tissue and in vivo tissue healing tissue protein healing and efficacy of Free L amino acids of Subject Composition Pharmacodynamics and Pharmacokinetics of Q101KC free L amino acid and amino acid subject composition analogue to and mimicking NSAID but free of NSAID side effects, and simultaneously analogue to human tissue and in vivo tissue healing tissue protein healing and efficacy. Analogue to and mimicking NSAID. Indomethacin.

Pharmacognosy of therapeutic Q101KC subject composition L amino acids and amino acids analogue to and mimicking medicaments, human tissue, and human tissue molar ratio in the treatment of pediatric Crohn's disease.

Pharmacodynamics and pharmacokinetics of Q101KC free L amino acids and amino acids subject composition analogue to mimicking NSAID but free of NSAID side effects, and simultaneously analogue to human tissue and in vivo tissue healing tissue protein healing and efficacy. Q101KC L amino acids and amino acids and its reactive ionizing side chains is analogue to NSAID and its reactive side chains.

Therapeutic Importance Of High Energy Reactive Side Grouping As In Q101KC.

Q101KC L amino acids and amino acid analogue to and mimicking: medicaments, analogue ionizing side chains of medicaments as well as analogue to and mimicking human tissue with human tissue healing effects on PCD and CBA.

Q101KC Pharmacologic Function added to the many Pharmacologic and Physiologic Functions of Amino Acids and L Amino Acids Q101KC L amino acids and amino acids analogue to and mimicking medicaments and human tissue effects on PCD and CBA.

Pharmacologic Rational for Clinical Efficacy of Q101KC in PCD and CBA and their Subsets Q101KC L amino acids and amino acid analogue to and mimicking medicaments, analogue ionizing side chains of medicaments as well as analogue to and mimicking human tissue with human tissue healing effects on PCD and CBA.

A Significant Therapeutic Accomplishment

Tabulation of Effects

Q101KC L amino acids and amino acid analogue to and mimicking medicaments and human tissue effects on PCD and CBA.

Crohn's Disease in Childhood

Tabulated documentation. Establishment of normal linear growth using Q101KC in growth and pubertal retardation.

Efficacy of Q101KC in the Treatment of PCD, Subsets 1 and 2

Subset 2: FISTULAE

PCD Graphic Analysis of Pharmacologic Analogue Advantages of Q101KC Anti-inflammatory Tissue Healing Pharmacodynamics in Pediatric Crohn's Disease (Both Analogue to and Mimicking Medicaments and Human Tissue and Their Healing Qualities)

CBA Graphic Analysis of Pharmacologic Analogue Advantages of Q101KC Anti-inflammatory Tissue Healing Pharmacodynamics in Congenital Biliary Atresia (Both Analogue to and Mimicking Medicaments and Human Tissue and Their Healing Qualities)

Photographic records—including case report and clinical progress tracked by physical examinations of patient as evidenced by sequential photographic records Proposed Indications Incidence of Allergic Symptoms in Pediatric Liver Transplant Recipients Treated with Tacrolimus Based Immunosuppression L amino acid and amino acid analogue and mimicking of medicaments-Highlights of rationale regarding the use of Q101KC in subject composition with free L amino acids and amino acids analogue and mimicking a medicament or medicaments in structure and function and in reactive high energy ionizing side chain groupings such as anti-inflammatory medicament such as NSAID and the synthetic amino acid 5 ASA in addition to being analogue and mimicking plasma and tissue L amino acids and amino acids and their tissue molar ratio with tissue healing capacity and efficacy and tissue protein synthesis and resynthesis in such diseased damaged tissue repair as applied to disease management and disease reversal of severe inflammatory disease effects of PCD and CBA and their subsets.

Analogue mimicking of synergism of Q101KC L amino acids and amino acids effects also include the synergism of these aromatic and aliphatic amino acids and the aromatic amine medicaments such as but not limited to the triple sulfonamides.

Subject composition Q101 KC also provides analogue mimicking of medicament included in in-vivo synthesis of a medicament and its function and structure in the metabolite internal milieu.

Analogue Highlights of rationale regarding the use of subject composition with free L amino acid analogue in structure and function and their reactive high energy ionizing side chain groupings, anti-inflammation NSAID, in addition to being analogue to plasma and tissue molar ratio free L amino acid.

Direct Anti-Inflammatory Effect of Elemental Diet on Crohn's Tissue in Vitro

Shand A., Meister D., Aldhous M., Anderson N., and Gosh S., Gut 2000 46 Suppl II: A43

In vitro studies of 6 biopsies of Crohn's diseased tissue, 5 normal controls, both in culture medium.

Key Contributory Comments: "This is the first demonstration of a direct anti-inflammatory effect of an elemental diet in Crohn's disease." With a "reduced production of pro-inflammatory cytokines IL-one beta by more than 80 percent in 24 hours" and "a relative increase in a IL-1 beta inflammatory receptor antagonist compared with inflammatory cytokine IL-1 beta," "casein did not result in any reduction of inflammatory cytokines" "Replacing the "free L amino acids with whole protein casein, whey, in organ culture did not abolish the anti-inflammatory properties."

Therefore, anti-inflammatory activity is dependent upon the presence of free L amino acids. In vitro, when the same amino acids are bound in the protein polymer form anti-inflammatory activity is not present. This demonstrates that this is not a nutritive anti-pathogenic pharmacokinetic function. (Free L amino acids are usually not available in foods.)

Direct Anti-Inflammatory Effect of Elemental Diet on Crohn's Tissue In Vitro

Shand A., Meister D., Aldhous M., Anderson N., and Gosh S., Gut 2000 46 Suppl II: A43

Although an elemental diet is an effective treatment for active Crohn's disease its mechanism of action is not fully understood. A number of potential mechanisms have been proposed including alteration of bacterial flora, low residue, low antigenicity, low fat content and supplementation with essential pharmaconutrients. In pediatric patients a supplemental rather than an exclusive elemental diet has proved effective in maintaining remission suggesting that the efficacy of an elemental formula is not based solely on an exclusion diet. In order to further understand the mechanism of action of an elemental diet, the direct anti-inflammatory activity of an elemental formula was studied in vitro.

Multiple colonic biopsies were taken from 5 patients with a normal colon and 6 Crohn's disease patients and cultured for 24 hours. Cell viability was assessed at 24 hours by BrdU uptake of dividing cells. The supernatant was collected and stored at $-70°$ C. for cytokine assays. E028 (SHS International Ltd, Liverpool, UK) was added at a concentration of 1:20 and viability of the organ culture was determined at 24 hours in a number of pilot studies. E028-casein in a 1:20 concentration was added to the organ culture media of a subset of Crohn's patients (n=3). Pilot studies established that E028 did not interfere with cytokine ELISAs. IL-19 and IL-1 receptor antagonist (IL-1RA) were assayed in the supernatant by ELISA.

In the normal colonic culture, the mean concentration of IL-1 (3 in the supernatant was 407 (SD 306) pg/g tissue and addition of E028 reduced the IL-1B concentration to 208 pg/g (SD 201). In the Crohn's disease colonic culture, the mean concentration of IL-1B in the supernatant was 1512 (SD 1741) pg/g tissue, but addition of E028 reduced the IL-19 concentration to 263 (SD 211) pg/g tissue. In Crohn's disease samples the mean reduction in IL-113 following addition of E028 was 1248 pg/g compared with a mean reduction of 200 pg/g in normal samples (p=0.0006). Audit n of-5-0-28 resulted in a reduction in the mean ratio of IL-1/IL-1RA from 0.13 (SD 0.23) to 0.01 (SD 0.002) in Crohn's disease supernatant. E028-casein did not result in any reduction in IL-19 concentration in the supernatant compared with E028 alone.

Results showed E028 reduced production of the pro-inflammatory cytokine IL-1B in Crohn's disease colonic tissue by more than 80% in 24 hours. This reduction was significantly greater than that observed in normal colonic tissue. Addition of E028 also resulted in a relative increase in IL-1RA compared with IL-1B. As far as the authors are aware this is the first demonstration of a direct anti-inflammatory effect of an elemental diet in Crohn's disease.

Permeability test, tagged neutrophil for Crohn's disease:

Abnormal neutrophil, radioactively tagged, radiograph permeability test of PCD (radiograph enclosed)

(A) Crohn's disease. Low power micrograph showing a deep fissure extending into the muscle wall (center); a second, shallow ulcer (upper right); and relative preservation of the intervening mucosa. Abundant inflammatory aggregates are present, evident as dense patches of cells at the interface between mucosa and submucosa.

(B) Crohn's disease of the colon noncaseating granulomas are present in the lamina propria of a mildly inflamed region of colonic mucosa.

"Mucosal Inflammation: The earliest histologic lesion in Crohn's disease appears to be focal neurophilic infiltration into the epithelial layer, particularly overlying mucosal lymphoid aggregates. As in the disease becomes more established neutrophils infiltrate isolated crypts: when a sufficient number of neutrophils have traversed the epithelium of a crypt (both in this more large intestine), a crypt abscess formed usually the ultimate destruction of the crypt" (Robbins).

The radioactively tagged autologous neutrophil 111 Indium from a Crohn's disease patient systemically administered can be tracked radiographically, pathologically, and patho-physiologically by the abnormal permeability tests that can be reversed in two to four weeks with subject composition as reported by Teahan and Bjarnason et al. and invented by Bjarnason (personal communication). (Teahan and Bjarnason).

(A) Pretreatment abdominal scrintigraphy of a patient with active Crohn's disease showing intense activity in the right iliac fossa representing ileocecal inflammation.

(B) The same patient after 4 weeks of elemental diet showing normal uptake into liver spleen, vertebra and pelvic bones with no significant activity in the right iliac fossa. Normalized ilium 4 weeks after therapeutic subject composition.

"The current study shows for the first time that treatment with elemental diet alone reduces the acute inflammation in patients with Crohn's disease showing that the treatment is not just symptomatic."

"Using a Cr-labeled ethylenediaminetet-raacetatic acid (EDTA) permeability test and Indium labeled leukocytes, we show objectively that treatment with elemental diet reduces intestinal permeability and inflammation in patient with Crohn's disease."

Analogue Propionic Acid (3 carbon base) Propionic Acid Derivatives

These drugs represent a group of effective, useful aspirin-like agents. They offer significant advantages over aspirin indomethacin and the pyrazolon derivatives for many patients since they are normally better tolerated. Nevertheless, propionic acid derivatives share all of the detrimental features of the entire class of drugs. Furthermore, their rapid proliferation in number and heavy promotion of these drugs make it difficult for the physician to choose rationally between a member of the group and between propionic acid derivatives and the more established agents.

Analogue highlights of rationale regarding the use of Therapeutic Subject Composition in Propionic acid free L amino acid derivative of Therapeutic Subject Composition. These free amino acids of Therapeutic Subject Composition are analogue to anti-inflammatory NSAID regarding their use in PCD and CBA.

This therapeutic subject composition functions by adding free L amino acid therapeutic dosage to amino acid produced by the neutrophil, the focal cell of inflammation, thereby reversing, (by the law of mass action), neutrophil enzymatic digestive damage. Simultaneously, Therapeutic Subject Composition contributes to protein synthesis repair of damaged tissue, and is a major contributor to the healing continuum in the therapy of PCD and CBA. This aspect is not present in available anti-inflammatory medications.

Analogue—L. Amino Acid Propionic Acid Derivatives with Anti-inflammatory Function of Q101KC Subject Composition Analogue to NSAID—Propionic Acid Derivatives Such as Ibuprofen and Naproxen These drugs represent a group of effective, useful aspirin-like agents. They may offer significant advantages over aspirin, indomethacin, and the pyrazolon derivatives for many patients, since they are usually better tolerated. Nevertheless, propionic acid derivatives share all of the detrimental features of the entire class of drugs. Furthermore, their rapid proliferation in number and heavy promotion of these drugs make it difficult for the physician to choose rationally between members of the group and between propionic acid derivatives and the more established agents. The similarities between drugs in this class and certain others discussed above are far more striking than are the differences.

Ibuprofen, naproxen, flurbiprofen, fenoprofen, and ketoprofen are described individually below. These drugs are currently available in the United States, but several additional agents in this class are in use or under study in other countries. These include fenbufen, pirprofen, oxaprozin, indoprofen, and tiaprofenic acid. Ibuprofen was the first member of this class to come into general use, so experience with this drug is greater. It is available for sale without a prescription in the United States. The most distinctive feature among others may probably be claimed by naproxen; its longer half-life makes twice-daily administration feasible.

Pharmacological Properties. The pharmacodynamic properties of the propionic acid derivatives do not differ significantly. While the compounds do vary in potency, this is not of obvious clinical significance. All are effective anti-inflammatory agents in various experimental models of inflammation in animals; all have useful anti-inflammatory, analgesic, and antipyretic activity in man. All of these compounds can cause gastrointestinal erosions (gastric, duodenal, and intestinal) in experimented animals.

Free fatty acids, acyl carnitine, and lysophospholipids, catabolic products that are known to accumulate in ischemic cells as a result of phospholipid degradation. They have a detergent effect on membranes. They also either insert into the lipid bilayer of the membrane or exchange with membrane phospholipids, potentially causing changes in permeability and electrophysiologic alterations.

Loss of Intracellular Amino Acids.

Addition of certain amino acids, principally glycine, protects hypoxic cells from irreversible membrane damage in vitro, suggesting that loss of such amino acids—which occurs in hypoxia—predisposes to membrane structural injury. Glycine also enables ATP-depleted cells to resist the lethal effects of high calcium and thus remain viable.

Whatever the mechanism of membrane injury, the resultant loss of membrane integrity causes further influx of calcium from the extracellular space. When, in addition, the ischemic tissue is reperfused to some extent, as may occur in vivo, the scene is set for massive influx of calcium. Calcium is taken up avidly by mitochondria after reoxygenation and permanently poisons them, inhibits cellular enzymes, denatures proteins, and causes the cytologic alterations characteristic of coagulative necrosis.

In summary, hypoxia affects oxidative phosphorylation and hence the synthesis of vital ATP supplies. Membrane damage is critical to the development of lethal cell injury, and calcium is an important mediator of the biochemical and morphologic alterations leading to cell death.

Pediatric Crohn's disease suppression is significantly worsened by corticosteroids (a mainstay of PCD treatment) which complicates the management of PCD, not seen and a very significant advantage with use of Therapeutic Subject Composition (Q101KC) in minimizing (as little as one tablet of corticosteroid every other day) or averting the need for corticosteroids.

*Using Therapeutic Subject Composition Q101KC, a multi-center study reported is as effective in producing remission of Crohn's disease (CD) as is corticosteroid treatment.

Azulfidine (sulfasalizine) whose active component being 5 amino salicylic acid, a synthetic amino acid represents another steroid sparing medication (and a PCD mainstay therapy) with activity similar in efficacy and effect as Q101KC.

A Synthetic Amino Acid, Part of the Mainstay Therapeutics of PCD.

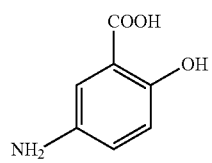

The chemical groupings associated with anti-inflammatory activity of the bowel, in PCD $NH_2COOH$, Phenol are all remarkably similar to tyrosine in structure and function.

*Mesalamine (5-aminosalicylic acid) is a salicylate that is used for its local effects in the treatment of inflammatory bowel disease" (Schroeder et al. 1987).

Sulfasalazine (salicylazosulfapyridine) AZULFIDINE) contains mesalamine (5-aminosalicylic acid) linked covalently to sulfapyridine); it is poorly absorbed after oral administration, but is cleaved to its active components by bacteria in the colon. The drug is of benefit in the treatment of inflammatory bowel disease, principally because of the local actions of mesalamine. Goodman and Gilman's, the Pharmacological Basis of Therapeutics 8th Edition, Pergamon Press.

Asacol, the active ingredient of Azulfadine:

The mechanism of action of mesalamine (and sulfasalazine) is unknown, but appears to be topical rather than systematic. Mucosal production of arachidonic acid (AA) metabolites, both through the cyclooxygenase pathways, i.e., prostanoids, and through the lipoxygenase pathways, i.e., leukotrienes (l-Ts) and hydroxyeicosatetraenoic acids (HETEs), are increased in patients with chronic inflammatory bowel disease, and it is possible that mesalamine diminishes inflammation by blocking cyclooxygenase and inhibiting prostaglandin (PG), production in the colon. Physicians' Desk Reference (PDR) 55th Edition, 2001, 2669.

The components e.g. tyrosine of Q101KC mimic and are analogue in structure and anti-inflammatory function to 5 ASA or sulfasalazine with the added advantage that Q101KC components, such as tyrosine, have anti-inflammatory as well as, healing actions. The components of Q101KC may also be used synergistically to enhance the pharmacologic effects of all the mainstay therapeutic agents of PCD and CBA.

Aromatic Amino Acids

Tyrosine—α-Amino-β-Parahydroxyphenylproprionic Acid

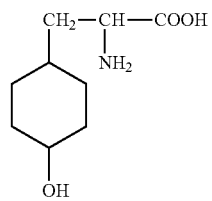 [SMILES: NC(CC1CCC(O)CC1)C(=O)O]

The pharmacokinetics and pharmacodynamics of small molecular (molecular size less than 200) anti-inflammatory biochemicals:

Structural Formulas of the Salicylates

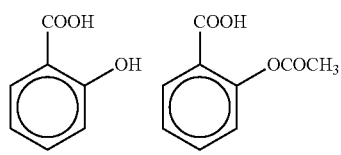

Salicyclic Acid          Aspirin

Aspirin, acetyl salicylic acid, molecular weight 180.16 acetylsalicylic acid whose anti-inflammatory activity (however unable to facilitate) is dependent upon acetyl side chain ionizing grouping is "responsible for the inactivation of cyclooxygenase via acetylation". This anti-inflammatory activity is lost it the acetyl ionizing grouping is removed resulting in salicylic acid. However aspirin is unable to facilitate the continuum of anti-inflammatory healing resolution cycle. In fact aspirin's anti-inflammatory therapeutic action stops short at protein catabolism interruption of collagen healing thread of healing resolution and the normal healing cycle. (The anti-inflammatory corticosteroids a mainstay therapy of PCD share this NSAID side effect but in addition stimulate the production of collagenase which even further notoriously and adversely interferes with healing which can be blocked by retinoic acid, vitamin A in subject composition Q101KC). Q101KC mimics and is analogue to corticosteroids while preventing corticosteroid's pediatric serious side effects of growth suppression, synergistically useful to minimize corticosteroid dosage and minimize side effects.

Aliphatic, Monoamino, Monocarboxylic Acids

Glycine or Glycocoll—Aminoacetic Acid

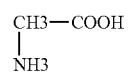

Glycine normally present in subject composition analogue to its presence in plasma and tissue of body is another small molecule anti-inflammatory drug so dependent on its acetyl side chain ionizing grouping. Glycine alpha amino acetic acid molecular weight 75.07 anti-inflammatory therapeutic agent particularly noted for healing 100 angstrom porous cell membrane inflammatory disease permeability defect seen with pediatric Crohn's disease or with pathologic inflammatory changes of congenital biliary atresia. Thereby preventing cell death through irreversible loss of ATP pharmacologically in concert synergistically with healing component phosphatidyl choline essence of cell membrane and the healing collagen thread of healing resolution of subject composition thereby co-synergizing and intensifying this healing resolution action. This anti-inflammatory activity is furthered by synergistic activity of subject compositions e.g. but not limited to tyrosine's phenolic hydroxyl ionizing side chain ionizing as well as anti-inflammatory activity of tyrosine as a propionic acid derivative.

Tyrosine—α-Amino-β-Parahydroxyphenylproprionic Acid

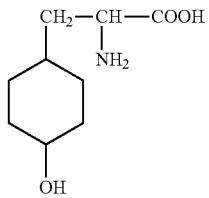 [SMILES: NC(CC1CCC(O)CC1)C(=O)O]

Q101KC thereby mimics and is analogue in function to corticosteroid and mimics and is analogue in structure and function to NSAID and may be used per se or to further synergize therapeutic agents in the treatment of PCD or CBA by all its free alpha amino acid components per rationale (presented here in 1 through 6). The components of Q101KC exhibited here have shown several pronged anti-inflammatory pharmacodynamic and pharmacokinetic biochemical activities.

Analogue highlights of rationale regarding the use of Q101KC in subject composition with free L-amino acid analogue. In structure and function and their reactive high energy ionizing side chain groupings; anti-inflammation NSAID, in addition to being analogue to plasma and tissue molar ratio free L amino acid.

Q101KC contains 4 carbon L amino acids analogue to anti-inflammatory butyric acid, Derivatives.

Anti-inflammatory effects and activity of butyric acid 4C free L amino acid of Q101KC of subject composition compounds, namely:

Valine=alpha Amino beta methyl butyric acid

Threonine=alpha amino gamma methyl thiol butyric acid

Methionine=alpha amino beta hydroxae n.butyric acid

Quotes:

Venkatraman A, Ramakrishna B S, et al. Increased permeability in dextran sulphate colitis in rats: Time course of development and effect of butyrate. Stand J Gastroenterol 2000:35(10): 1053-59.

"CONCLUSIONS: Increased mucosal permeability is a very early change in colitis induced by DSS, is accompanied by decreased cell survival and precedes detectable changes in histology. Reversal of increased mucosal permeability by butyrate may explain its utility in the therapy of inflammatory disease of the colon."

Segain J P. Raingeard de la Bletiere D. et al. Butyrate Inhibits Inflammatory responses through NfkappaB Inhibition: implications for Crohn's disease. Gut 2000: 47(3): 397-403.

"CONCLUSIONS: Butyrate decreases pro-inflammatory cytokine expression via inhibition of NfkappaB activation and IkeppaBalpha degradation. These anti-inflammatory properties provide a rationale for assessing butyrate In the treatment of CD."

Butzner J D, Parmar R, Bell C J, Dalai V. Butyrate enema Therapy stimulates mucosal repair in experimental colitis in the rat. Gut 1996: 38(4): 588-73.

"CONCLUSION: Butyrate enema therapy stimulated colonic repair, as evidenced by clinical recovery, decreased inflammation, and restoration of SCFA stimulated electrolyte absorption."

α-amino-β-hydroxy-n-butyric acid

Threonine- 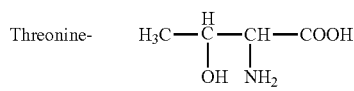

Valine-α-amino-β-methylbutyric acid

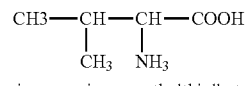

Methionine-α-amino-γ-methylthiolbutyric acid

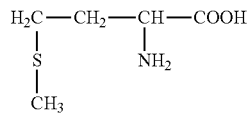

Pharmacodynamic Free L amino acids of Therapeutic Subject Composition

The free L amino acids of Therapeutic Subject Composition present a multiplicity of in-vivo and in-vitro functions including their very significant specific analogue anti-inflammatory structure and function and their high energy reactive side chains and ionizing side chain groups of 25-50 joules of energy per mole.

1. The free L amino acids analogue to synthetic anti-inflammatory medications:

(a) Including analogue of structure and function of synthetic 5 ASA active grouping of sulfasalizine a mainstay treatment of PCD. The phenyl-hydroxyl grouping of tyrosine and the acetyl grouping of glycine offer the analogue grouping representation of 5 ASA.

(b) The C3 propionic acid free L amino acids are analogue to the propionic acid derivative propionic NSAID such as Ibuprofen and Naproxen. The C4 butyric acid free L amino acids are analogue to the synthetic anti-inflammatory butyric acid derivatives. The C6 caproic acid free L amino acids are analogue to the synthetic anti-inflammatory caproic acid derivatives.

2. The synergistic activity of this Therapeutic Subject Composition free L amino acids have anti-inflammatory analogue synergy similar to the synergy triple sulfonamides.

3. Free L amino acid anti-inflammatory activity is not present in the polymer protein. This marked difference may be explained by the free L amino acids reactive and available groupings such as the high energy ionizing alpha amino carboxylic acid groupings being unattached and available, in marked contrast to the polymer protein. The small molecule free L amino acids with a molecular weight range, 100 to 200 will have approximately 1000 times more mole per gram of reactive high energy side chains amid than its corresponding polymer with a molecular weight of 100,000 to 200,000. These Therapeutic Subject Composition reactive and available side chain groupings of free amino acid ionizing alpha carboxyl and ionizing alpha amino side chain grouping with 60 Joule mole per grouping comparatively contain 1000 times more moles of intrinsic reactive energy totaling 60,000 Joule mole in in sharp contrast to one polymerized amino acid mole of protein of 100,00 to 200,000 molecular weight with only 60 Joule mole comparative Joule mole of intrinsic reactive energy per protein lymer mole equivalent molecular weight. (Protein Chemistry, John Kinsella PhD et al). Free L amino acids Therapeutic Subject Composition have other high energy reactive side chain reactive ionizing groupings such as 50 Joule mole side chain energy of guanidinium of arginine, or 50 Joule mole epsilon amino ionizing grouping of lysine, 30 Joule imidazole high energy side chain of histidine, 6 Joule mole energy reactive amino acid ionizing side chain beta carboxyl ionizing side chain of asparagine, and 6 Joule mole gamma carboxyl ionizing side chain of glutamine that are all much more available than as polymerized amino acids particularly as in tertiary or secondary proteins with reactive groupings internalized by hydrophobic forces.

The significant difference of the free L amino acids monomer from its polymer as in food is as striking as H20 is from its component atoms hydrogen and oxygen.

The free L amino acids with their free and unattached reactive high energy ionizing side chains of subject composition Q101KC should not be heated to maintain and reserve the in vivo anti-inflammatory continuum and overlay pharmacologic activities, whereas the polymer amino acids as in foods may be heated as in cooking the free L amino acids with their free and unattached reactive high energy ionizing side chains of subject composition Q101KC should not be compressed or compacted to maintain and reserve the in vivo anti-inflammatory healing continuum and overlay pharmacologic activities hydrogen bonding, van der Waals forces, electrostatic forces and biochemical and pharmacodynamic activity involved in bonding and tissue interaction.

4. The significant documented i58i healing action of free L amino acid of Q101KC actions so important in addressing and completing the anti-inflammatory overlay and continuum of the healing cycle of medications not offered in all of the current anti-inflammatory medications, (in fact, the current anti-inflammatory medications NSAID, not only do not aid in healing but in fact interfere with protein synthesis of healing, (for example but not limited to ASA negative nitrogen balances, inhibition of protein synthesis and protein catabolism, and aminoaciduria, similarly with indomethacin depressing the biosynthesis of protein mucopolysaccharide, and interference with the resolution of inflammation by inhibiting the motility of neutrophils, and the well-known corticosteroidal interference with healing, along with growth suppression so important in pediatric processes and congenital biliary atresia.

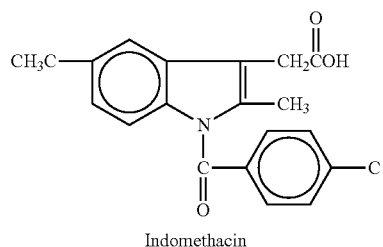

Indomethacin

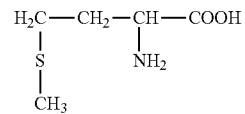

L amino acids of Subject Composition
Analogue side chain high energy groupings
Indol group, Tryptophan

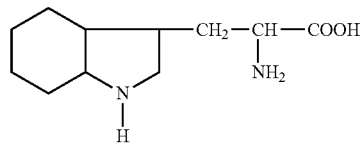

Methyl group, Methionine

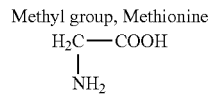

Acetyl group, Glycine

Pharmacological Properties. Indomethacin has prominent anti-inflammatory and analgesic antipyretic properties similar to those of the salicylates.

Although indomethacin is more potent than aspirin doses that are tolerated by patients usually do not produce effects that are superior to those of salicylates. Indomethacin has analgesic properties distinct from its anti-inflammatory effects, and there is evidence for both a central and a peripheral action. It is also an antipyretic.

| Indomethacin | L amino acids of Subject Composition |
|---|---|
| (1) potent inhibitor of the prostaglandin-forming cyclooxygenase | (1) In vitro studies by Shand et al. document significant anti-inflammatory activity reducing by 80% pro-inflammatory cytokine it-beta in CD tissue in 24 hrs. (significantly greater effect vs normal control bowel tissue.) Inflammatory antagonist countering inflammation is also favorably increased, (an increase in IL-1 receptor antagonist) - IL-RA |
| (2) It also inhibits the motility of polymorphonuclear-leukocytes (neutrophils), like many other aspirin like drugs, indomethacin uncouples oxidative phosphorylation in supratherapeutic concentrations | (2) L amino acids in subject composition documented in vitro by Shand, Meister, Aldhous et al. with added superiority of promoting neutrophil mobility to resolution in permeability studies |
| (3) depresses the biosynthesis of mucopolysaccharides. | (3) By stimulate law of mass action healing resolution and resynthesis |

Pharmacokinetic and Metabolism. Indomethacin is rapidly and almost completely absorbed from the gastrointestinal tract after oral ingestion. The peak concentration in plasma is attained within 2 hours in the fasting subject but may be somewhat delayed when the drug is taken after meals. The concentrations in plasma required for an anti-inflammatory effect have not been definitely determined but are probably less than 1 microgram per ml. Steady-state concentrations in plasma after long-term administration are approximately 0.5 micrograms/ml. Indomethacin is 90% bound to plasma proteins and also extensively bound to tissues. Indomethacin is largely converted to inactive metabolites, including those formed by O-demethylation (about 50%), conjugation with glucuronic acid (about 10%), and N-deacylation. Some of these metabolites are detectable in plasma, and free and conjugated metabolites are eliminated in the urine, bile and feces. Goodman and Gilman, Pharmacologic Basis of Therapeutics, $8^{th}$ edition, p. 659.

Pharmacognosy of Q101KC subject composition analogue to and analogue molar ratio of therapeutic L amino acids for pediatric Crohn's disease 5 amino salicylic acid, an active therapeutic agent and mainstay of pediatric Crohn's disease as well as serving as the functionally active grouping of Azulfidine (sulfacylic acid). Q101KC, and its components free L amino acids, are analogue to the foregoing 5 amino salicylic acid, its functional groupings and its molar ratio dosages. The analogue comparative dosages of Azulfidine being 500 mg, minimal dosage of Q101KC in active L amino acids, 775 mg, and 800 mg. as two 400 mg. tablets of Asacol, the active functional grouping of Azulfidine, generic name 5 amino salicylic acid, in a child over age 12 with PCD).

The free L amino acids historically were derived from the hydrolysis of protein. However, since all free L amino acids are not adequately available with that processing, it is now synthetically supplemented by synthetically produced L amino acids. These free L amino acids are now all synthetically available and synthetically prepared for subject composition Q101KC as in Neocate.

Pharmacognosy is that branch of pharmacology which deals with the biological, biochemical and economic features of natural drugs and their constituents. The pharmacognosy of Betaine, historically derived from beet sugar as a food, now may be obtained from other sources. Betaine was recently approved by FDA Orphan Drug Division for the therapeutic management of homocysteinemia and homocysteinuria for re-methylation of homocystein to methionine.

The corticosteroid therapeutic agents represent other mainstay drugs for PCD, and were historically derived from the Mexican yam. Similarly insulin, thyroxin, and vitamin B12 (for treatment of pernicious anemia) have similar interesting historical pharmacognosy, having been sourced from the Armour meat packing house. Historically, insulin was originally prepared from dog insulin then porcine and bovine origin and now is synthetically produced.

Two drugs with great magnitudes of nutritional pacesetting, insulin's pivotal function in nutritional metabolism of carbohydrate and associate metabolites, lifesaving in diabetics without this function, and thyroid medical setting of the nutritional metabolic rate of the body and all its tissue similarly vital.

Insulin's Function: Insulin stimulates the storage of glucose in the liver as glycogen and in adipose tissue as triglycerides and the storage of amino acids in muscle as protein: it also promotes utilization of glucose in muscles for energy. Insulin inhibits the breakdown of triglycerides, glycogen, and protein and the conversion of amino acids to glucose (gluco-neogenesis). These pathways are increased during fasting and in diabetic states. The conversions of amino acids to glucose and glucose to fatty acids occur primarily in the liver.

Thyroid hormone actions: Metabolic effects, calorigenic effect, regulation of growth and development, cardiovascular effects, inhibition of the secretion of TSH by the pituitary.

Q101KC analogue in base structure and functional biochemical groupings and side chain groupings as well as biochemical categories.

THERAPEUTIC IMPORTANCE OF HIGH ENERGY REACTIVE SIDE GROUPING AS IN Q101KC. Q101KC, when given in vivo, mimics the therapeutic effects of a medicament. In addition, Q101KC, in maximizing bioengineered therapeutic efficacy by in-vivo synthesis, provides pharmacodynamic therapeutic activity of high energy ionizing side chains in PCD and CBA therapy.

Bioengineered Structural Formulas Of Major Para-Aminophenol Derivatives, Comparative Reactive Side Chain Groupings Interrelations Mimicked by Q101KC Pharmacodynamic and Pharmacokinetic Chemistry: "The relationship between the drugs of this group and their metabolites is shown here. The antipyretic activity of the compounds resides in the aminobenzene structure." Introduction of other radicals into the hydroxyl group of para-aminophenol and into the free amino group of aniline reduces toxicity without loss of antipyretic action. Best results are obtained with phenolic alkyl ethers (e.g. phenacetin) and with the amides (e.g. acetaminophen, phenacetin)."

Pharmacokinetics and pharmacodynamics of high energy bonds of therapeutic L Amino acids ionizing side chain groupings in the anti-inflammatory healing resolution management of pediatric Crohn's disease and congenital biliary tree atresia.

Characteristics of Amino Acid Residues

| Mass (daltons) | Ionizing side chain | pK of side chain | ΔH ($Jmol^{-1}$) |
|---|---|---|---|
| Ala 71.08 | | | |
| Arg 156.20 | guanidinium | 11.5-12.5 | 48.4-54.6 |
| Asn 114.11 | | | |
| Asp 115.09 | B-carboxyl | 4.2-4.5 | 6.3 |
| Cys 103.14 | thiol | 7.5-8.5 | |
| Gln 128.14 | | | |
| Glu 129.12 | γ-carboxyl | 4.3-4.6 | 6.3 |
| Gly 57.06 | | | |
| His 137.15 | imidazole | 6.2-6.5 | 29-31.5 |
| Ile 113.17 | | | |
| Leu 113.17 | | | |
| Lys 128.18 | ε-amino | 9.8-10.4 | 42-48.4 |
| Met 131.21 | | | |
| Phe 147.18 | Pro | 97.12 | |
| Ser 87.08 | | | |
| Thr 101.11 | | | |
| Trp 186.21 | | | |
| Tyr 163.18 | phenolic hydroxyl | 10.2-10.5 | 25.2 |
| Val 99.14 | | | |
| α-carboxyl | | 3.5-4.5 | 6.5 |
| α-amino | | 6.8-7.9 | 42-54.6 |

Unique as anti-inflammatory agent also provides tissue healing resolution and repair cohesion synthesis of inflammatory disease damaged tissue of PCD and CBA along with component hydrogen bonding cohesion, electrostatic, zwitterion and van der Waals force bonding exemplified by high energy hydroxyl phenolic chemical ionizing side chain grouping of tyrosine. The alpha amino groupings of all L amino acids of subject composition analog to tissue and plasma composition provide twice the anti-inflammatory cohesive synthetic energy of tissue healing. This force is further doubled by an additional nitrogen grouping as in the diamino acids of the tissue healing arginine (guanidinium grouping) and the epsilon amino grouping of lysine. The additional cyclic nitrogen imidazole grouping of histidine equals the cohesive tissue healing energy bonding off the ionizing side chain phenolic hydroxyl group of tyrosine.

The symbol J. is representative of one Joule of energy of heat and work done by a force of one Newton acting over a distance of one meter.

Therapeutic subject composition (Q101KC) Pharmacologic Function added to the many Pharmacologic and Physiologic Functions of Amino Acids and L Amino Acids The discovery of the many functions of the plasma and tissue free L amino acids, reported in Goodman and Gilman's Basis of Therapeutics, $8^{th}$ edition, analogue in structure and function components of therapeutic subject composition (Q101KC).

Amino Acids. The CNS contains uniquely high concentrations of certain amino acids, notably glutamate and gamma-aminobutyrate (GABA); these amino acids are extremely potent in their ability to alter neuronal discharge. However, many physiologists were extremely reluctant to accept these simple substances as central neurotransmitters. This reluctance was based in part on conceptual problems of how to discriminate amino acids acting as transmitters from the same compounds acting as precursors for protein synthesis. The ubiquitous distribution of amino acids within the brain also posed problems in relating release to activity of a single neuronal circuit. Other important arguments against amino acids as transmitters were that they produced prompt, powerful, and readily reversible but redundant effects on every neuron tested; the dicarboxylic amino acids produced excitation, the monocarboxylic w-amino acids (e.g. GABA, glycine, β-alanine, taurin) produced qualitatively similar inhibitions (Kelly and Beart, 1975).

Discovery of the many functions of free L amino acids of therapeutic subject composition, "many physiologists were extremely reluctant to accept these simple substances" regarding other functions. "Reluctance" regarding "same compounds acting as precursors for protein synthesis." "In the past 20 years most of these conceptual arguments have proven to be unjustified and the evidence is quite strong that certain amino acids especially GABA, glycine, and glutamate, are central transmitters." A function in addition also a function of precursor for protein synthesis, as well as an anti-inflammatory function.

For example, several amino acids (as in therapeutic subject composition have an inhibitory activity not only regarding neural but also their anti-inflammatory activity, e.g. glycine.

Weirman and associates (1968) assembled neurochemical and electrophysiological evidence that has established glycine as the inhibitory transmitter between spinal interneurons and motorneurons.

"Glycine is the most abundant amino acid with inhibitory activity found in the ventral-quadrant gray matter of the spinal cord, and concentrations of glycine drop in proportion to the degeneration of ventral-quadrant interneurons following transient ischemia of the cord. Glycine has also been localized to spinal interneurons by electron-microscopic autoradiography. It is concentrated in nerve terminals."

"The major evidence that favors glycine as the mediator of intraspinal postsynaptic inhibition is the selective antagonism of its effect by strychnine The derivatives of these analogue tissue components and concentrations N-methyl-D-aspartate (NMDA), "It is possible that drugs with similar action may prove therapeutically useful in salvaging." Such tissues as "neurons threatened by hypoxia following trauma or stroke."

This concept illustrates that analogue biochemical tissue components also are representative of therapeutic agents and are particularly important in the disease damaged tissue salvaging component of the inflammatory healing resolution cycle stressed here. These L amino acids are metabolites per se representing both the end result of protein catabolism and the beginning of raw material metabolites for new protein synthesis. In using these metabolite analogue tissue and plasma components and their component high energy ionizing side chain groupings of subject composition for this therapeutic end, it is possible that this synergy, co-synergy interplay and interaction may be the final common pathway metabolite for these respective therapeutic actions to occur and take hold.

This entity is illustrated by an analogue therapeutic compound, Indomethacin. (Goodman and Gilman's the Pharmacological Basis of Therapeutics, $8^{th}$ Edition, 659). Pharmacokinetics and Metabolism. "Indomethacin is largely converted to inactive metabolites." Its activity is dependent on the intact active molecule. These pharmaceutical metabolite L amino acids appear to share these same pharmacokinetic and metabolism features as Indomethacin. Indomethacin unfortunately "depresses the biosynthesis of mucapolysaccharides; "It also inhibits the motility of polymorphonuclear leukocytes;" the neutrophil, both mechanisms essential in the healing resolution phase of inflammation, a most important pharmacokinetic asset of subject composition.

Pharmacologic rationale for clinical efficacy of Q101KC in PCD and CBA and their Subsets For the first time, through the work of Girsh (exhibit and patent pending applications) the mechanisms and the rationale for 85% efficacy up to 89% efficacy in some reports) in recovery of PCD has been elucidated as analogue to medications such as existing anti-inflammatory potent medications, working synergistically in an analogue fashion to medications such as the non-steroidal anti-inflammatory medications and analogue to the synergism noted in such medication as aromatic amines of triple sulfonamides, analogue to the aromatic amines such as tyrosine, tryptophan and phenylalanine as well as co-synergistic effects of aliphatic amines all representative of the free L amino acids and amino acid such as but limited to glycine of Q101KC.

Unique to Q101KC is the continued healing efficacy of the diseased tissue of PCD and CBA and their subsets, as well as the anti-rejection analogue to cyclosporin, the oligopeptide, along with the 3 carbon uneven numbered 8 propionic acid amino acids with anti-microbial effects. These anti-microbial effects are companion to anti-inflammatory tissue healing actions countering microbial overgrowth as present in chronic intestinal inflammatory disease and associated tissue damage of PCD, (such as but not limited to anti-fungal and anti-yeast) an additional therapeutic factor is noted by some observers addressing microbial etiologic factors. Pharmacologic tissue healing functions and structures not available in other medications:

Subject composition Q101KC and components L amino acids and amino acid glycine, so prepared as analogue to and mimicking human tissue and in structural molar ratio and in function of human tissue. Q101KC imparts to the tissue the stimulus and components to repeatedly and constructively reconstitute itself. Such radiographic documentation includes complete 1-2 to 4 week clearance of inflammatory radioactively tagged markers of inflammatory permeability.

These findings of dramatic radiographic anti-inflammatory tissue healing therapeutic response to Q101KC coincide with clinical normalization of PCD. This is further evidenced by normalized clinical activity index scores as well as normalization of such companion systemic markers of inflammation, erythrocyte sedimentation rate and C reactive protein. The normalization of growth and puberty represent another index of systemic normalization by Q101KC of the all encompassing effect of the PCD disease and medication side effects including corticosteroids.

This is further exemplified by the Q101KC therapeutic prevention of the need for surgical correction of the fistulae, (a complication of PCD) in 63% of the patients. Q101KC has been found to reduce the surgical mortality risk of fistulae correction which is as high as 70% to 15%. These same non-intrusive and noninvasive therapeutic principles of Q101KC are applicable to both PCD and CBA: the reconstitution of immunologic self along with anti-rejection of grafted tissue as well as seriously damaged tissue. Q101KC being anti-rejection, specifically its component glycine, alanine, valine, and leucine offer, anti-rejection as well as anti-inflammatory tissue healing activity so needed and so well adapted to CBA and its subsets (as well as PCD and subsets) of CBA pre and post hepatectomy liver transplantation graft subsets. To design a medication with such advanced bioengineering analogue to structure and function anti-inflammatory, tissue heating requirements, anti-rejection of PCD and CBA and their subsets' diseases countering medication with concurrent tissue healing structures and functions being simultaneously analogue to structure and function of human tissue including stimulus for protein synthesis of tissue represents the essence of the bioengineering goal of stem cell therapy, mimicking and analogue to the newest forefront of pharmacologic therapy stem cell therapy. This therapy Q101KC is separated from the countless inherent invasive risks and non-immunologic self risks of embryonic stem cell that Q101KC mimics and is analogue to.

Similar advantages are seen with Q101KC non-steroidal anti-inflammatory analogue mimicry without the disadvantages and major side effects of NSAID. Q101KS's efficacy are specific to inflammatory diseases of the intestinal tract and biliary tract and represent here a two week Q101KC therapeutic response test. This response test also represents the differential diagnostic test since the colonic inflammatory bowel disease, ulcerative colitis will not show the degree of therapeutic response to Q101KC as pediatric Crohn's disease (ileitis small intestinal tract) and congenital biliary atresia of the hepatobiliary tract L amino acid particularly such as, but not limited to, the 3 aromatic amino acids in subject composition, tyrosine, phenylalanine and tryptophan, similar and analogue synergistically to the synergisti aromatic amino formulation triple sulfonamide.

The said foregoing analogue structures and functions of subject composition Q101KC are all a simultaneous continuum of overlay structures and functions and analogue to the overlay structures and functions of normal human tissue inflammatory and anti-inflammatory healing cycle that Q101KC including but not limited to Q101KC L amino acid and amino acid components which are also analogue in structure and function as well as in molar ratio. These multiple pharmacodynamic functions of Q101KC are not only amino acid and L amino acid analogue in molar radio to human tissue healing and stimulate tissue protein synthesis of diseased and damaged tissue that are also anti-inflammatory as NSAID also analogue in function to the corticosteroids but also anti-rejection analog to cyclosporin. Q101KC has added advantages of being devoid of interference with healing as in the corticosteroids interference with protein tissue synthesis (as in small molecular NSAID medications such as but not limited to aspirin and indomethacin) and neutrophil motility (as in small molecule NSAID such as limited to indomethacin) of the nonsteroidal anti-inflammatory drugs as well as the disturbance in kidney function in 20 percent of the anti-rejection cyclosporin (cyclic oligopeptide) treated patients.

Immunologic self, subject 2, and its application to subset 1 and PCD and its subset in regard to relatively risk free anti-rejection effects of Q101KC. The pharmacodynamics herein of Q101KC anti-rejection anti-inflammatory relatively risk free medicament analogue effects of Q101KC makes it highly applicable not only for its use in subset 1 as well as PCD and its subsets wherein inflammatory disease damage is so extensive that immunologic self of these target tissue are distorted, until repaired by Q101KC and re-established as immunologic self. This pharmacodynamic reaction of Q101KC anti-inflammatory anti-rejection tissue healing and Q101KC's component L amino acids and their reactive high energy, ionizing, (and non-ionizing) side chain groupings are all analogue in structure and function, the in vivo synthesis of human tissue as well as medications derived therefrom. All these effects permit, stimulate, facilitate and accelerate tissue healing effects and recuperative systemic effects, in diseased tissue, local and system effects of disease repair. All these effects of Q101KC component L amino acid and amino acid being analogue to human tissue as well as the molar ratio of tissue are, therefore, analogue to stem cell function, the newest forefront of medicament development all highly valuable in the profound efficacy of Q101KC in the therapy of PCD and CBA.

A Significant Therapeutic Accomplishment:

To have such a therapeutic pharmaceutical activity as Q101KC to replace corticosteroids in PCD as to bring about a prolonged remission, 85% up to 89% efficiency observed in an excess of several hundred patients, well documented in the literature in controlled, placebo studies, randomized studies, to not only replace corticosteroids, but also has been recognized by most of these observers to be more efficacious.

This astute clinical observation of tissue healing effect to out perform corticosteroids which interferes with healing is based upon the ability of this therapeutic pharmaceutical and pharmacodynamic activity of Q101KC component of the L amino acid and amino acid glycine to be structurally and functionally analogue to the small molecule NSAID with the added advantage over NSAID in not interfering with healing, companion to its anti-inflammatory effect.

This remarkable tissue healing therapeutic superiority of Q101KC effect is due to the fact that it is also dualistically analogue to the L amino acids and molar ratios of human tissue permitting this diseased tissue healing capacity of PCD, representative of inflammatory disease of the intensive and ileum, and CBA representative of inflammatory disease of the biliary tract, to return to a normal state, (an additional and unique capacity of Q101KC therapeutic pharmaceutical activity).

This normalization by Q101KC and component synergistic amino acids including but not limited to glycine of clinically defined and measured inflammatory changes associated with the multiplicity of abnormal inflammatory permeability (including tracking by radiograph of radioactively tagged reinjected autologous neutrophil reports of studies that parallel anti-inflammatory healing clinical recovery and reversal of PCD to normal.

At the same time, to be able to reverse growth retardation (efficacy with Q101KC in excess of 90%—personal communication Seidman ref 26) and puberty retardation Q101KC within 6 weeks as well as to reduce the surgical complications, specifically mortality, from 70% to 15% and at the same time to permit 63% of patients avoid required surgical care for a PCD complication of fistulae, is a remarkable pharmaceutical accomplishment.

This remarkable contribution is not present in other pharmaceutical therapeutic agents. Since Q101KC can replace corticosteroids, growth retardation in PCD due to corticosteroids can be reversed. In addition, since PCD is such a severely systemic debilitating disease associated with growth retardation, Q101KC is another factor in reversing this major complication in PCD while reversing the disease.

In this same application we are able to add further documentation since my patent pending application and exhibit, the presentation of specific anti-inflammatory, cytokine, actively demonstrated in PCD. This Crohn's disease biopsied tissue anti-inflammatory effect of Q101KC with 80% reduction of inflammatory cytokines measured and compared to normal tissue (a 24 hour tissue culture observation) along with the observation of elevated receptor cytokine antagonism levels.

The unique Q101KC analogue therapeutic activity discovery of the pharmacodynamics and pharmacokinetics of the L amino acid synergistic composition of Q101KC (also analogue to human tissue), presents a composite of practical and exciting component group of compounds of Q101KC, plus pre-clinical and clinical observations have carried over the efficacy from small intestinal inflammatory disease to hepatobiliary tract inflammatory disease of CBA, available for designation for PCD and CBA and their subsets. These orphan diseases even though they are of formidable prognostic concerns and severity, are now being offered a non-invasive optimistic outlook, without the usual risks of therapy with such magnitude of efficacy.

In PCD e.g. (Teahon) corticosteroids cannot be stopped without the consequences of major PCD recurrences in 1 to 2 days, possibly one week, whereas Q101KC can be stopped without the use of corticosteroid without a major recurrence for 6 months, majority, 70% of Q101KC patients will not have recurrence even if stopped for one year.

Resulting in a therapeutic test for PCD intestinal inflammation or CBA, biliary inflammation, Q101KC can therefore be used as a therapeutic response differential diagnostic test wherein ulcerative colitis will not show the degree of therapeutic response to Q101KC as pediatric Crohn's disease (ileitis of small intestinal tract) and congenital biliary atresia of the hepato-biliary tract.

If not responsive, a negative therapeutic test would be suggestive of ulcerative colitis colonic inflammatory disease.

Tabulation

Controlled Studies including, Double-Blind Studies, Placebo Controlled Studies—Efficacy of Q101KC in "PCD and *CBA and their *subsets—Statistics Tabulation of Documentation and Publications.

Shand A, Meister D, Aldhous M, Anderson N and Ghosh S Direct Anti-inflammatory Effect of Elemental Diet on Crohn's Tissue In Vitro, Gut 2000, 46: Suppl II: A43

In-vitro studies of 6 biopsies of Crohn's diseased tissue, 5 normal controls, both in culture medium.

Key Contributory Conclusions

"This is the first demonstration of a direct anti-inflammatory effect of an elemental diet in Crohn's disease" with a "reduced production of pro-inflammatory cytokines IL-one beta by more than 80 percent in 24 hours" and "a relative increase in a IL-1 beta," "casein did not result in any reduction of inflammatory cytokines". "Replacing the" free L "amino acids with whole protein casein whey, in organ culture did not abolish the anti-inflammatory properties." Therefore, without free L amino acids anti-inflammatory activity is not present (in vitro, when the same amino acids are bound in the protein polymer form also demonstrating that this is not a nutritive anti-pathogenic pharmacokinetic function).

Sanderson I R, Boufon P, Menzies I, and Walker-Smith J A, Improvement of Abnormal Lactulose/Rhamnose Permeability in Active Crohn's Disease of the Small Bowel Number of cases: 19 (ages 11-17)

6 normal controlled permeability studies

19 PCD children, abnormal permeability studies which improved, along with disease activity index score after treatment with Q101KC. Seven on steroids were able to reduce or stop the corticosteroids.

Russell R I. Editorial, The management of gastrointestinal fistulae, (a complication of Crohn's disease)—Gut 1975: 16:68-79.

Number of cases: 13 responded with Q101KC: 11; 85%

Key Contributory Conclusion:

Surgical mortality reduction with Q101KC therapy applied to major CD complication of fistulae, a surgical mortality reduction from more than 70% surgical mortality to 15% surgical mortality risk, (more than 50% surgical mortality reduction in surgical care of fistula complicating Crohn's disease).

O'Morain C, Segal A W, Levi A J. Elemental diets in treatment of acute Crohn's disease. Br Med J 1980:281:1173-1175

Number of cases: 29, 24 treated with Q101KC for four weeks, 8 received no other treatment, 3 received steroids—30 mgm per day which was reduced to 10 mg per day in 2 weeks.

O'Morain C, Segal A W, Levi Al. Elemental diet as primary treatment of acute Crohn's disease: a controlled trial. Br Med J 1984:288:1859-1862

Number of cases: 9 responded with Q101KC: 8; 89%

Key Contributory Conclusions:

Control trial of 21 patients, exacerbations randomized, received either corticosteroids or Therapeutic Subject Composition, Q101KC for 4 weeks. Those on Q101KC "improved as much as, by some criteria, more than steroid group".

"Nutritional improvement unlikely to be responsible because clinical improvement starts long before positive nitrogen balance develops." "Principal difficulty—unpalatability."

Teahon K, Bjamason I, Pearson M, Levi A J. Ten years experience with elemental diet in the management of Crohn's disease. Gut 1990:31:1133

Number of cases: 113 responded with Q101KC: 96; 85%

96 treated by P.O.

17 treated with nasogastric tube 96 successful, 17 unsuccessful

Key Contributory Conclusions:

"Ten years experience with Q101KC management of Crohn's disease:" "Versus steroid induced remissions—no significant difference in relapse rate."

Some authorities reported that in many ways Q101KC was superior to corticosteroids in that flare ups did not occur immediately upon stopping Q101KC, but after 6 months only ⅕ relapsed and 8 to 10% after one year. This is in sharp contrast to stopping steroids. In one year the majority, 70% still did not relapse. Steroids cannot compete with this prolonged effect.

O'Morain C, et al. Elemental diet in acute Crohn's disease. Arch Dis Child 1983

Total number, 14 PCD Cases (ages 6-20)

Improvement between 1-2 weeks after start of treatment with Q101KC therapeutic subject composition. In addition, regarding poor growth, after 3 months of treatment 3 achieved their normal height percentile with Q101KC therapy.

Morin C L, Roulet M, Roy C C, Webber A.

Continuous elemental enteral alimentation in children with Crohn's disease and growth failure. Gastroenterology 1980: 79:1205-1210

Prior to this report, treated 10 PCD cases with complete remission with three weeks of Q101KC therapeutic subject composition only. Encouraged with that success he then treated 4 children with PCD complicated by growth and puberty retardation. During 6 week course of Q101KC these 4 children gained an average of 1.8 cm in height which equals their annual height gain rate the previous 2 years before using Q101KC (illustrated by 4 graphs and comparative height and puberty change photograph).

Growth retardation and puberty retardation were reported in 15% to 30% of children with PCD. Similar response of growth and puberty retardation was further documented by Layden T, Rosenberg J, et al. Reversal of growth arrest in adolescents with Crohn's disease after parenteral alimentation—Gastroenterology 1976: 70: 1017-21, Kelts D G, Grand R J, et al. Nutritional basis of growth failure in children and adolescents With Crohn's disease. Gastroenterology 1979: 76: 720-7. Strobel C T, Byrne W J., Ament M E Home parenteral nutrition with Crohn's disease, an effective management alternative. Gastroenterology 1979: 77: 272-9. O'Morain C, Segal A W, Levi A J. Elemental diets in treatment of acute Crohn's disease. Br. Med J 1980: 281: 1173-75.

Seidman E G, et al. Nutritional therapy of Crohn's disease in childhood. Dig Dis Science 1987:32(Suppl): 825.

Total number, 100 PCD cases with severe disease, without complications were treated with Q101KC, therapeutic subject composition, 89% responded to Q101KC therapy PCD subset of fistulae complication: 63% responded to Q101KC therapeutic subject composition, without the requirement of surgical care. Relapse did not occur until three months after treatment was stopped, in some cases.

With the use of Q101KC subject composition, those that did require surgical care had a decrease in mortality from 70% to 15%.

Belli D C, et al. Chronic intermittent elemental diet improves growth failure in children with Crohn's disease. Gastroenterology 1988:94:603-610.

Number of PCD cases: 8 with subset complication of growth retardation, were treated with Q101KC, therapeutic subject composition, and were compared to 8 controls with comparable PCD and growth retardation. Those receiving Q101KC therapeutic subject composition grew more than twice as much in height (7 cm) in the observation year than the control group (1.7-2.9 cm). This growth stimulus to Q101KC treated patients occurred even though the treated patients received Q101KC therapy as infrequently as one month every three months for one year. Both treated and controlled PCD patients had adequate calorie intake. Therefore Q101KC had a significant effect intrinsic to the therapy, and lessened the need for corticosteroids as well as controlling PCD. "Long term growth of PCD patients on corticosteroids was unsatisfactory. Q101KC makes the decrease or discontinuance of corticosteroids possible in offering successful management of PCD. Belli's literature review revealed 15% to 40% incidence of growth retardation in PCD.

Mordan A M, Hunter J O, et al. Treatment of active Crohn's disease by exclusion diet: East Anglian Multicenter Controlled Trial. Lancet 1993: 342: 1131-1134.

Number of cases: 93 responded with Q101KC, therapeutic subject composition: 78; 84%

Key Contributory Conclusions:

Double-blind in that patents using Q101KC therapeutic subject composition were given placebo identical to corticosteroids. 43 patients of the initial 136 refused to continue with the treatment because of unpalatability. "Q101KC is as effective in producing remissions of Crohn's disease as in corticosteroid treatment."

Teahon K, et al. The effect of Elemental diet on intestinal permeability and inflammation in Crohn's disease. Gastroenterology 1991: 101:84-89.

Number of cases: 34 responded with Q101KC: 27; 85%

Key Contributory Conclusions

"Current study shows for the first time that treatment with Q101KC alone reduces the acute inflammation in patients with Crohn's disease showing that the treatment is not just symptomatic—"Documented by 2 to 4 week reversal of abnormal intestinal mucosal permeability radiographed, measured by radioactively tagged neutrophils, (see radiograph).

Tabulation Totals

Total CD cases

Treated with Q101KC, therapeutic subject composition 457

Response 85%

Pediatric CD 206 cases: adult CD 251 cases

Total CBA cases:

Subset 1: non-surgical, treated with Q101KC: 1 case, averting transplant

Subset 2: surgical, hepatectomy with liver transplant: 11 cases treated with Q101KC The best evidence of therapeutic response to subject composition and pharmaceutical evidence of efficacy.

Crohn's Disease in Childhood and Q101KC therapeutic Response in PCD and Subset #1

From the British National Association of Crohn's Disease and Colitis, London, England Ling. S. Senior Registrar in Pediatric Gastroenterology and Nutrition, Yorkhill Hospitals, Glasgow. Crohn's Disease in Childhood, NACC Autumn, 1999.

Use of Q101KC subject composition in management of PCD and clinical response "far more than expected" with "the benefit lasting longer and the side effects of steroids are avoided" a most important therapeutic goal in PCD treatment particularly in striving to minimize growth suppression complicating the use of steroids in treating Crohn's disease in childhood.

"Fortunately, a chance observation more than 20 years ago led to the development of a therapy that counteracts the effect of inflammation on nutrition and growth, and which is now widely used in clinical practice. Adults with CD preparing for surgery in the 1970's were given a liquid "elemental" diet and their symptoms improved far more than expected."

"However, if inflammation remains unrecognized or undertreated, or recurs frequently, then nutrition and growth deteriorate. If such problems are protracted and coincide with the growth spurt during puberty, then the height the child eventually reaches as an adult maybe less than if the inflammation had not occurred."

"Subsequent studies demonstrated that if a child with active CD is asked to stop eating a normal diet and to take instead a liquid feed for six to eight weeks, the intestinal inflammation is likely to subside and the child's growth is likely to improve. When compared to treatment with steroids, liquid feeds are slightly less likely to settle the inflammation, but the benefit may last longer and the side effects or steroids avoided. Many doctors who treat adults prefer to use Steroids to quieten active CD, but in the treatment of children, feeding has an overwhelming advantage; it maintains growth."

Q101KC cumulative effect affecting normalization of linear growth and PCD even when given concurrent with food 1 month every 4$^{th}$ month for one year.

Efficacy of Therapeutic Subject Composition, Q101KC, in Pediatric Crohn's Disease Treatment, Subsets 1 and 2

PCD Subset 1: Growth and Puberty Retardation in PCD responding to therapeutic subject composition Q101KC O'Morain C, et al. Elemental diet in acute Crohn's disease. Arch Dis Child 1983

Total number, 1 d PCD cases (ages 6-20), Improvement between 1-2 weeks after start of treatment with Q101KC therapeutic subject composition. In addition, regarding poor growth after 3 months of treatment 3 achieved their normal height percentile with Q101KC therapy.

Morin C L, Raulet M, Roy C C, Webber A. Continuous elemental enteral alimentation in children with Crohn's disease and growth failure. Gastroenterology 1980:79:1205-1210

Total number, 14. The 4 PCD subset with growth retardation responded to Q101KC with normalization of growth, the remaining 10 PCD cases (uncomplicated) also responded. Prior to this report, treated 10 PCD cases with complete remission with three weeks of Q101KC therapeutic subject composition only. Encouraged with that success he then treated 4 children with PCD complicated growth and puberty retardation. During 6 week course of Q101KC these 4 children gained an average of 1.8 cm in height which equals their annual height gain rate the previous 2 years before using Q101KC (illustrated by 4 graphs and comparative height and puberty change photograph).

Growth retardation and puberty retardation were reported in 15% to 30% of children with PCD. Similar response of growth and puberty retardation was further documented by: Layden T, Rosenberg J, et al. Reversal of growth arrest in adolescents with Crohn's disease after parenteral alimentation. Gastroenterology 1976: 70:1017-21.

Kelts D G, Grand R J, et al. Nutritional basis of growth failure in children and adolescents with Crohn's disease. Gastroenterology 1979: 76: 720-7.

Strobel C T, Byrne W J, Arment M E. Home parenteral nutrition in children with Crohn's disease, an effective management alternative. Gastroenterology 1979: 77: 272-9.

O'Morain C, Regal A W, Levi A J. Elemental diets in treatment of acute Crohn's disease. Br. Mod J 1980: 281: 1173-75.

Belli D C, et al. Chronic intermittent elemental diet improves growth failure in children with Crohn's disease. Gastroenterology 1988:94:603-610.

Number of PCD cases: 8 with subset complication of growth retardation, wen: treated with Q101KC and were compared to 8 controls with comparable PCD and growth retardation. Those receiving Q101KC therapeutic subject composition grew more than twice as much in height, (7 cm) in the observation year than the control group (4.7-2.9 cm). This growth stimulates to Q101KC treated patients occurred even though the treated patients received Q101KC therapy as infrequently as one month every three months to one year. Both treated and controlled PCD patients had adequate calorie intake. Therefore Q101KC had a significant effect intrinsic to therapy, and lessened the need for corticosteroids as well as controlling PCD. "Long term growth of PCD patients on corticosteroids was unsatisfactory." Q101KC makes the decrease or discontinuance of corticosteroids possible in offering successful management of PCD. Belli's literature review revealed 15% to 40% incidence of growth retardation in PCD.

Personal communication (ref 79) with Seidman, Univ Hosp. Ped Dept. Montreal, Canada, 9/25/02, "90% of PCD with growth retardation respond with linear growth using Therapeutic Subject Composition, Q101 KC." Heretofore the nasogastric tube has been used to by-pass lack of palatability.

Tabulated Documentation

Establishment of normal linear growth using Q101KC in growth and pubertal retardation, efficacy of Q101KC in the Treatment of PCD, Subsets 1 and 2:

14 of 14 growth retardation cases 4 growth retardation cases 8 of 8 growth retardation cases Total number of cases: 26 All responded to Q101KC This high index of efficacy conforms with "90% of PCD with growth retardation respond with linear growth using Q101KC." Seidman Personal communication 9/25/02.

Compliance a major problem since not used as a pleasant pediatric medicament. With Q101KC 15% fail to comply (not used in medicament format).

Dr. Seidman concurred that this would be of significance having this as a pleasant pediatric medication as presented here as Q101KC. It is to be noted that more than a decade of time has passed and Q101KC has continued to pass the test of time with normalizing growth and pubertal retardation with a rating as high as 90%.

Positive effects, not transient, efficacy persistent, even if given one out of four months. This is equal to 25% of the dosage used by others. Clear cut impact on end point of growth acceleration. Applicable here when used at prescribed dosage.

The height and weight for each patient are shown for the 2 years preceding Q101KC equivalent during the 6 weeks course of Q101KC equivalent and the follow up year. The age of each patient is shown at the start of the Q101KC equivalent. Patient D had surgery two months after Q101KC equivalent and had a second spurt of growth with pubertal changes.

Correction of Growth and Pubertal Retardation in PCD Subset

Growth catch up of 2.4 cm in 6 weeks after stopping steroids, replaced by Q101KC anti-inflammatory healing subject composition equivalent, normalization systemic signs of PCD, controlling PCD and tissue healing.

Pediatric Crohn's Disease, Subset 2: Fistulae

Total number, 100 PCD cases severe disease, without complications were treated with Q101KC equivalent, 89% responded to Q101KC equivalent therapy. PCD subset of fistulae complication, 63% responded to Q101KC equivalent therapeutic subject composition, without the requirement of surgical care. Relapse did not occur until three months after treatment was stopped, in some cases. With the use of Q101KC subject composition, those that did require surgical care had a decrease in mortality from 70% to 15%. Seidman E G, et al. Nutritional therapy of Crohn's disease in childhood. Dig Dis Sci 1987:32(suppl): 825.

TABLE 3

Pediatric Crohn's Disease. Graphic Analysis of Pharmacologic
analogue advantages of Q101KC Anti-inflammatory Tissue Healing
PharmacoDynamics in Pediatric Crohn's Disease

| Structure and Function of L amino, acid, Glycine Analogue to anti-inflammatory medication and side chain, high energy, ionizing groupings (as in small molecule NSAID) Pharmacodynamic effect and decreasing inflammatory cytokine and increasing receptor antagonism to inflammatory cytokines. Seen with similar structured analogue anti-inflammatory NSAID. | Structure and Function of L amino acid and amino acid glycine Analogue to tissue Dosage administered as anti-protease activity arresting neutrophils enzymatic action, stimulating protein synthesis countering increased permeability characteristic of inflammation Pharmacodynamic anti-protease stimulates protein synthesis and tissue healing effect All components are synergistic to tissue healing NSAID and steroids are dissimilar in structure and function and not analogue tissue. The L-amino acids and amino acid components of Q101KC analogue to tissue structure are not functionally present in NSAID and corticosteroids. | Clinical Applications Growth retardation in PCD is 15% to 30% in children with PCD Components of anti-inflammation pharmacodynamics along with growth stimulating action Countering growth retardation of corticosteroid and of disease | Pharmacodynamics tissue healing anti-inflammatory, anti-permeability, anti-protease, stimulating protein synthesis and tissue healing effect - analogue and synergistic to tissue |

Graphic Analysis of Pharmacologic Advantages of Q101KC
Anti-inflammatory Tissue Healing Pharmacodynamics in
Congenital Biliary Atresia.

| Structure and Function of L amino acid, Glycine Analogue to anti-inflammatory medication and side chain, high energy, ionizing groupings (as in small molecule NSAID) Pharmacodynamic effect and decreasing inflammatory cytokine and increasing receptor antagonism to inflammatory cytokines. Seen with similar structured analogue anti-inflammatory NSAID. | Structure and Function of L amino acid and amino acid glycine Analogue to tissue Dosage administered as anti-protease activity arresting neutrophils enzymatic action, stimulating protein synthesis countering increased permeability characteristic of inflammation Pharmacodynamic anti-protease stimulates protein synthesis and tissue healing effect. All components are synergistic to tissue healing NSAID and steroids are dissimilar in structure and function and not analogue to tissue Tissue healing reversal to normal tissue preventing need for graft. | Subset of CBA Post hepatectomy and donor graft Analogue to anti-rejection medication such as cyclosporin Q101KC amino acid tissue analogue and synergism Alanine, valine, leucine and glycine are analogue to the components of the oligopeptide cyclosporin structure. The net effect is to reduce the dosage and need for such anti-rejection medications as cyclosporin and the 20% risk of loss of kidney function. Analogue to tissue and therefore analogue to immunologic self in tissue rebuilding and tissue healing and preventing dysmetabolism in the constant restructuring of immunologic self, therefore preventing graft rejection. Decreasing the need for corticosteroids with counterproductive interference with tissue healing. | Pharmacodynamics Tissue healing, Anti-inflammatory Anti-permeability, Anti-protease, Stimulating protein Synthesis and Tissue healing effect - analogue and synergistic to tissue THE L AMINO ACIDS AND AMINO ACID COMPONENTS OF Q101KC ANALOGUE TO TISSUE STRUCTURE ARE NOT FUNCTIONALLY PRESENT IN NSAID AND CORTICOSTEROIDS. |

Transplantation Medicine and the Practice of Allergy & Immunology; Leonard S. Girsh, M. D.

BILIARY ATRESIA, Impact of Subject Composition Regarding Scheduled Liver Transplant An infant, age 3 weeks, wt. 6 lbs., birth weight 7 lbs. was awaiting a liver transplant. The diagnosis was Biliary Atresia, which was substantiated surgically.

The patient's grandfather requested our clinical strategy in view of the patient's failure to thrive and the awesome planned therapy.

Because of the frequency of φw's milk allergy in infancy and to help improve the preoperative, operative and postoperative care, hypoallergenic milk plus the feature of elemental feeding was prescribed (Neocate).

Consideration Review—

If gastrointestinal allergy existed in association with gastrointestinal congestion, the congestion could conceivably extend to the biliary region with possible modified patency of the biliary tract.

The clinical course was much more dramatic than anticipated, absence of jaundice resulted with excellent weight gain and the patient was removed from the Transplantation List leading to subject composition.

ANAPHYLAXIS TO RENAL DIALYSIS—Impact of Allergy Care

A female, age 16, presented with severe anaphylaxis to renal dialysis. The renal dialysis was necessitated by three renal transplant rejections.

We requested the family to bring in all obtainable (by prescription) dialysis equipment from the area for comparative scratch testing of saline washings of equipment. The only negative finding was with Renal Systems' equipment which is specially coated to prevent leaching out of the plastic.

The patient was reactive by history and exclusion to the Clorox used for sterilization for equipment to be reused in the same patient.

Clinical Course: Excellent

CORNEAL TRANSPLANTATION IN ALLERGIC PATIENTS—Impact of Allergy Care

Three allergic patients scheduled to receive corneal transplants were referred to our office by Ophthalmology specialists in corneal transplantation.

The impression, which proved to be correct, was that the corneal transplant rejection could be prevented with necessary allergy care prior to surgery.

After examination and treatment* of allergic rhinitis and rhino-sinusitis the corneal transplantations were successful and the clinical course was excellent.

*Corticosteroids were not used.

The Pathogenesis of Biliary Atresia as Seen by this Review:

Liver biopsy and the extra hepatic biliary system from five patients who underwent portoenterostomy for Biliary Atresia were studied by light microscopy to delineate the character and distribution of the anatomic lesions, and by culture and immunofluorescence techniques for evidence of two viruses (cytomegalovirus and hepatitis B) which have been suspected of playing a role in the genesis of Biliary Atresia.

The liver biopsies showed typical findings, with variable giant cell transformation, cholestasis, and prominent bile duct proliferation. In the extra hepatic biliary system, in all five cases there was lumen obliteration in the common hepatic duct, and in three cases there was also comparable obliteration in the common bile duct. Proximal to the areas of obliteration, no lumen dilation was evident. In the areas of obliteration there was evidence of a resolving inflammatory process. Where the lumen was present, it tended to be small, especially in the hepatic and common ducts. In the portahepatic there appeared to be various stages of an evolving lesion, the earliest stage of which included extensive active epithelial injury with developing fibrosis, and the latest, more advanced fibrosis with reduction in duct lumen area.

In the earlier stage, a dense inflammatory infiltrate, with small number of polymorphonuclear leukocytes, numerous lymphocytes, plasma cells, and eosinophils, was present. In the latter stage mononuclear cells predominated, polymorphonuclear leukocytes were scant, but eosinophils were often still quite prominent. These histologic findings demonstrate the presence of active ductal epithelial injury, at least in the porta hepatic, in this age period. There was no evidence of cytomegalovirus in any case or of hepatitis B in three of five cases. In two cases, one of the less specific techniques showed suggestive evidence of hepatitis B in the liver. These latter findings suggest that other viruses need to be sought, or cases should be studied at an earlier stage for the presence of these viruses, or both.

Although the syndrome of "infantile obstructive cholangiopathy" (neonatal hepatitis, choledochal cyst, and Biliary Atresia) (9) have been associated with a number of diseases (13) the pathogenetic basis for this association is unclear. In the many cases that have no associated disease, the etiology and pathogenesis are completely unknown. Despite some indication of benefit from the use of portoenterostomy (Kasai procedure), the problem of prolonged infantile obstructive jaundice remains a serious one, with significant mortality and morbidity, and it appears that a completely satisfactory solution will not be reached with an understanding of the fundamental etiology(ies) and/or pathogeneses involved. In an attempt to contribute to such an understanding, we have examined the liver and extra hepatic biliary tree from five consecutive patients who underwent portoenterostomy for Biliary Atresia, seeking clues as to etiology and pathogenesis by using light microscopy on serial sections of the extra hepatic tree and by using immunofluorescence and viral culture techniques on both liver and extra hepatic tree.

This paper reports the results of therapeutic trial regarding allergic disease and immunopathy incorporated into the ideal pre operative and post operative nutritional care.

The extensive inflammation, now recognized as being associated with asthma is also seen here.

The periductular obstructive inflammation is reminiscent of the peribronchial inflammatory thickening associated with recurrent bronchiolitis so characteristic of the infantile and childhood asthmatic syndrome.

Both entities are triggered by viral infections and are perpetuated by milk hypersensitivity and relieved by milk avoidance as in this elemental diet used here. The disorganization, caused by inflammation, that occurs in these pathologically similar conditions, Congenital Biliary Atresia* and Infantile Asthma*, resulting in failure of organ function brings to mind the current term "remodeling", should more aptly be called "dismodeling" or functional and structural "dismanteling".

A change that Asthma has undergone in the recent 1-2 decades, having been intimately involved in the treatment and pathogenesis for more than 3 decades; hence a discussion of the current concepts of the pathogenesis of Asthma and its treatment.

*Complete reversibility, is evidenced by return of functional studies to normal.

Acknowledgements: B. E. Buck, M. D., of the Dept. of Pathology & Surgery, Children's Hospital of Philadelphia, and the Univ. of Miami, George Haenlein, Ph.D. et al, Louis Perelmutter, Ph.D.

Transplantation Medicine and Practice of Allergy Immunology

Objective, Conclusions: To recognize the significant impact of allergy immunology care in transplantation (liver, kidney, and cornea):

One: Infant, 6 lbs. awaiting liver transplant—biliary atresia, substantiated surgically. The grandfather, requested our clinical strategy in view of the patient's failure to thrive, awesome planned therapy. Because of the frequency of cow's milk allergy infancy and to improve preoperative, operative, postoperative care,—hypoallergenic milk plus the feature of elemental feeding—prescribed (Neocate). Consideration review—If gastrointestinal allergy existed in association with gastrointestinal congestion, the congestion could conceivably extend to the biliary region, with possible modified patency of biliary tract.

Clinical Course: More dramatic than anticipated: absence of jaundice, excellent weight gain, and patient was removed from the Transplantation List.

Two: Female, age 16, presented: severe anaphylaxis to renal dialysis (necessitated by three renal transplant rejections). Family brought all dialysis equipment obtainable (by prescription) from the area for comparative scratch testing of saline washings of equipment. Only negative reaction: Renal Systems' equipment especially coated to prevent leaching out of plastic. Reactive by history and exclusion of Clorox which was used in sterilization when the equipment was to be reused in same patient.

Clinical Course: Excellent.

Three, Four & Five: Our interest in Ophthalmologic Allergy led Ophthalmology specialist in corneal transplantation to refer these patients. His impression: Corneal transplant rejection could be preventable: carefully looking for and treating, allergic rhinitis, rhino-sinusitis prior to corneal transplantation.

| | | | |
|---|---|---|---|
| | | Clinical Course: Excellent. | |
| | Account No. Path. | Type: CS Event Location: | Jan. 29, 1998 Date: Feb. 19, 1998 OrdPhys: AttnPhys: |
| | Specimen (1) Label: Description: Specimen (2) Label: Description: Specimen (3) Label: Description: Specimen (4) Label: Description: Specimen (5) Label: Description: | | 1 COMMON BILE DUCT  2 RT HEPATIC DUCT  3 LT HEPATIC DUCT  4 LT HEPATIC DUCT  5 COMMON DUCT |
| Report: | ORDERING LOCATION: HIST Path | TEST PERFORMED AT: Status: | ARCHIVAL DIAGNOSIS; |
| | #1: COMMON BILE DUCT; | FIBROTIC TISSUE SHOWING SCATTERED SMALL DUCTS. LARGEST DUCT ON PERMANENT SECTION MEASURES 0.08 MM (80 MICRONS), THE DUCTS ON FROZEN SECTION MEASURE 0.05 MM (50 MICRONS). | |
| | #2: RIGHT HEPATIC DUCT: | FIBROSIS, NO LUMEN SEEN | |
| | #3: LEFT HEPATIC DUCT: | SMALL DUCT IN FIBROTIC TISSUE WITH CHRONIC INFLAMMATION. MAXIMUM LUMEN 0.05 MM (50 MICRONS). | |
| | #4: LEFT HEPATIC DUCT: | SMALL DUCTS IN FIBROTIC TISSUE WITH CHRONIC INFLAMMATION. MAXIMUM DIAMETER IS 0.03 MM (30 MICRONS). | |
| | #5: COMMON DUCT: | SMALL DUCTS WITHIN EXTENSIVELY FIBROTIC AND CHRONICALLY INFLAMED TISSUE. MAXIMUM LUMINAL DIAMETER 0.03 MM (30 MICRONS). | |
| | DS Feb. 20, 1998 FROZEN SECTION DX: | #1. DUCT MEASURING 0.05 MM MAXIMUM DIAMETER (WNC) #2. NO LUMEN SEEN (WNC) #3. MAXIMUM LUMEN 0.05 MM (WNC) #4. MAXIMUM DUCT DIAMETER 0.03 MM (WNC) | |
| | Specimen (1) Label: Description: Specimen (2) Label: Description: | | 1 LIVER 3x  2 GALLBLADDER |

| Clinical Course: Excellent. | | |
|---|---|---|
| ORDERING LOCATION;<br>Report: HIST | TEST PERFORMED AT<br>Path: | MEDICAL CENTER<br>Status: ARCHIVAL DIAGNOSIS; |

| | | |
|---|---|---|
| #1 | LIVER, WEDGE AND NEEDLE BIOPIES; EXTREME CENTRILOBULA<br>CHOLESTASIS WITH PORTAL TRACT FIBROSIS AND<br>DUCTILE PROLIFERATION, MOST CONSISTENT<br>WITH EXTRAHEPATIC BILIARY OBSTRUCTION,<br>EXTRAMEDULLARY HEMATOPOIESIS, NORMAL FOR<br>PATIENT'S AGE.<br>NO EVIDENCE OF INFECTION<br>(continued) | |
| Feb. 15, 1998 | 712901 | |
| | | 18D F |
| | MICROSCOPIC;<br>Sections of both wedge and needle biopsy samplings show int.<br>hepatic architecture with striking cholestasis throughout<br>lobular areas. Portal tracts show some paucity of bile duct<br>elements, however a careful quantitative evaluation of those<br>containing definite arteries indicates that about 75% also<br>contain intraseptal bile ducts (count performed by pathologist).<br>There is striking early bile ductule proliferation<br>the edge of portal tracts, consistent with extra hepatic bile<br>obstruction. Immature myeloid elements are concentrated at<br>edge of portal systems, whereas scattered clusters of erythrocytes<br>precursors are present within lobules, a distribution normal<br>late fetal and early neonatal development. There is no<br>evidence of inflammation. | |
| #2 | GALLBLADDER CYSTIC DUCT, RESECTION; PORTION OF<br>CYSTIC DUCT WITH FOCAL APPARENT ATRESIA AND<br>OBLITERATION OF MUCOSA.<br>CLINICAL CORRELATION IS SUGGESTED. | |

Proposed Indication: Treatment of Congenital Biliary Atresia and Pediatric Crohn's Disease Rationale for Therapy: Current medical treatment for the inflammatory biliary tract disease (CBA) is unavailable. Current treatment for CBA is surgical and involves major surgical risks of liver transplant, as performed in CBA. In preparation for liver transplantation the Kasai surgical procedures performed. These patients usually not responsive to the Kasai procedure (hepatoportalenterostomy) alone where the extra hepatic biliary ducts are anastomosed to the small intestines because the ductal lumen are inadequate and even if adequate cirrhosis commonly follows.

Current treatment also involves severe toxicities of standard measures and agents: the anti-rejection immunosuppressive medications such as cyclosporin and corticosteroids—lifetime requirements used to treat the inflammatory disease biliary tract disorder, the end-stage liver disease of congenital biliary atresia an inflammatory biliary tract disorder usually requiring liver transplantation related to their effects on cells other than the targeted disease cells.

Current treatment for the inflammatory digestive tract, PCD, involves major surgical risks: unfortunately major surgery can be expected requiring varying degrees of bowel resection for bowel obstruction or fistula repair in 67% to 75% of the patients. Despite this care, Crohn's disease is still incurable with a relapse rate of 75% to 80%. Current treatment also involves severe toxicities of standard measures and agents used to treat inflammatory digestive tract pediatric Crohn's disease and are related to their effects on cells other than the targeted disease cells, especially the immunosuppressive drug reactions, including the risk of neoplasm with the immunosuppressive drug used in pediatric Crohn's disease along with the use of corticosteroids growth retardation, pseudo-tumor cerebri, chemical diabetes, ocular cataracts and glaucoma, activation of a peptic ulcer. The sulfasalazine reactions include dermatitis that may be severe as Stephen Johnson's syndrome and headache.

The novel anti-inflammatory, anti-autoimmune, anti-rejection therapy, #Q101KC molar ratios formulations and, specific application for Neocate formulations and other specified molar ratios resulted in a tolerable negligible risk safety profile and demonstrated therapeutic efficacy targeted for the treatment of inflammatory digestive and biliary tract disorders, specifically CBA, an end-stage liver disease requiring transplantation. This therapeutic agent demonstrated efficacy in studies of CBA including averting the need for liver organ transplant.

Immunologic self, subset 2, and its application to subset 1 and PCD and its subsets in regard to relatively risk free anti-rejection effects of Q101KC. The pharmacodynamics herein of Q101KC anti-rejection anti-inflammatory relatively risk free medicament analogue effects of Q101KC makes it highly applicable not only for its use in subset 1, but also PCD and its subsets wherein inflammatory disease damage is so extensive that immunologic self of these subsets wherein inflammatory disease damage is so extensive that immunologic self of these target tissues are distorted until repaired by Q101KC and re-established as immunologic self.

This pharmacodynamic reaction of Q101KC anti-inflammatory anti-rejection tissue healing and Q101KC's component L amino acids and their reactive high energy, ionizing (and non-ionizing) side chain groupings are all analogue in structure and function, the in vivo synthesis of human tissue as well as medications derived therefrom.

All of these effects permit, stimulate, facilitate and accelerate tissue healing effects and recuperative systemic effect in diseased tissue, local and system effects of disease repair. All these effects of Q101KC component L amino acids and amino acids being analogue to human tissue as well as the molar ratio of tissue are, therefore, analogue to stem cell function, the newest forefront of medicament development, all highly valuable in the profound efficacy of Q101KC in the therapy of PCD and CBA.

The anti-inflammatory and healing continuum and overlay of Q101KC. The analogue highlights and rationale—Q101KC L amino acids and amino acids analogue to and mimic medicaments and human tissue with human tissue effects on PCD and CBA.

CBA subset 2, eleven cases of post hepatectomy and donor liver graft—Q101KC was also useful in those patients that had already received a liver transplant. Q101KC anti-inflammatory tissue healing effect was efficacious in minimizing symptoms suggestive of allergy. Q101KC was helpful despite failure to respond to immunosuppression and corticosteroids adequate to maintain the donor liver as anti-graft rejection medication.

Incidence of Allergic Symptoms in Pediatric Liver Transplant Recipients Treated with Tacrolimus Based Immunosuppression Prabhakaran, B. A., et al.

Purpose: This study reveals our experience with allergic symptoms in pediatric liver transplant recipients receiving primary tarolimus (FK 506) based immunosuppression.

Methods: We reviewed the charts of all patients receiving tacrolimus based immunosuppression, noting cases of severe food allergies. Patients experiencing allergies were studied for age at transplant and irritation of tacrolimus therapy, onset and type of symptoms, treatment received for allergies, resolution or persistence of allergies, and survival.

Results: Between April 1991 and October 1998, 64 pediatric liver transplant recipients (48 primary, 16 conversion) received tacrolimus based immunosuppression. Patients receiving primary tacrolimus therapy received initial doses of 0.15 mg/kg/dose PO/NG q. 12 hr. For patients converted from cyclosporin to tacrolimus, mean time until conversion was 10.5 mos. Serum tacrolimus levels were maintained between 7 and 10 mg/ml. Concomitant immunosuppression included methylprednisone and mycophenolate mofetil. Of these 64 patients, 11 (17%) experienced food allergies. For the 11 t2 yrs. (mean=13.4 mos.), whereas mean age for 53 patients who did not experience allergies was 4-6.5 mos. Mean time period between transplant and onset of allergies was 6 mos. Of the eleven patients who experienced allergies, the most common allergies were milk products (82%), eggs (64%), nuts (55%), fish (36%), wheat (27%), potatoes (27%), and soy (18%). At the time of transplant, all patients were receiving progestamil, four of eleven (36%) patients were receiving total parenteral nutrition (TPN) and two (18%) had other foods incorporated into diets. The most common symptoms of the allergic reactions were eczema, severe rashes, facial swelling, congestion, wheezing, vomiting, diarrhea and itching. Treatment of the allergic symptoms consisted of oral benadryl, hydrocortisone, nasalcron, modification of diet (switch to alimentum or neocate), and epinephrine for emergencies. Furthermore, 6 of 11 patients received oral diphenhydramine and intromuscular dexamethasone. Four of eleven patients (36%) have resolved allergies and 6 of 11 (58%) have resumed normal diets. All patients are alive at 18 mos. to 7 years post transplant and all patients currently receive tacrolimus.

Conclusions: We concluded that allergies secondary to tacrolimus immunosuppression in this group of pediatric liver transplant recipients is a noteworthy and legitimate concern. We further speculate that such problems are encountered primarily by younger patients who have yet to be exposed to a wide array of foods.

INDICATION FOR USE OF Q101KC in:

CBA Subset (1)

Q101KC L amino acid and amino acid component anti-inflammatory tissue healing effect in CBA in averting a liver transplant is analogue to the nharmacodynamic action and effect in non-surgical healing of the majority of PCD fistulae and in reducing the surgical mortality risk of those remaining cases still requiring surgery. By reducing the need for surgery, Q101KC reduces the potential mortality risk to the donor as well. Those awaiting liver transplant where Q101KC would be used to avert liver transplant (incidence is 300 new cases a year); plus any remaining cases from previous year—Estimated prevalence for 2001, 300 to 600 cases.

INDICATION FOR USE OF Q101KC in:

CBA Subset (2)

Post hepatectomy and prevention of donor graft anti-rejection phase of CBA treatment—Estimated prevalence for 2001, 5430 cases, where Q101KC is used to synergistically enhance the efficacy of anti-rejection medication and reduce the need for anti-rejection medication.

Where Q101KC with its component amino acids and L amino acids, glycine, alanine, and leucine is analogue to the oligopeptide cyclosporin anti-rejection medication, along with Q101KC's therapeutic effect in regard to the reconstitution of immunologic self as well as seriously damaged tissue to be reconstituted as immunologic self Estimated prevalence total CBA cases for 2001:

Surgically treated 4830-5130 cases

Non-surgically treated 300 to 600 cases

This anti-inflammatory tissue healing effect meets the therapeutic challenge of CBA, a disease whose treatment has to date been confined to the most extensive surgical care and most extensive post-operative care with the opportunities of averting or minimizing these types of treatments in CBA as has been accomplished in Pediatric Crohn's Disease.

Rational why such therapy is needed:

In CBA to avert or minimize surgical care even including the most extreme of surgical care—transplantation, and to avert the use of such onerous drugs such as cyclosporin and corticosteroids, (frequently lifetime use) for the above conditions of the inflammatory hepato-biliary tract diseases; in the case of PCD inflammatory bowel disease to minimize long term use of onerous drugs such as corticosteroids, mercaptopurine and major surgical care including bowel resection for serious complications including bowel obstruction and fistulae.

This is the original description of the Drug (prior to use in example 1 of#Q101KC, Therapeutic Subject Composition)

Neocate composition is currently being used as an infant formula to mimic the mother's milk but with all the protein equivalent being present so that the patient's immune system cannot identify it is allergenic protein.

This drug may also be looked upon as a biological since all components are present in the patient's blood stream: Neocate was designed to simulate the equivalent of breast milk, this product already on the market would represent the components presented to the mammary tissue before this organ produces and secretes breast milk.

The product disclosed and described in the appended patent applications for use in CBA represents the molar ratios intrinsic to liver and biliary cellular and extra-cellular hepatic tissue, as well as the molar ratio medications approaching therapeutic activity free of adverse effects of such as cyclosporin to suppress the damaged end-stage liver tissue from auto-immune rejection, as well as all other formative naturally occurring surfactants for cell and nuclear membrane component biochemical ingredients, as well as the extracellular formative collagen. In PCD molar ratios intrinsic still intestinal ileum protein will be so utilized, as well as molar ratio safe equivalent of cyclosporin where immunosuppressive effect is necessary.

It is noteworthy that this #Q101KC drug system, when licensed for pharmaceutical company manufacture distribution, is able to be integrated into scientific systems design for CBA to enhance the proposed prevention of the need for liver transplant, as well as the continued survival and viability of the excised liver for transplant and suppression of liver rejection, if the requirement for liver transplant persists. In PCD where several 5 ASA variants are available, depending upon patient response, a similar number of molar ratio formulations will be made available exemplified by #Q101KC as well as for CBA.

Scientific rationale—further description of the applied pharmacology, pathogenesis and clinical pathology, physiological chemistry, clinical and non-clinical studies and a working rationale the therapy of this grouping of inflammatory digestive and biliary tract diseases both rare conditions and the reasons why such therapy is needed are incorporated as follows:

(a) to make publicly available a non-invasive, negligible risk medical treatment for Congenital Biliary Atresia, (b) to avert the need for a liver transplant, surgical care of significant risk to both the donor and the patient requiring lifetime extensive and expensive care. This is the only currently known available and definitive treatment for this disease, (c) to extend this designation and companion successful treatment from the rare disease of infancy CBA to inflammatory digestive disease specifically Pediatric Crohn's Disease with the inclusion of many successful clinical studies and like clinical responses, as well as the sequelae of CBA inflammatory disease of hepatic cirrhosis, seen post Kasai and its intrinsic condition, liver failure, and end-stage liver disease, with the only known definitive treatment currently available for congenital biliary atresia—liver transplantation, again with significant risks. Rare disease or condition of children encompassing Congenital Biliary Atresia and long-term follow-up and Pediatric Crohn's Disease.

Inflammatory digestive and biliary tract disease in pediatrics and associated complications:

(1) Therapeutic rationale for these formulations is stressed in observations representing a substitute for corticosteroids in 84 percent of 93 patients, open trial (90% able to be discontinued with the use of these Neocate formulations; a 78 patient double blind study, flare ups occurred more rapidly when the corticosteroids were tapered than when the Neocate formulations were tapered), in this sponsor's application to lessen the need for corticosteroids in the face of relentless Crohn's inflammatory destructive effects. Those citations particularly applicable when used upon the diseased digestive tracts in children. Also administered at bedtime in pediatric Crohn's disease by way of nasogastric tube over one year with the same dramatic effects. Greatest deterrent (31 percent of active disease Crohn's patients refused use)—very poor taste acceptance, and used solely as a food replacement.

This therapeutic formulation Neocate drug may also be looked upon as a biological since all components are present in the blood stream. Neocate was designed to simulate breast milk. This product already on the market would represent the components presented to the mammary tissue before this organ produces and secretes as breast milk. Neocate until age 1 has an acceptable taste. Thereafter, has a highly unacceptable taste.

The unexpected #Q101KC findings of Girsh of use as an encapsulated medication and excellently flavored pediatric suspensions has practicalized usage of #Q101KC for CBA and PCD.

(2) Further confirmed experimentally by the Japanese in partially (with only 25% normal hepatic tissue remaining), hepatectomized animals (miniature pigs), with the use of the seven-day regrowth of liver tissue in a similar molar ratio therapeutic formulation effect as Q101KC concentration greater than the mixture of the controls. Enhances Liver Regeneration with similar effects noted in manipulation of molar ratio as Q101KC, also stressed. H. Komatsu, PhD., H. Doi, M D, et al. The Second Department of Surgery.

Tohoku University School of Medicine, Sendai, Japan. Presented at the 23rd Clinical Congress of ASPEN, San Diego, Calif., January 1999. (During the floor discussion sponsor presented his comparative clinical therapeutic response data averting the need for a liver transplant in CBA with the use of Neocate).

This experimental design model is not complicated as these clinical diseases are by inflammatory digestive and biliary tract diseases. Further description of the applied pharmacology, pathogenesis and clinical pathology, physiological chemistry, clinical and non-clinical studies and a working rationale, the therapy of this grouping of inflammatory digestive and biliary tract diseases both rare conditions and the reasons why such therapy is needed are incorporated as follows:

(3) The importance of the emulsifier component, in that the emulsifier stressed in the Harvard Medical School's publication, edited by Cotran et al cell membrane destruction as the pivotal point in reversible cellular and extracellular injury vs cell death, (4) The appearance of EPA fatty acid compound formulation targeted for anti-inflammatory anti-prostaglandin activity at the cell membrane site, (5) Girsh summary along with molar ratio design formulation availability, available by specific organ under inflammatory threat of attack, (6) Q101KC makes available molar ratio equivalent of cyclosporin (to help suppress the up-regulated T helper lymphocytes in Crohn's Disease), (7) The formation of calcium complexes serving to arrest the destructive inflammatory vicious cycle of released cytosolic calcium's (unbound free calcium is released into the cell, normally present at a 10,000 fold greater concentration outside the cell) perpetuation of phospholipid cell membrane breakdown and associated cascade of catabolic enzymatic activity, (8) All representative of a synergism of pharmacologic mechanisms with negligible risk so needed in application to such relentless diseases as inflammatory, digestive and biliary tract diseases of Biliary Atresia and Crohn's Disease of the pediatric age group. Most importantly, efficacy demonstrated utilizing negligible risk formulations as applied to formerly most refractory diseases of inflammation of the digestive and biliary tract.

These two diseases share (a.) histopathologically similar granulomatous changes, (b.) congenital biliary atresia has this similar ability to express itself and regress pathologically with the complication of formation of the granulomatous pediatric inflammatory bowel disease such as pediatric Crohn's disease even in the presence of large anti-rejection anti-inflammatory medication such as cyclosporin concurrent with heroic care necessary to interrupt course of these serious diseases involved in the necessary medical management, (c.) The dramatic therapeutic responses to #Q101KC molar ratios, specific application, with first beneficial report by the sponsor in congenital biliary atresia averting the need for liver transplant following the Kasai procedure despite poor reported prognosis because of inadequate pathologic report of lumen of 30 to 50 micron diameter INSTEAD OF A LUMEN OF 100 TO 150 MICRONS.

(9) The Pathogenesis of congenital Biliary Atresia resembling the granulomatous inflammation of pediatric Crohn's disease (Burke et al.) Children's Hosp., Phila.

In the earlier stage, a dense inflammatory infiltrate, with small number of polymorphonuclear leukocytes, numerous lymphocytes, plasma cells, and eosinophils, was present. In the latter stage mononuclear cells predominated, polymorphonuclear leukocytes were scant, but eosinophils were often still quite prominent. These histologic findings demonstrate the presence of active ductal epithelial injury, at least in the porta hepatis, characterized by a V shaped lesion on ultrasound, in this age period. There was no evidence of cytomegalovirus in any case or of hepatitis B in three of five cases. In two cases, one of the less specific techniques shower suggestive evidence of hepatitis B in the liver. These latter findings suggest that other viruses need to be sought, or cases should be studied at an earlier stage for the presence of these viruses, or both.

Liver biopsy and the extra hepatic biliary system from five patients who underwent portoenterostomy for Biliary Atresia were studies by light microscopy to delineate the character and distribution of the anatomic lesions, and by culture and immunofluorescence techniques for evidence of two viruses (cytomegalovirus and hepatitis B) which have been suspected of playing a role in the genesis of CBA.

The liver biopsies showed typical findings, with variable giant cell transformation, (suggestive of granulomatous lesion and in keeping with reported sequelae of PCD after the Kasai procedure), cholestasis, and prominent bile duct proliferation. In the areas of obliteration, no lumen dilation was evident. In the areas of obliteration there was evidence of a resolving inflammatory process.

Where the lumen was present, it tended to be small (sponsor's exhibit, attending pediatric surgeon "portended poor prognosis for the Kasai portoenterostomy procedure with the maximum biliary ductal lumen of 30 to 50 microns and poor biliary drainage noted at surgery" in excess of a hundred to hundred fifty microns biliary tract lumen for best prognosis with the exception of long-term concerns of development of hepatic cirrhosis—to perform Kasai, sphincter of Oddi function lost especially in the hepatic and common ducts. In the porta hepatis there appeared to be various stages of an evolving lesion, the earliest stage of which included extensive active epithelial injury with developing fibrosis, and the latest, more advanced fibrosis with reduction in duct lumen area.

In the Kasai procedure the presence and regulatory function of the sphincter of Oddi is absent, therefore the "back wash" of the intestinal enzymatic activity (sponsor) retrograde bacterial contamination and cholangitis, must be an important factor in the progressive cause of cirrhosis.

Although the syndrome of "infantile obstructive cholangiopathy" (neonatal hepatitis, choledochal cyst, and biliary atresia) have been associated with a number of diseases, the pathogenetic bases for this association is unclear. In the many cases that have no associated disease, the etiology and pathogenesis are completely unknown. Despite some indication of benefit from the use of portoenterostomy (Kasai procedure), the problem of prolonged infantile obstructive jaundice remains a serious one, with significant mortality and morbidity, and it appears that a completely satisfactory solution will not be reached without an understanding of the fundamental etiology(ies) and/or pathogenesis involved.

In an attempt to contribute to such an understanding. Buck, et al. have examined the liver and extra-hepatic biliary tree from five consecutive patients who underwent portoenterostomy for biliary atresia seeking clues as to etiology and pathogenesis by using light microscopy on several sections of the extra hepatic biliary tree and by using immunofluorescence and viral culture techniques on both liver and extra hepatic tree. Suspected viral infection documented in 2 of 5 cases.

(10) To extend the observations of Girsh and, this therapy will also be included, in the suspension, supporting and maximizing the vitality of the donor's transported liver for patient recipient transplantation in addition to minimizing the indications for major surgery, in this otherwise fatal disease, congenital biliary atresia, and to strive to maximize recovery and survival rate to approach 100 percent.

(11) The clinical as well as pre-clinical observations of Ser. No. 09/639,859.

An oral mucosal delivery system for Q101KC will be utilized here also. Documented in pre-clinical studies by Girsh, LS as adjunct university professor, whereby this oral delivery system was equal in measured response efficacy to the parenteral administration.

TABLE 1

Average composition of milk (100 g) of 4 species [26]

|  | Ewes | Goats | Cows | Human |
|---|---|---|---|---|
| Solids, total % | 19.30 | 12.97 | 12.01 | 12.50 |
| Energy, |  |  |  |  |
| kcal | 108 | 69 | 61 | 70 |
| KJ | 451 | 288 | 257 | 291 |
| Protein, total % | 5.98 | 3.56 | 3.29 | 1.03 |
| Lipids, total % | 7.000 | 4.14 | 3.34 | 4.38 |
| Carbohydrates, % | 5.36 | 4.45 | 4.66 | 6.89 |
| Ash, % | 0.96 | 0.82 | 0.72 | 0.20 |
| Ca, mg | 193 | 134 | 119 | 32 |
| Fe, mg | 0.10 | 0.05 | 0.05 | 0.03 |
| Mg, mg | 18 | 14 | 13 | 3 |
| P, mg | 158 | 111 | 93 | 14 |
| K, mg | 136 | 204 | 152 | 51 |
| Na, mg | 44 | 50 | 49 | 17 |
| Zn, mg | — | 0.30 | 0.38 | 0.17 |
| Ascorbic acid, mg | 4.16 | 1.29 | 0.94 | 5.00 |
| Thiamin, mg | 0.065 | 0.048 | 0.038 | 0.014 |
| Riboflavin, mg | 0.355 | 0.138 | 0.162 | 0.036 |
| Niacin, mg | 0.417 | 0.277 | 0.084 | 0.177 |
| Panthothenic acid, mg | 0.407 | 0.310 | 0.314 | 0.223 |
| Vitamin B6, mg | — | 0.046 | 0.042 | 0.011 |
| Folacin, mcg | — | 1 | 5 | 5 |
| Vitamin, B12, mcg | 0.711 | 0.065 | 0.357 | 0.045 |
| Vitamin A, |  |  |  |  |
| RE | 42 | 56 | 31 | 64 |
| IU | 147 | 185 | 126 | 241 |
| Saturated FA, g | 4.60 | 2.67 | 2.08 | 2.01 |
| C4:0, g | 0.20 | 0.13 | 0.11 | — |
| C6:0, g | 0.14 | 0.09 | 0.06 | — |
| C8:0, g | 0.14 | 0.10 | 0.04 | — |
| C10:0, g | 0.40 | 0.26 | 0.08 | 0.06 |
| C12:0, g | 0.24 | 0.12 | 0.09 | 0.26 |
| C14:0, g | 0.66 | 0.32 | 0.34 | 0.32 |
| MCT total |  |  |  |  |
| (C6-C14), g | 1.58 | 0.89 | 0.61 | 0.64 |
| C16:0, g | 1.62 | 0.91 | 0.88 | 0.92 |
| C18:0, g | 0.90 | 0.44 | 0.40 | 0.29 |
| Monounsat, FA, g | 1.72 | 1.11 | 0.96 | 1.66 |
| C16:1, g | 0.13 | 0.08 | 0.08 | 0.13 |
| C18:1, g | 1.56 | 0.98 | 0.84 | 1.48 |
| C20:1, g | — | — | trace | 0.04 |
| C22:1, g | — | — | trace | trace |

TABLE 1-continued

Average composition of milk (100 g) of 4 species [26]

|  | Ewes | Goats | Cows | Human |
|---|---|---|---|---|
| Polyunsat, FA, g | 0.31 | 0.15 | 0.12 | 0.50 |
| C18:2, g | 0.18 | 0.11 | 0.08 | 0.37 |
| C18:3, g | 0.13 | 0.04 | 0.05 | 0.05 |
| C18:4, g | — | — | trace | — |
| C20:4, g | — | — | trace | 0.03 |
| C20:5, g | — | — | trace | trace |
| C22:5, g | — | — | trace | trace |
| C22:6, g | — | — | trace | trace |
| Cholesterol, mg | — | 11 | 14 | 14 |
| Phytosterol, mg | — | — | trace | — |
| L Amino Acids: |  |  |  |  |
| Tryptophan, g | 0.084 | 0.044 | 0.046 | 0.017 |
| Threonine, g | 0.268 | 0.163 | 0.149 | 0.046 |
| Isoleucine, g | 0.338 | 0.207 | 0.199 | 0.056 |
| Leucine, g | 0.587 | 0.314 | 0.322 | 0.095 |
| Lysine, g | 0.513 | 0.290 | 0.261 | 0.068 |
| Methionine, g | 0.155 | 0.080 | 0.083 | 0.021 |
| Cysteine, g | 0.035 | 0.046 | 0.030 | 0.019 |
| Phenlyalanine, g | 0.284 | 0.155 | 0.159 | 0.046 |
| Tyrosine, g | 0.281 | 0.179 | 0.159 | 0.053 |
| Valine, g | 0.448 | 0.240 | 0.220 | 0.063 |
| Arginine, g | 0.198 | 0.119 | 0.119 | 0.043 |
| Histidine, g | 0.167 | 0.089 | 0.089 | 0.023 |
| Alanine, g | 0.269 | 0.118 | 0.113 | 0.036 |
| Aspartic acid, g | 0.328 | 0.210 | 0.250 | 0.082 |
| Glutamic acid, g | 1.019 | 0.626 | 0.689 | 0.168 |
| Glycine, g | 0.041 | 0.050 | 0.070 | 0.026 |
| Proline, g | — | 0.368 | 0.319 | 0.082 |
| Serine, g | 0.492 | 0.181 | 0.179 | 0.043 |

TABLE 2

Relative composition of ewe and goat milk in relation to the composition of human milk = 100% [26]

|  | Ewe | Goat | Cow |
|---|---|---|---|
| Solids, total | 154 | 104 | 96 |
| Energy | 154 | 99 | 87 |
| Protein | 580 | 346 | 319 |
| Fat | 160 | 94 | 76 |
| Lactose | 78 | 64 | 68 |
| Minerals | 480 | 410 | 360 |
| Ca | 603 | 419 | 372 |
| Fe | 333 | 167 | 167 |
| Mg | 600 | 457 | 433 |
| P | 1128 | 793 | 664 |
| K | 267 | 400 | 298 |
| Na | 259 | 294 | 288 |
| Zn | N/A | 176 | 224 |
| Ascorbic acid | 83 | 26 | 19 |
| Thiamin | 464 | 343 | 271 |
| Riboflavin | 986 | 383 | 450 |
| Niacin | 236 | 156 | 474 |
| Pantothenic acid | 182 | 139 | 141 |
| Vitamin B6 | N/A | 418 | 382 |
| Folacin | N/A | 20 | 100 |
| Vitamin B12 | 1580 | 144 | 793 |
| Vitamin A | 65 | 88 | 48 |
| Saturated fatty acids | 229 | 133 | 103 |
| C4:0 butyric | 2000 | 1300 | 1100 |
| C6:0 caproic | 1400 | 900 | 600 |
| C8:0 caprylic | 1400 | 1000 | 400 |
| C10:0 capric | 667 | 433 | 133 |
| C12:0 lauric | 92 | 46 | 35 |
| C14:0 myristic | 206 | 100 | 106 |
| C16:0 palmitic | 176 | 99 | 96 |
| C18:0 stearic | 310 | 152 | 138 |
| Monounsaturated FA | 104 | 67 | 58 |
| C16:1 palmitoleic | 100 | 62 | 62 |
| C18:1 oleic | 105 | 66 | 57 |

TABLE 2-continued

Relative composition of ewe and goat milk in relation to the composition of human milk = 100% [26]

|  | Ewe | Goat | Cow |
|---|---|---|---|
| Polyunsaturated FA | 62 | 30 | 24 |
| C18:2 linoleic | 49 | 30 | 22 |
| C18:3 linolenic | 260 | 80 | 100 |
| MCT-FA C6:0-C12:0 | 288 | 178 | 84 |
| Cholesterol | N/A | 79 | 100 |
| Tryptophan | 494 | 259 | 270 |
| Threonine | 583 | 354 | 324 |
| -Isoleucine | 604 | 370 | 355 |
| -·Leucine | 618 | 330 | 339 |
| Lysine | 754 | 426 | 384 |
| -Methionine | 738 | 381 | 395 |
| Cysteine | 184 | 242 | 158 |
| ·Phenylalanine | 617 | 337 | 346 |
| ·Tyrosine | 530 | 338 | 300 |
| -Valine | 711 | 381 | 349 |
| Arginine | 460 | 277 | 277 |
| Histidine | 726 | 387 | 387 |
| -Alanine | 747 | 328 | 314 |
| Aspartic acid | 400 | 256 | 305 |
| Glutamic acid | 606 | 373 | 410 |
| -Glycine | 158 | 192 | 269 |
| ·Proline | N/A | 449 | 389 |
| Serine | 1144 | 421 | 416 |

-= cyclosporin analog of utility patent
·= yogurt and amino acids

BRIEF DESCRIPTION OF THE FIGURES

FIG. 3 is a schematic of different kinds of surfactant aggregation.

FIG. 5A shows the structural formula of phosphatidyl choline (PC).

FIG. 5B shows the structural formula of phosphatidyl sarine (PS).

FIG. 5C shows the structural formula of phosphatidyl ethanolamine (PE).

FIG. 5D shows the structural formula of N-Acylphosphatidyl ethanolamine (NAPE).

FIG. 6A shows the structural formula of phosphatidyl inositol (PI).

FIG. 6B shows the structural formula of phosphatidyl glycerol (PG).

FIG. 6C shows the structural formula of phosphatidic acid (PA).

FIG. 6D shows the structural formula of plasmogen, wherein X=choline or ethanolamine.

FIG. 6E shows the structural formula of diphosphatidyl glycerol (DPG).

Figure 1A:
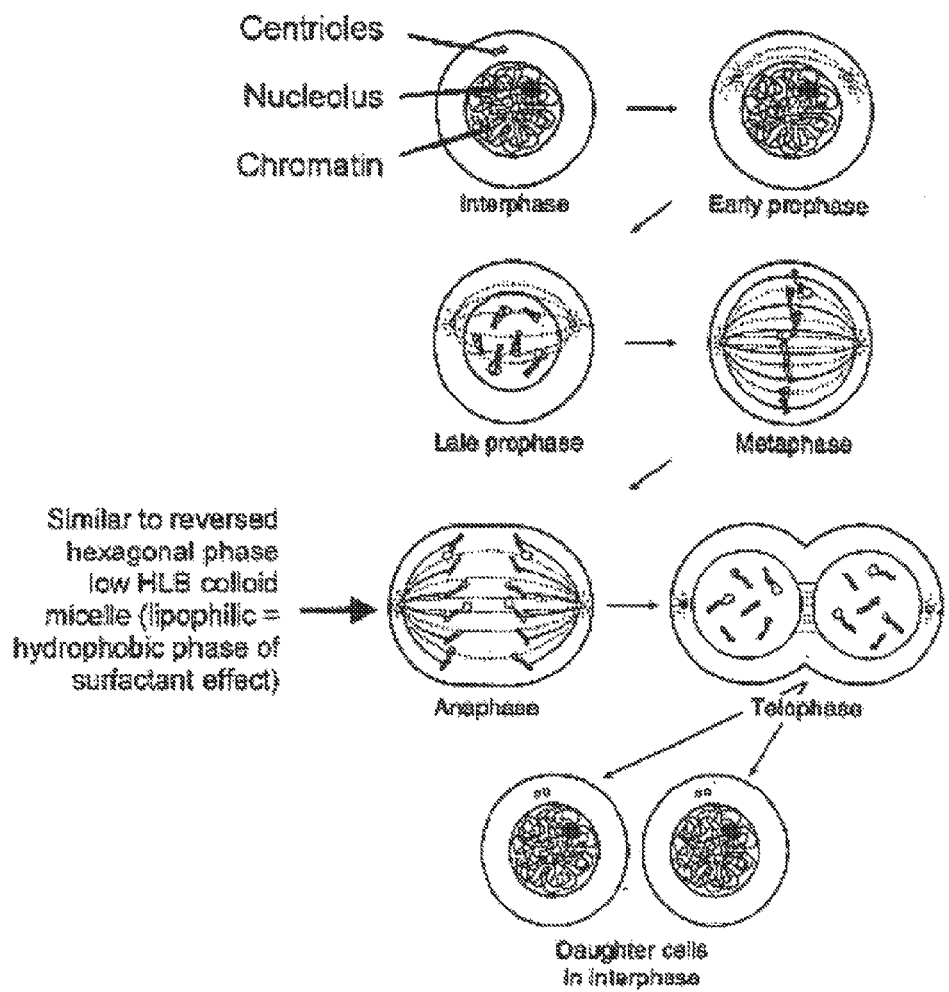
FIG. 1A is a schematic drawing of the phases of mitosis. Similar to reversed hexagonal phase low HLB colloid micelle (lipophilic=hydrophobic phase of surfactant effect). Factors of mitosis include genetic distribution, mobilization of membrane of cell, cell nuclei, and intranuclear phospholipids.
Figure 1B:
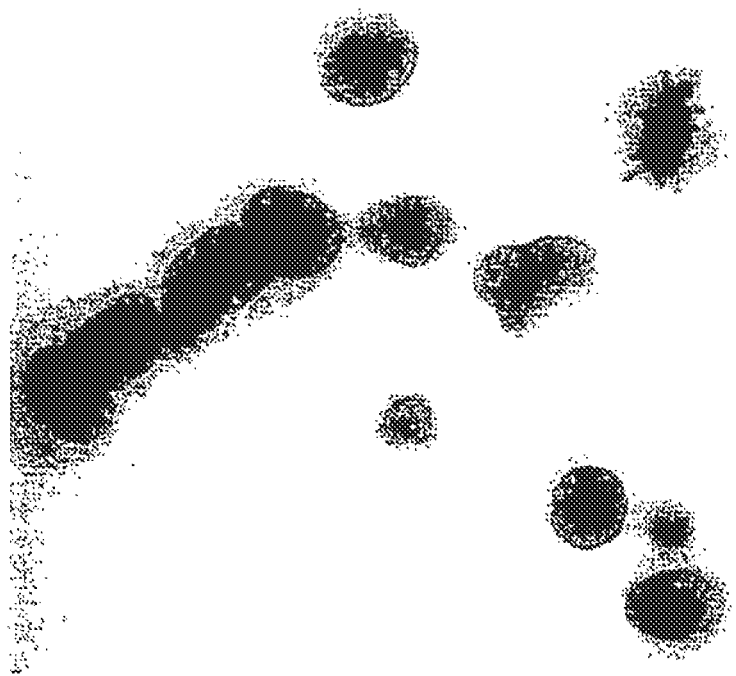
FIG. 1B shows cerebrospinal fluid showing metastatic breast cancer cells and abnormal mitosis (mitotic figures) of cancer.
Figure 2:
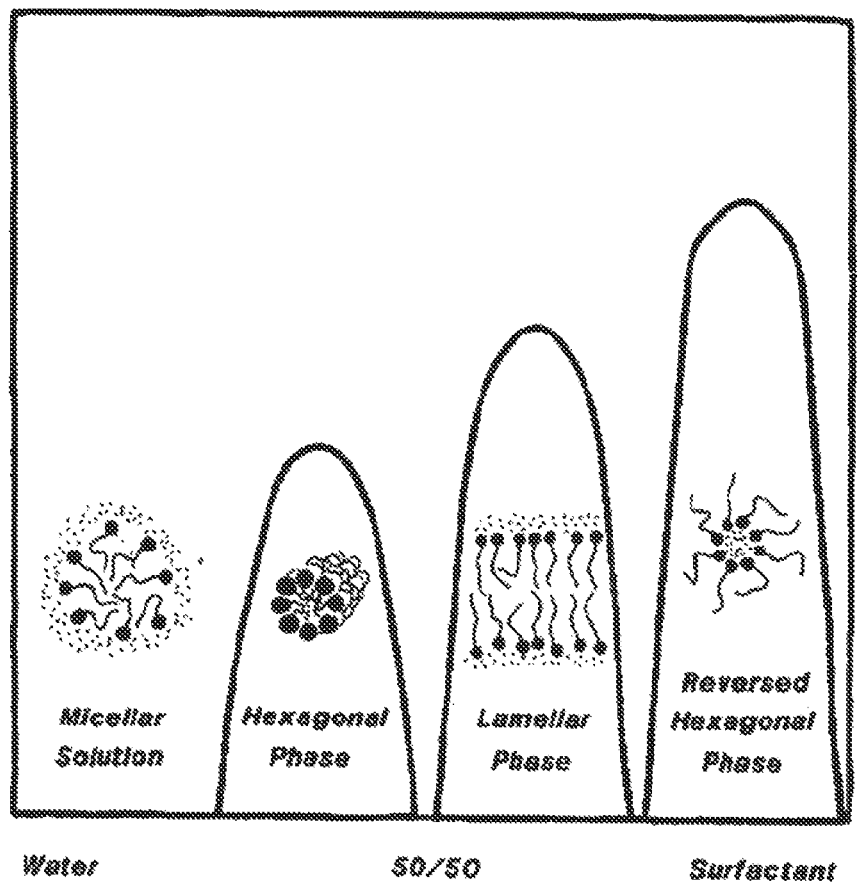
FIG. 2 is a schematic of surfactant forces in emulsions. It shows the typical sequence of phases that develops when a surfactant is mixed with water. Hydrophilic surfactant as high HLB of 18 of Tween80. Lipophilic(hydrophobic)low HLB surfactants (e.g. lecithin 4 to 7). Cancer appears as an uncontrolled phase equivalent in its extensive mitosis to lipophilic reversed hexagonal phase micelle.
Figure 4:
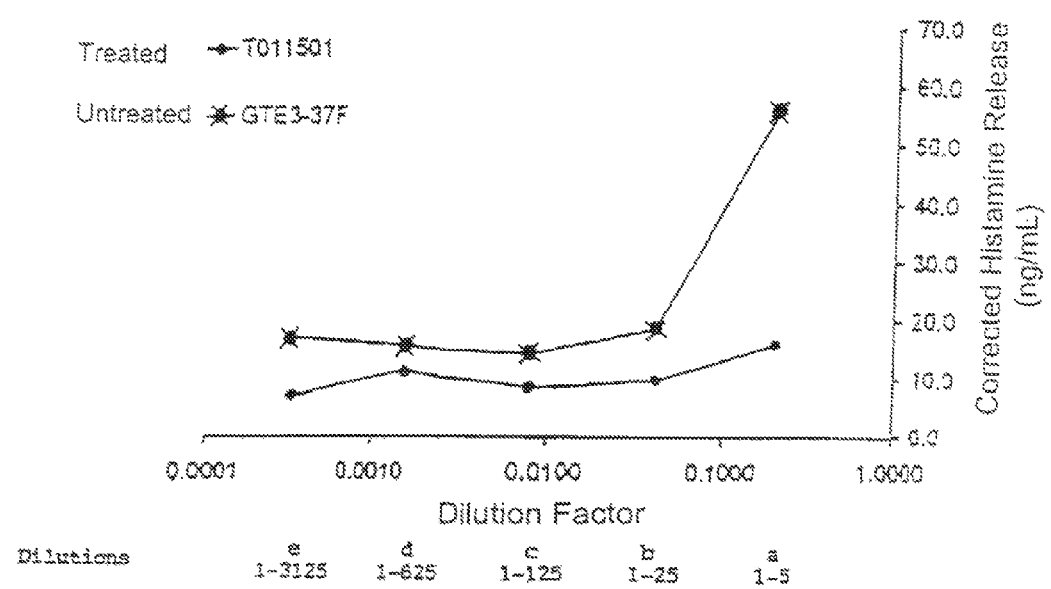
FIG. 4 is a graphical representation of the amount of histamine released in response to different dilution factors of the treatment to reduce the allergenicity of cat dander.
Figure 7A:
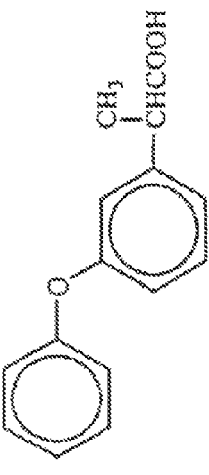
FIG. 7A shows the structural formula of ibuprofen.
Figure 7B:
FIG. 7B shows the structural formula of fenoprofen.
Figure 7C:
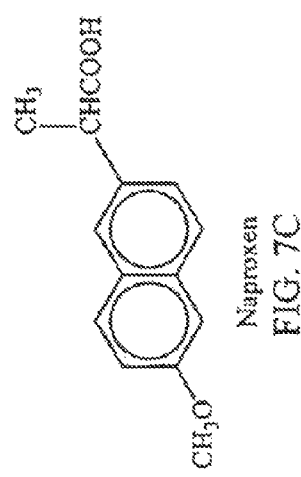
FIG. 7C shows the structural formula of naproxen.
Figure 7D:
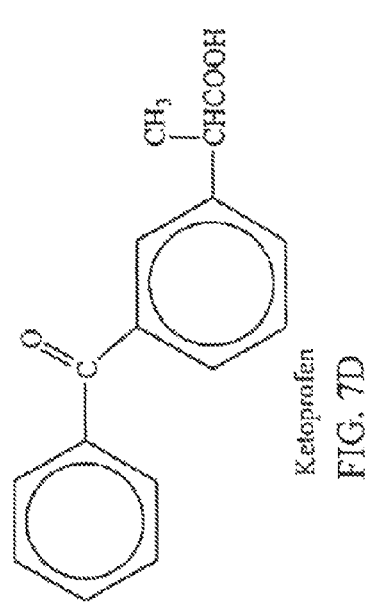
FIG. 7D shows the structural formula of ketoprofen.
Figure 7E:
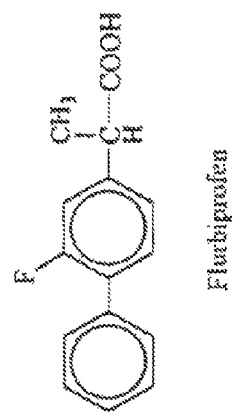
FIG. 7E shows the structural formula of flurbiprofen.
Figure 8:
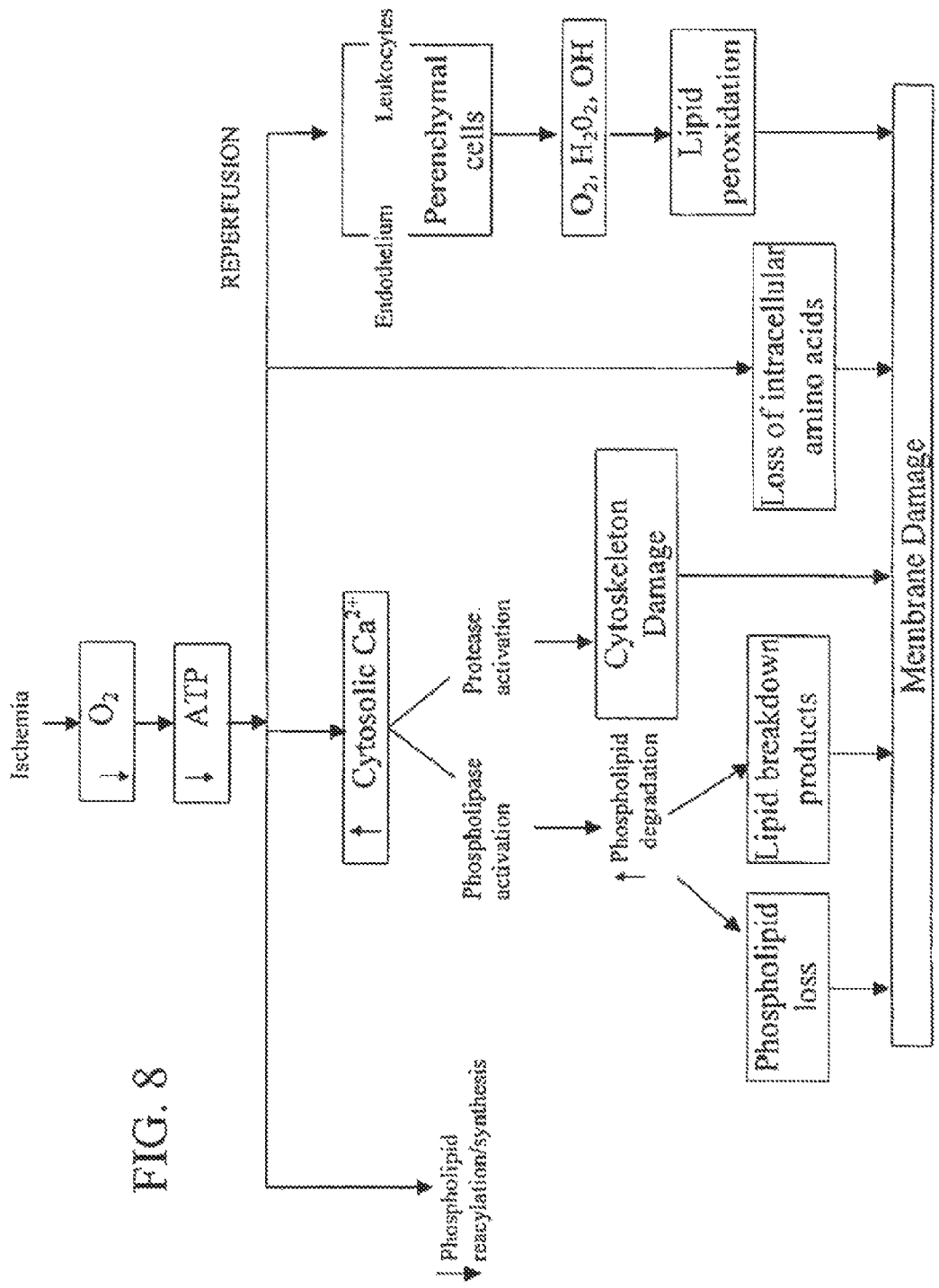
FIG. 8 shows the mechanism of membrane damage in ischemia and reperfusion.
Figure 9A:
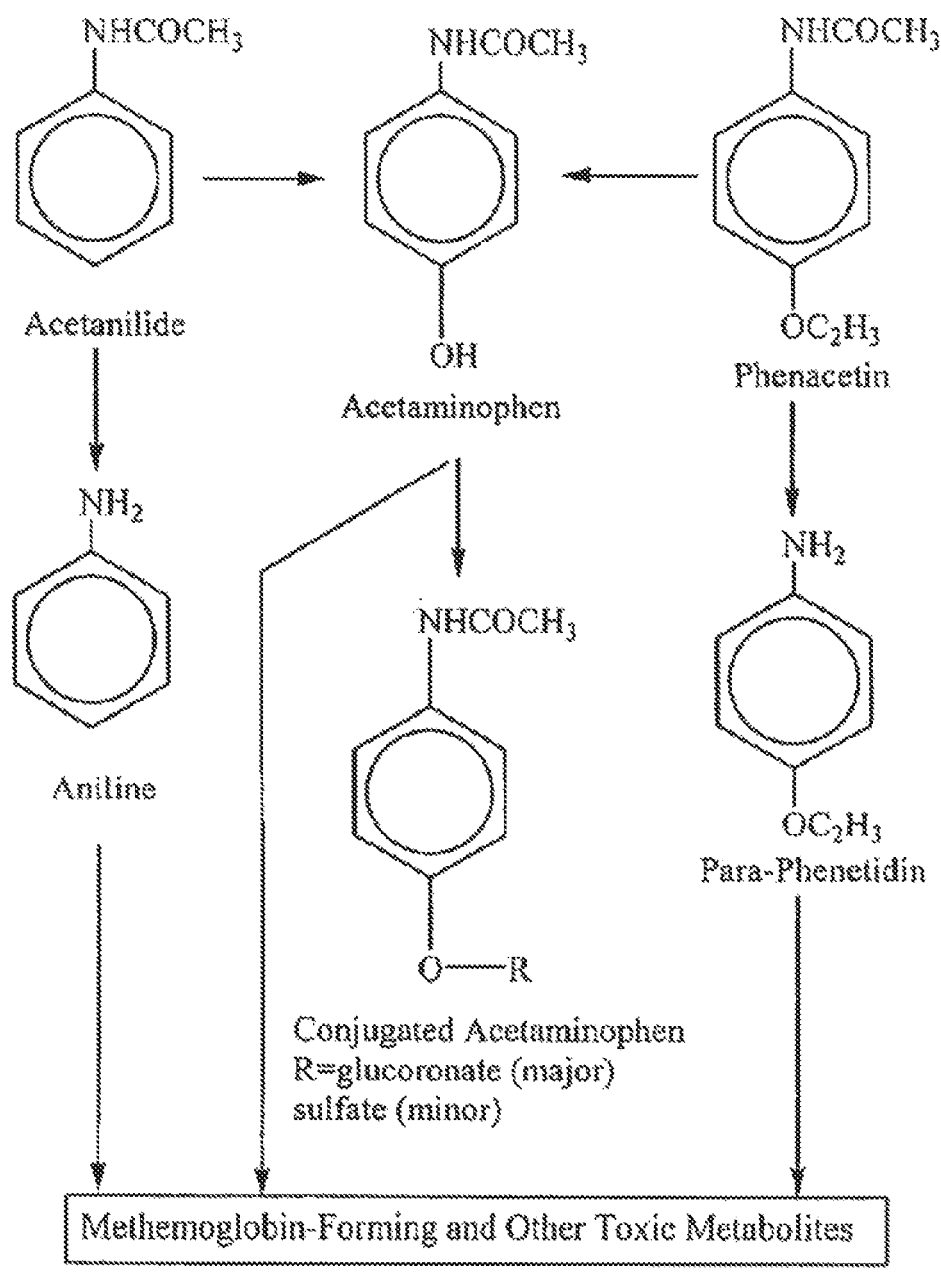
FIG. 9A shows the structural formulas of several para-aminophenol derivatives.
Figure 9B:
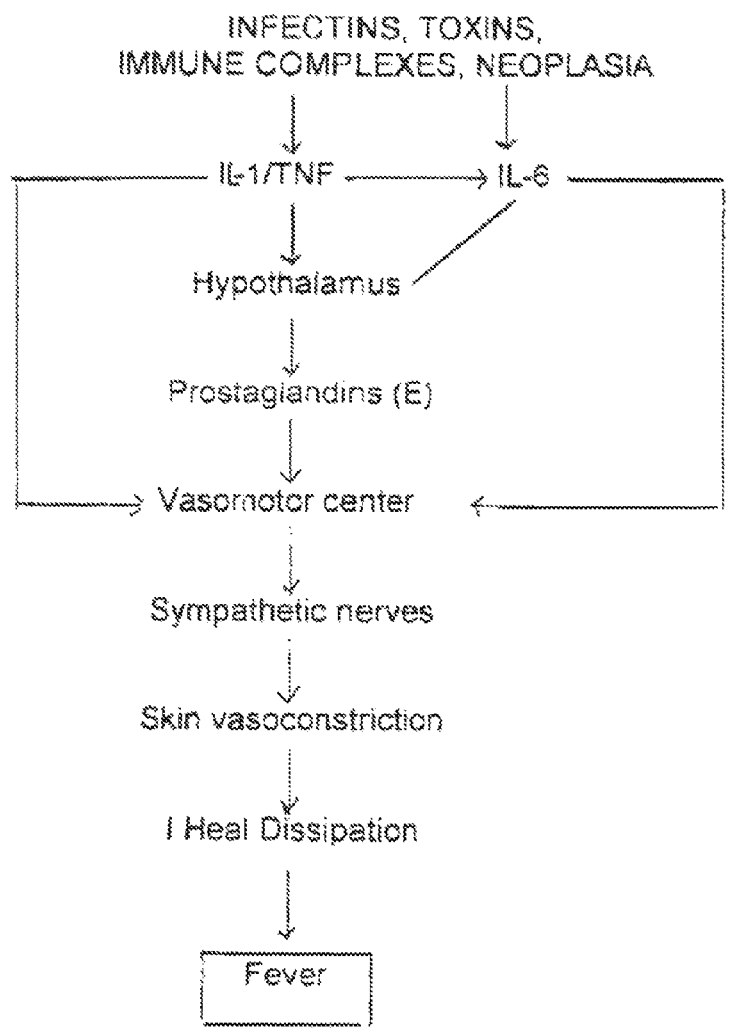
FIG. 9B is a schematic drawing of the antipyretic action of acetaminophen. Similar biochemical groupings, the amino and phenol moieties as in tyrosine and down regulation IL1/TNF and IL6 as an anti-inflammatory component of the subject composition.
Figure 10A:
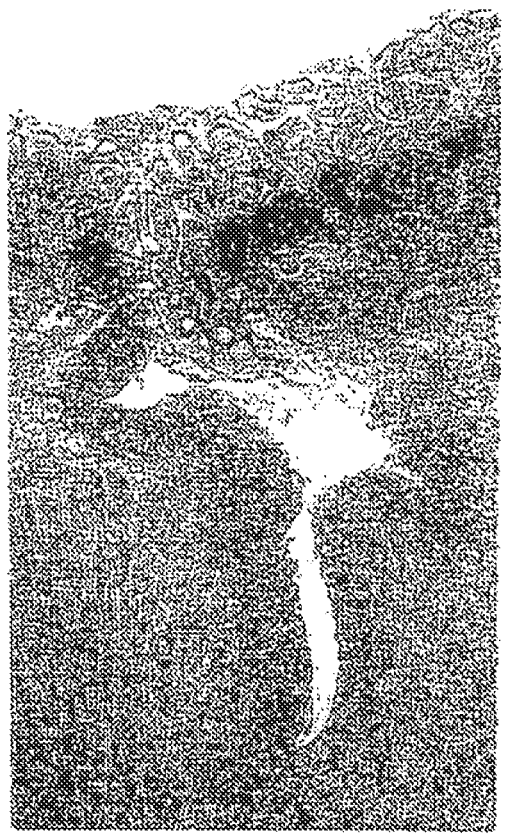
FIG. 10A shows a low power micrograph of the pathology of Crohn's disease. Extensive pathologic changes normalized in 2-4 weeks with therapeutic subject composition.
Figure 10B:
FIG. 10B shows Crohn's disease granuoloma of the colon. Extensive pathologic changes normalized in 2-4 weeks with therapeutic subject composition.
Figure 11A:
FIG. 11A shows Indium III Abnormal radiogram of ileal inflammation.
Figure 11B:
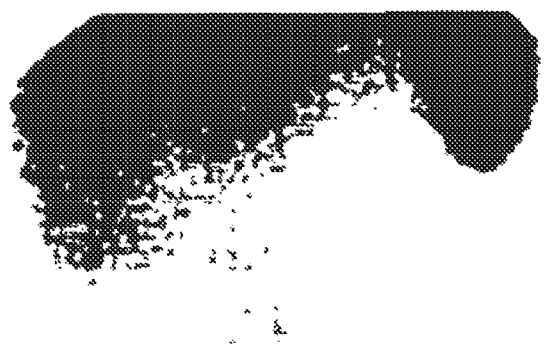
FIG. 11B shows a normalized Ileum 4 weeks after treatment with therapeutic subject composition.
Figure 12:
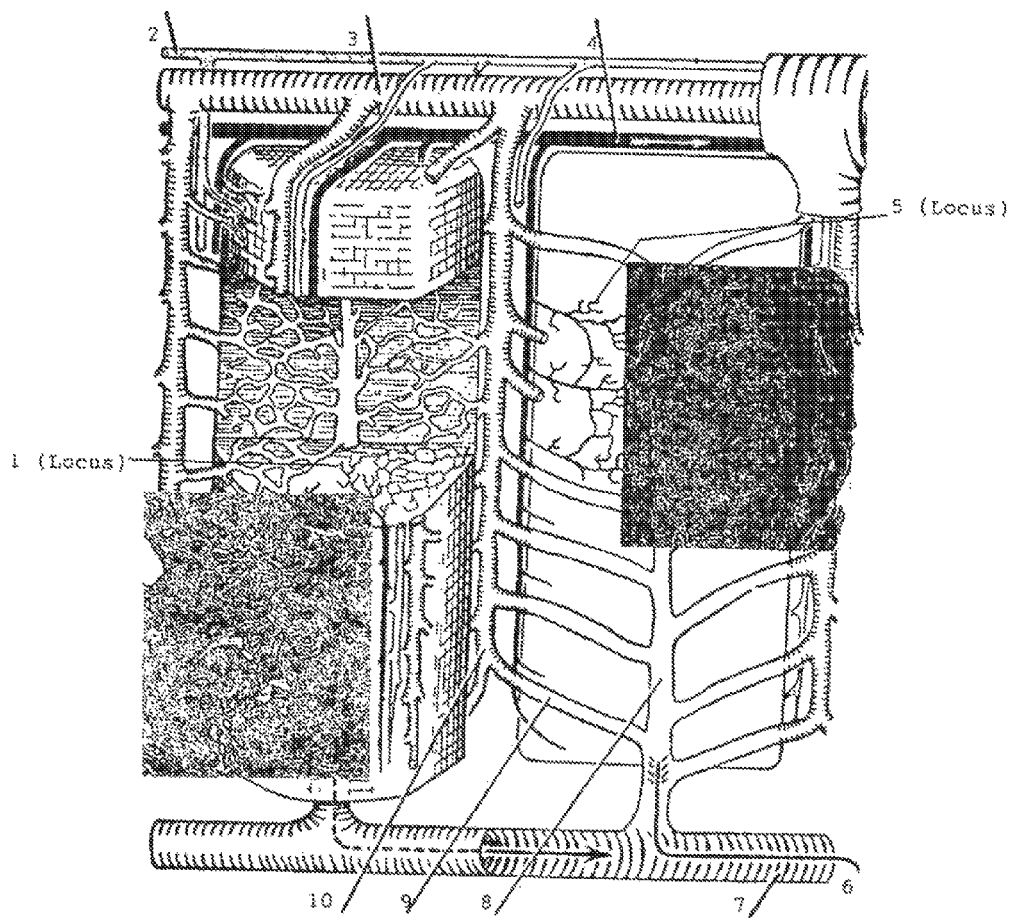
FIG. 12 is a schematic drawing of a liver illustrating the locus of congenital biliary atresia disease being close to the location of stem cells and in approximately the area of believed therapeutic activity. Biliary atresia is evidenced by a sheet of periductular inflammation and fibrosis. Extensive periductule inflammation as seen on this H and E slide. This inflammatory obstruction also prevents reanastomosis of the biliary ductules diagrammatically illustrated here by superimposing the histopathology of biliary atresia upon the normal microscopic anatomy of the liver.

1. Locus (location)—See text
2. Hepatic Artery
3. Portal Vein
4. Bile Duct
5. Locus (location)—See text
6. To Hepatic Veins and inferior Vena Cava
7. Sublobular Vein to Hepatic Veins and Inferior Vena Cava
8. Central Vein
9. Sinusoid
10. Interlobular Vein

I claim:

1. A method for reducing the allergenicity of animal dander, the method applying to the animal dander, a solution comprising:
   a) polysorbate 80 at a concentration ranging from about 0.25% to about 2%;
   b) an acceptable carrier at a concentration ranging from about 0.1% to about 50%, wherein the acceptable carrier is glycerine; and
   c) a non-toxic alcohol at a concentration ranging from about 0.1% to about 50%, wherein the non-toxic alcohol is ethyl alcohol or isopropyl alcohol.

2. The method according to claim 1, wherein the acceptable carrier is at a concentration ranging from about 0.1% to about 5%.

3. The method according to claim 1, wherein the non-toxic alcohol is at a concentration ranging from about 0.1% to about 5%.

4. The method according to claim 1, further comprising phosphatidylcholine at a concentration ranging from about 0.5% to about 1%; and sodium lauryl sulfate at a concentration ranging from about 0.5% to about 1%.

5. The method according to claim 1, wherein the reduction in allergenicity is measured using a Bradford assay or ELISA.

6. The method according to claim 5, wherein there is a reduction in allergenicity of at least 45-fold as measured by the Bradford assay.

7. The method according to claim 5, wherein there is a reduction in allergenicity of at least 5% as measured by ELBA.

\* \* \* \* \*